US009314505B2

(12) United States Patent
Wise et al.

(10) Patent No.: US 9,314,505 B2
(45) Date of Patent: Apr. 19, 2016

(54) COMBINATION TREATMENTS AND COMPOSITIONS FOR WOUND HEALING COMPRISING VIRAL VEGF

(71) Applicants: Lyn Marie Wise, Dunedin (NZ); Stephen Bruce Fleming, Dunedin (NZ); Andrew Allan Mercer, Dunedin (NZ)

(72) Inventors: Lyn Marie Wise, Dunedin (NZ); Stephen Bruce Fleming, Dunedin (NZ); Andrew Allan Mercer, Dunedin (NZ)

(73) Assignee: OTAGO INNOVATION LIMITED (NZ)

( * ) Notice: Subject to any disclaimer, the term of this patent is extended or adjusted under 35 U.S.C. 154(b) by 0 days.

(21) Appl. No.: 13/897,280

(22) Filed: May 17, 2013

(65) Prior Publication Data

US 2013/0323201 A1    Dec. 5, 2013

Related U.S. Application Data

(60) Provisional application No. 61/649,213, filed on May 18, 2012.

(51) Int. Cl.
*A61K 38/00* (2006.01)
*A61K 38/20* (2006.01)
*A61K 38/18* (2006.01)

(52) U.S. Cl.
CPC ......... *A61K 38/2066* (2013.01); *A61K 38/1866* (2013.01)

(58) Field of Classification Search
CPC combination set(s) only.
See application file for complete search history.

(56) References Cited

U.S. PATENT DOCUMENTS

| | | | |
|---|---|---|---|
| 4,940,456 A | 7/1990 | Sibalis et al. | |
| 5,002,551 A | 3/1991 | Linsky et al. | |
| 5,064,655 A | 11/1991 | Uster et al. | |
| 5,080,646 A | 1/1992 | Theeuwes et al. | |
| 5,147,296 A | 9/1992 | Theeuwes et al. | |
| 5,169,383 A | 12/1992 | Gyory et al. | |
| 5,279,544 A | 1/1994 | Gross et al. | |
| 5,320,850 A | 6/1994 | Gale et al. | |
| 5,362,308 A | 11/1994 | Chien et al. | |
| 5,484,604 A | 1/1996 | Solomon et al. | |
| RE35,474 E | 3/1997 | Woodard et al. | |
| 5,681,580 A | 10/1997 | Jang et al. | |
| 5,695,779 A | 12/1997 | Mori | |
| 5,718,914 A | 2/1998 | Foldvari | |
| 5,749,847 A | 5/1998 | Zewert et al. | |
| 5,910,306 A | 6/1999 | Alving et al. | |
| 5,968,006 A | 10/1999 | Hofmann | |
| 5,983,135 A | 11/1999 | Avramhami | |
| 6,041,253 A | 3/2000 | Kost et al. | |
| 6,190,315 B1 | 2/2001 | Kost et al. | |
| 6,224,853 B1 | 5/2001 | Steel et al. | |
| 6,248,349 B1 | 6/2001 | Suzuki et al. | |
| 6,391,015 B1 | 5/2002 | Millot | |
| 6,391,311 B1 * | 5/2002 | Ferrara et al. | 424/198.1 |
| 6,487,447 B1 | 11/2002 | Weimann et al. | |
| 6,491,657 B2 | 12/2002 | Rowe et al. | |
| 6,512,950 B2 | 1/2003 | Li et al. | |
| 6,553,255 B1 | 4/2003 | Miller et al. | |
| 6,575,956 B1 | 6/2003 | Brisken et al. | |
| 6,587,705 B1 | 7/2003 | Berner et al. | |
| 6,613,325 B1 | 9/2003 | Amery et al. | |
| 6,689,803 B2 | 2/2004 | Hunter | |
| 6,692,456 B1 | 2/2004 | Eppstein et al. | |
| 6,706,032 B2 | 3/2004 | Weaver et al. | |
| 6,712,805 B2 | 3/2004 | Weimann | |
| 6,720,001 B2 | 4/2004 | Chen et al. | |
| 6,730,318 B2 | 5/2004 | Quan et al. | |
| 6,731,987 B1 | 5/2004 | McAdams et al. | |
| 6,750,291 B2 | 6/2004 | Kim et al. | |
| 6,759,056 B2 | 7/2004 | Jordan | |
| 6,841,153 B1 | 1/2005 | Chegini et al. | |
| 6,842,641 B2 | 1/2005 | Weimann et al. | |
| 6,868,286 B1 | 3/2005 | Hille et al. | |
| 6,893,655 B2 | 5/2005 | Flanigan et al. | |
| 6,946,144 B1 | 9/2005 | Jordan | |
| 6,951,658 B1 | 10/2005 | Pearson et al. | |
| 7,004,933 B2 | 2/2006 | McDaniel | |
| 7,008,637 B2 | 3/2006 | Jacobsen et al. | |
| 7,033,998 B2 | 4/2006 | Fishman | |
| 7,052,715 B2 | 5/2006 | Fishman | |
| 7,201,919 B2 | 4/2007 | Jordan | |
| 7,232,431 B1 | 6/2007 | Weimann | |
| 7,261,882 B2 * | 8/2007 | Watkins | 424/85.2 |
| 7,291,591 B2 | 11/2007 | Fishman | |
| 8,247,384 B2 * | 8/2012 | Green et al. | 514/44 A |
| 2006/0240116 A1 * | 10/2006 | Jolley | 424/535 |

OTHER PUBLICATIONS

Wise et al. -Vegf-E enhances wound closure by promoting re-epithelialization and reducing granulation tissue formation. J. Vasc. Res. 49, S1-12, p. 37, 2011).*
NCBI search results for VEGF-E, accessed Sep. 30, 2014.*
Grimstad et al., Cellular sources and inducers of cytokines present in acute wound fluid, Wound Repair and Regeneration, 19, 337-347, 2011.*
McColl et al., APMIS, 2004, 463-480, 112(7-8).
Michaels et al., Wound Repair Regen., 2005, 506-512, 13(5).
Minhas et al., FASEB J., 2010, 873-881, 24(3).
Mori et al., J. Cell Sci., 2006, 5193-5203, 119(24).
Mori et al., J. Exp. Med., 2008, 43-51, 205(1).
Nissen et al., Am. J. Pathol., 1998, 1445-1452, 152(6).
Niu et al., J. Biol. Chem., 2007, 6001-6011, 282(9).
Oliveira et al., Int. Wound J., 2009, 445-452, 6(6).

(Continued)

*Primary Examiner* — Elly-Gerald Stoica
(74) *Attorney, Agent, or Firm* — Acuity Law Group, P.C.; Bradford J. Duft; Daniel M. Chambers

(57) ABSTRACT

Viral VEGF and viral anti-inflammatory cytokine compositions, methods of treatment using them, and kits containing them for use in the promotion and/or improvement of wound healing and/or tissue repair, and for anti-scarring, anti-inflammatory, anti-fibrosis and anti-adhesion indications.

31 Claims, 20 Drawing Sheets

(56) References Cited

OTHER PUBLICATIONS

Olsson et al., Nat. Rev. Mol. Cell. Biol., 2006, 359-371, 7(5).
Peranteau et al., J. Invest. Dermatol., 2008, 1852-1860, 128(7).
Qiu et al., Curr. Biol., 2003, 1697-1703, 13(19).
Rheinwald et al., Nature, 1977, 421-424, 265(5593).
Romano Di Peppe et al., Gene Ther., 2002, 1271-1277, 9(19).
Savage et al., Proc. R. Soc. Med., 1972, 766-768, 65(9).
Savory et al., J. Virol., 2000, 10699-10706, 74(22).
Seo et al., Am. J. Physiol. Cell Physiol., 2001, C1568-C1578, 281(5).
Shibuya, Angiogenesis, 2006, 225-230, 9(4).
Shih et al., Wound Repair Regen., 2010, 139-153, 18(2).
Soker et al., J. Cell. Biochem., 2002, 357-368, 85(2).
Stein et al. (Eds)., Applied Antisense Oligonucleotide Technology, 1998, Wiley-Liss, NY (Table of Contents).
Tan et al., Br. J. Plast. Surg., 1991, 465-467, 44(6).
Vadasz et al., Autoimmun. Rev., 2010, 825-829, 9(12).
Weninger et al., Lab. Invest., 1996, 647-657, 75(5).
Werner et al., J. Invest. Dermatol., 2007, 998-1008, 127(5).
Wilson et al., ASAIO Trans., 1990, M340-M343, 36(3).
Wise et al., J. Biol. Chem., 2003, 38004-38014, 278(39).
Wise et. al., J. Gen. Virol., 2007, 1677-1682, 88(6).
Wise et al., Virus Res., 2007, 115-125, 128(1-2).
Wise et al., Cell. Microbiol., 2012, 1376-1390, 14(9).
Xia et al., Blood, 2003, 161-168, 102(1).
Yang et al., Proc. Natl. Acad. Sci. USA, 1998, 10836-10841, 195(18).
Zheng et al., Arterioscler. Thromb. Vasc. Biol., 2006, 2019-2026, 26(9).
Zheng et al., Arterioscler. Thromb. Vasc. Biol., 2007, 503-511, 27(3).
Aidoudi et al., Thromb. Haemost., 2010, 941-948, 104(5).
Ando et al., J. Invest. Dermatol., 1993, 633-639, 100(5).
Applied Biosystems User Bulletin #2, 1997, 1-36.
Avdic et al., J. Virol., 2011, 7465-7471, 85(14).
Barrientos et al., Wound Repair Regen, 2008, 585-601, 16(5).
Brem et al., J. Invest. Dermatol., 2009, 2275-2287, 129(9).
Brown et al., J. Exp. Med., 1992, 1375-1379, 176(5).
Brown et al., J. Immunol., 1995, 2801-2807, 154(6).
Canavese et al., Histol. Histopathol., 2011, 285-296, 26(3).
Carmeliet, Nat. Med., 2000, 1102-1103, 6(10).
Carmeliet et al., Nature, 2011 298-307, 473(7347).
Chalmers, Int. Wound J., 2011, 218-223, 8(3).
Chan et al., J. Gen. Virol., 2006, 3177-3181, 87(11).
Chou et al., Ad. Enzyme Reg., 1984, 27-55, 22.
Courtman et al., J. Biomed. Mater. Res., 1994, 655-666, 28(6).
Detmar, J. Invest. Dermatol., 2004, xiv-xv, 122(1).
Devalaraja et al., J. Invest. Dermatol., 2000, 234-244, 115(2).
Dipietro et al., Am. J. Pathol., 1995, 868-875, 146(4).
Dizerega et al., in Dizerega et al. (Eds.), The Peritoneum, 1992, 307-369, Springer-Verlag, NY.
Elias et al., Am. J. Pathol., 2008, 689-699, 173(3).
Ferrara, Endocr. Rev., 2004, 581-611, 25(4).
Fleming et al., J. Virol., 1997, 4857-4861, 71(6).
Friedman, Semin. Liver Dis., 1999, 129-140, 19(2).
Gharaee-Kermani et al., J. Biol. Chem., 1996, 17779-17784, 271(30).
Goliger et al., Mol. Biol. Cell, 1995, 1491-1501, 6(11).
Gosselet et al., Cell. Signal., 2007, 731-739, 19(4).
Groves et al., J. Am. Acad. Dermatol., 1991, 706-711, 25(4).
Gurel et al., Eur. J. Dermatol., 2002, 183-185, 12(2).
Haig et al., Vet. Res., 1998, 311-326, 29(3-4).
Haig et al., Virus Res., 2002, 303-316, 90(1-2).
Harlow et al. (Ed.), Antibodies: A Laboratory Manual, 1988, Cold Spring Harbor Publications, NY (Table of Contents).
Harlow et al. (Ed.), Using Antibodies: A Laboratory Manual, 1999, Cold Spring Harbor Publications, NY (Table of Contents).
Holmes et al., Cell. Signal., 2007, 2003-2012, 19(10).
Hunskaar, Br. J. Dermatol., 1986, 631-634, 114(5).
Imlach et al., J. Gen. Virol., 2002, 1049-1058, 83(5).
Inder et al., Febs J., 2008, 207-217, 275(1).
Inoue et al., Arterioscler. Thromb. Vasc. Biol., 2007, 99-105, 27(1).
Jackson et al., Wound Repair Regen., 2005, 284-294, 13(3).
Jain et al., Nat. Med., 2003, 685-693, 9(6).
Jenkinson et al., Vet. Dermatol., 1990, 189-195, 1(4).
Johns, Hum. Reprod. Update, 2001, 577-579, 7(6).
Kaiser et al., J. Invest. Dermatol., 1998, 1145-1152, 111(6).
Kiba et al., Biochem. Biophys. Res. Comm., 2003, 371-377, 301(2).
Koch et al., Biochem. J., 2011, 169-183, 437(2).
Kotenko et al., Proc. Natl. Acad. Sci. USA, 2000, 1695-1700, 97(4).
Kuehn, JAMA, 2007, 938-939, 297(9).
Lateef et al., J. Gen. Virol., 2003, 1101-1109, 84(5).
Li et al., J. Gastroenterol. Hepatol., 1999, 618-633, 14(7).
Li et al., Diabetes, 2007, 656-665, 56(3).
Malone et al., J. Vasc. Surg., 1984, 181-191, 1(1).
Olsson et al., VEGF receptor signalling—in control of vascular function, Nat. Rev. Mol. Cell. Biol., 2006, 359-371, 7(5).

* cited by examiner

A.

B.

A.

B.

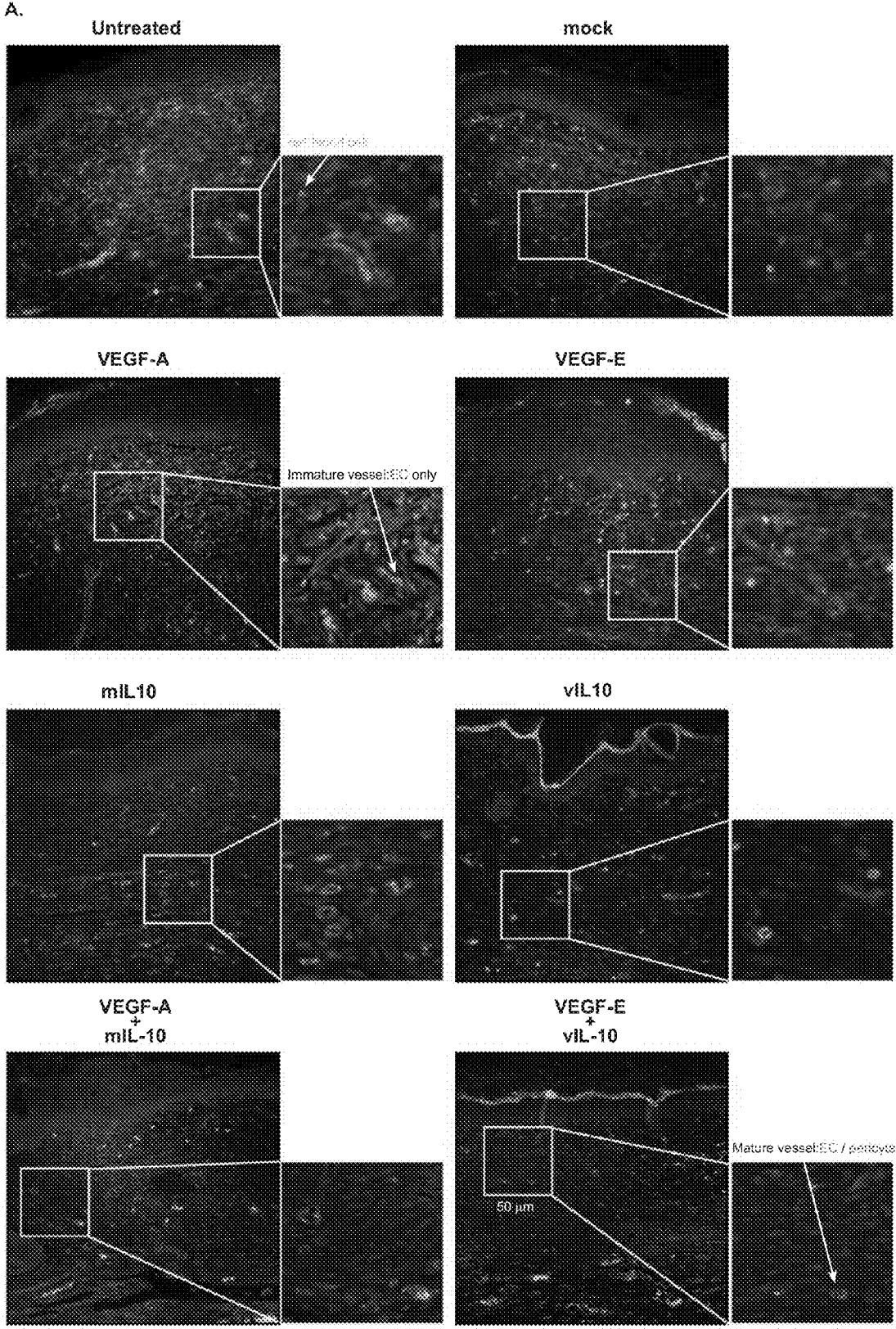

COMBINATION TREATMENTS AND COMPOSITIONS FOR WOUND HEALING COMPRISING VIRAL VEGF

RELATED APPLICATION

This application claims the benefit of and priority to U.S. provisional patent application Ser. No. 61/649,213, filed 18 May 2012 and entitled, "Combination Treatments and Compositions for Wound Healing," the contents of which are hereby incorporated by reference in their entirety for any and all purposes.

TECHNICAL FIELD

The inventions relate to compositions and methods that involve combinations of viral and other proteins, for example viral vascular endothelial growth factors and anti-inflammatory cytokines. These inventions are useful in various contexts, including to promote wound healing and to treat wounds, in particular acute wounds and wounds that do not heal at expected rates, such as delayed-healing wounds, incompletely healing wounds, chronic wounds, and dehiscent wounds. The inventions are also useful in reducing fibrosis, adhesions, inflammation and scarring.

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art.

In humans and other mammals wound injury triggers an organized complex cascade of cellular and biochemical events that will in most cases result in a healed wound. An ideally healed wound is one that restores normal anatomical structure, function, and appearance on cellular, tissue, organ, and organism levels. Wound healing, whether initiated by trauma, microbes or foreign materials, proceeds via a complex process encompassing a number of overlapping phases, including inflammation, epithelialization, angiogenesis and matrix deposition. Normally, these processes lead to a mature wound and a certain degree of scar formation. Although inflammation and repair mostly occur along a prescribed course, the sensitivity of the process is dependent on the balance of a variety of wound healing molecules, including for example, a network of regulatory cytokines and growth factors.

Wounds that do not heal at normal or expected rates, including chronic wounds, such as diabetic foot ulcers, pressure ulcers, and venous leg ulcers (VLU), are an increasing worldwide problem. It is estimated, for example, that 1-2% of the population in Western countries will develop a chronic wound over the course of their lifetimes. Chronic wounds represent a major economic burden on healthcare services, with an estimated annual expenditure in the United States alone of up to $25 billion. Kuehn B M, Chronic wound care guidelines issued. *JAMA* 297: 938-939, 2007. An estimated 1.3 million to 3 million US individuals are believed to have pressure ulcers; and as many as 10-15% of the 20 million individuals with diabetes are at risk of developing chronic ulcers. Many more have venous ulcers or wounds that result from arterial disease. With growing numbers of elderly and diabetics in the population, this expenditure figure is expected to rise in coming years. Unfortunately, there are few effective therapeutic options for these debilitating wounds, and there remains a significant need for effective new treatments. While, over the years, basic and clinical research has revealed much about the individual molecular and cellular processes involved in wound healing, attempts to accelerate and/or improve wound healing by enhancing, inhibiting, or modifying isolated aspects of the wound healing process have met with only limited success.

Scars are the result of wounds that have healed, lesions due to diseases, or surgical operations. Hypertrophic and keloid scars occur when the tissue response is out of proportion to the amount of scar tissue required for normal repair and healing. Certain regions of the body, including back, shoulders, sternum and earlobe, are especially prone to develop abnormal scars known as hypertrophic scars or keloids. These scars are bulky lesions representing an increased deposition of collagen fibers. They have the same clinical appearance: they are red, raised, and firm and posses a smooth, shiny surface. Whereas hypertrophic scars can flatten spontaneously in the course of one to several years, keloids persist and extend beyond the site of the original injury. As thickened red scars that exceed the boundary of an injury and may grow for a prolonged period of time, keloids are hyperplastic connective tissue masses that occur in the dermis and adjacent subcutaneous tissue, most commonly following trauma, in certain susceptible individuals. Keloid lesions are formed when local skin fibroblasts undergo vigorous hyperplasia and proliferation in response to local stimuli. The increase in scar size is due to deposition of increased amounts of collagen into the tissue. African-Americans are genetically prone to developing keloids. Keloid development has been associated with different types of skin injury including surgery, ear piercing, laceration, burns, vaccination or inflammatory process. Hypertrophic scars are masses which can result from burns or other injuries to the skin. Such scars are usually permanent and resistant to known methods of therapy. Patients suffering from hypertrophic scars or keloids complain about local pain, itchiness and local sensitivity, all of which compromise their quality of life as well as affect the individual body image.

Various therapies for keloids have had only limited success. Existing efforts to manage hypertrophic scars and keloids include surgery, mechanical pressure, steroids, x-ray irradiation and cryotherapy. Disadvantages have been reported to be associated with each of these methods. For example, surgical removal of the scar tissue may be often incomplete and can result in the development of hypertrophic scars and keloids at the incision and suture points, i.e., scarring frequently recurs after a keloid is surgically removed, and steroid treatments may be unpredictable and often result in depigmentation of the skin. Simple surgical excision of keloid scars has a 50%-80% risk of recurrence. A combination of surgery with either intralesional corticosteroid injection or radiotherapy has been a typical treatment. However, intralesional corticosteroid injection is prone to complications (fat atrophy, dermal thinning, and pigment changes).

Atrophic or depressed scars resulting from an inflammatory episode are characterized by contractions of the skin, and leave a cosmetically displeasing and permanent scar. The most common example is scarring which occurs following inflammatory acne or chickenpox. The depression occurs as a normal consequence of wound healing, and the scar tissue causing the depression is predominantly comprised of collagen resulting from fibroblast proliferation and metabolism. Some acne patients are successfully treated using steroids injected intralesionally, topical liquid nitrogen applications, or dermabrasion. In many cases, however, there is either no improvement or the treatment results in other complications.

Scars that cross joints or skin creases at right angles are prone to develop shortening or contracture. Scar contractures occur when the scar is not fully matured, often tend to be hypertrophic, and are typically disabling and dysfunctional. They are common after burn injury across joints or skin concavities. For scar contractures, surgical release with splinting, acrylic casting, and compression therapy may be required. Full thickness and split or partial thickness skin grafts and, perhaps more effectively, local and free flaps are used for reconstruction of difficult and extensive scars and contractures.

Adhesion formation is a process in which bodily tissues that are normally separate become connected by scar tissue. Adhesions most commonly result from surgical incision, abrasion, or trauma. Adhesions can form following most any type of surgery, but develop with the highest frequency following general abdominal, gynecologic, orthopedic, and cardiac surgeries. It has been reported that following abdominal surgery the incidence of peritoneal adhesion formation may be as high as 90%. See U.S. Pat. No. 6,613,325. The incidence of adhesion formation is also thought to be as high as 90% in patients that have undergone multiple surgeries. Post operative intraperitoneal and pelvic adhesions represent a major problem in patients recovering from surgery in the abdominal cavity, where there is a tendency for adhesions to form between the affected tissues. See U.S. Pat. No. 5,002,551. The pervasiveness of this problem also has severe economic consequences.

Although adhesions occur most commonly following surgery, adhesions may also occur from tissue damage other than surgery, including traumatic injury, inflammatory disease, intraperitoneal chemotherapy and radiation therapy. Amongst other complications, the presence of surgical adhesions may be associated with pain, discomfort, and female infertility resulting from gynecological surgery. Intestinal obstructions, for example, are a complication that results from surgical adhesions. Adhesions are also reported to be a leading cause of bowel obstruction and infertility, and related complications include chronic pelvic pain, urethral obstruction and voiding dysfunction. See U.S. Pat. No. 6,689,803. Adhesion formation may result from injury to the peritoneum, which in turn may cause the site of injury or trauma to become inflamed. Although inflammation is a part of the healing process, it can contribute to adhesion formation by contributing to the development of fibrous bands of scar tissue. Through a process called fibrinolysis, the fibrin bands eventually dissolve. However, where fibrin bands do not dissolve, they can develop into proliferating adhesions that connect and bind to organs and tissues that are normally separate. It has been reported that excess production and deposition of the extracellular matrix may be a key factor in producing tissue fibrosis throughout the body including the development of peritoneal adhesions (see U.S. Pat. No. 6,841,153).

Various approaches for the prevention of adhesion formation have been reported. See Dizerega, G. S. & Rodgers, K. E., "Prevention of Postoperative Adhesions," in "The Peritoneum," Dizerega, G. S. & Rodgers, K. E., eds., Springer-Verlang, New York, pp. 307-369 (1992). General categories of treatment for adhesions that have been reported, include: 1) prevention of fibrin deposition in the peritoneal exudate, 2) reduction of local tissue inflammation; and 3) removal of fibrin deposits. Id. However, despite years of research it has been reported that very few products for the prevention of post-operative adhesions have resulted. Johns, A., *Human Reproductive Update*, 7 (6):577-579 (2001). Meanwhile, the medical problems associated with surgical adhesions are becoming more serious because there is a general rise in repeat surgical procedures for a number of disorders. Thus, there is a vital need for the development of compounds and methods for preventing surgical adhesions and mitigating the complications they cause.

Fibroproliferative diseases, including pulmonary fibrosis, systemic sclerosis, liver cirrhosis, cardiovascular disease, progressive kidney disease, and macular degeneration, are a leading cause of morbidity and mortality and can affect all tissues and organ systems. Fibrotic tissue remodeling can also influence cancer metastasis and accelerate chronic graft rejection in transplant recipients. Nevertheless, despite its enormous impact on human health, there are currently no approved treatments that directly target the mechanism(s) of fibrosis.

Fibrosis is the abnormal accumulation of fibrous tissue that can occur as a part of the wound-healing process in damaged tissue. Examples of fibrosis include liver fibrosis, lung fibrosis (e.g., silicosis, asbestosis, idiopathic pulmonary fibrosis), oral fibrosis, endomyocardial fibrosis, retroperitoneal fibrosis, deltoid fibrosis, kidney fibrosis (including diabetic nephropathy), and glomerulosclerosis. Liver fibrosis, for example, occurs as a part of the wound-healing response to chronic liver injury. Fibrosis can occur as a complication of haemochromatosis, Wilson's disease, alcoholism, schistosomiasis, viral hepatitis, bile duct obstruction, exposure to toxins, and metabolic disorders. This formation of fibrotic tissue is believed to represent an attempt by the body to encapsulate injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death. Endomyocardial fibrosis is an idiopathic disorder that is characterized by the development of restrictive cardiomyopathy. In endomyocardial fibrosis, the underlying process produces patchy fibrosis of the endocardial surface of the heart, leading to reduced compliance and, ultimately, restrictive physiology as the endomyocardial surface becomes more generally involved. Endocardial fibrosis principally involves the inflow tracts of the right and left ventricles and may affect the atrioventricular valves, leading to tricuspid and mitral regurgitation. Oral submucous fibrosis is a chronic, debilitating disease of the oral cavity characterized by inflammation and progressive fibrosis of the submucosal tissues (lamina propria and deeper connective tissues). It results in marked rigidity and an eventual inability to open the mouth. The buccal mucosa is the most commonly involved site, but any part of the oral cavity can be involved, even the pharynx. Retroperitoneal fibrosis is characterized by the development of extensive fibrosis throughout the retroperitoneum, typically centered over the anterior surface of the fourth and fifth lumbar vertebrae. This fibrosis leads to entrapment and obstruction of retroperitoneal structures, notably the ureters. In most cases, the etiology is unknown. However, its occasional association with autoimmune diseases and its response to corticosteroids and immunosuppressive therapy suggest it may be immunologically mediated. Deltoid fibrosis is a muscle disorder marked by intramuscular fibrous bands within the substance of the deltoid muscle. These bands lead to secondary contractures that affect the function of the shoulder joint. Scapular winging and secondary scoliosis also may be related to this condition. Deltoid fibrosis has been associated with fibrous contractures of the gluteal and quadriceps muscles and is likely a similar process Understanding of the cellular and biochemical mechanisms underlying liver fibrosis has advanced in recent years (reviewed by Li and Friedman, *J. Gastroenterol. Hepatol.*

14:618-633, 1999). Stellate cells are believed to be a major source of extracellular matrix in the liver. Stellate cells respond to a variety of cytokines present in the liver, some of which they also produce (Friedman, *Seminars in Liver Disease* 19:129-140, 1999). As summarized by Li and Friedman, actual and proposed therapeutic strategies for liver fibrosis include removal of the underlying cause (e.g., toxin or infectious agent), suppression of inflammation (using, e.g., corticosteroids, IL-1 receptor antagonists, or other agents that may suppress inflammation), down-regulation of stellate cell activation (using, e.g., gamma interferon or antioxidants), promotion of matrix degradation, or promotion of stellate cell apoptosis. Despite recent progress, many of these strategies are still in the experimental stage, and existing therapies are aimed at suppressing inflammation rather than addressing the underlying biochemical processes. Thus, there remains a need in the art for materials and methods for treating fibrosis, including liver fibrosis.

Orf virus, the type species of the Parapoxvirus genus, causes localised proliferative skin lesions in ungulates and humans (Haig and Mercer, *Vet Res* 29, 311-26, 1998), with extravagantly proliferative and persistent lesions reported in immune-compromised individuals (Gurel et al., *Eur J Dermatol* 12, 183-5, 2002; Hunskaar, *Br J Dermatol* 114, 631-4, 1986; Savage et al., *Proc R Soc Med* 65, 766-8, 1972, Tan et al., *Br J Plast Surg* 44, 465-7, 1991). Orf virus infection initiates in the regenerating epidermis of wounded skin and the lesions progress through stages of erythema, papule, vesicle, pustule and then scab formation (Haig and Mercer, *Vet Res* 29, 311-26, 1998; Jenkinson et al., *Vet Dermatol* 1, 189-95, 1990). Orf virus lesions have been described as reminiscent of a sustained wound healing response, as they are characterized by extensive blood vessel proliferation and dilation and epidermal hyperplasia (Groves et al., *J Am Acad Dermatol* 12, 706-11, 1991, Savory et al., *J Virol* 74, 10699-706, 2000).

Vascular endothelial growth factors (VEGFs) are key regulators of angiogenesis during normal physiological and disease processes such as wound healing (Carmeliet and Jain, *Nature* 473, 298-307, 2011, Ferrara, *Endocr Rev* 25, 581-611, 2004, McColl et al., *Apmis* 112, 463-80, 2004). The VEGF family, which includes VEGF-A, VEGF-B, VEGF-C, VEGF-D and placental growth factor (PlGF), interact with the high-affinity VEGF receptors (VEGFRs), VEGFR-1, VEGFR-2 and VEGFR-3 (Koch et al., *Biochem J* 437, 169-83, 2011; Olsson et al., *Nat Rev Mol Cell Biol*, 7, 359-71, 2006). VEGF-A binds to both VEGFR-1 and VEGFR-2, whilst PlGF and VEGF-B bind exclusively to VEGFR-1. VEGF-C and VEGF-D interact with both VEGFR-2 and VEGFR-3. VEGFs also bind the co-receptors neuropilin (NRP)-1 and NRP-2, which enhance binding to the VEGFRs (Soker et al., *J Cell Biochem* 85, 357-68, 2002; Vadasz et al., *Autoimmun Rev* 9, 825-829, 2010). VEGF-A has been shown to promote angiogenesis by stimulating endothelial cell proliferation, migration and survival and promoting vascular permeability, primarily through VEGFR-2 (Holmes et al., *Cell Signal* 19, 2003-2012, 2007). VEGFR-1, however, appears to play a role in endothelial cell differentiation and migration, possibly by acting as a ligand-binding molecule, sequestering VEGF-A from VEGFR-2 signaling (Shibuya, *Angiogenesis* 9, 225-230, 2006). During cutaneous tissue repair, VEGF-A is highly expressed by keratinocytes and stimulates the formation of new blood vessels in the wound bed, supplying nutrients and oxygen needed for regeneration of the skin (Barrientos et al., *Wound Repair Regen* 16, 585-601, 2008; Brown et al., *J Exp Med* 176, 1375-1379, 1992; Nissen et al., *Am J Pathol* 152, 1445-1452, 1998). In addition, a number of studies have shown that VEGF-A also enhances healing by promoting re-epithelialization of wounds (Brem et al., *J Invest Dermatol* 129, 2275-2287, 2009; Li et al., *Diabetes* 56, 656-665, 2007; Michaels et al., *Wound Repair Regen* 13, 506-512, 2005; Romano Di Peppe et al., *Gene Ther* 9, 1271-1277, 2002). VEGF-A also increases vascular leakage and promotes the formation of disorganized blood vessels (Carmeliet, *Nat Med* 6, 1102-1103, 2000). Several other skin disorders are linked to a high presence of VEGF-A, such as psoriasis (Detmar, *J Invest Dermatol* 122, xiv-xv, 2004), skin cancer (Weninger et al., *Lab Invest* 75, 647-657, 1996), dermatitis herpetiformis and erythema multiforme (Brown et al., *J Immunol* 154, 2801-2807, 1995). VEGF-A overexpression in transgenic mice, with epidermal trauma, induces psoriatic-like lesions characterized by prominent angiogenesis, inflammation and epidermal hyperplasia (Canavese et al., *Histol Histopathol* 26, 285-296, 2011; Elias et al., *Am J Pathol* 173, 689-699, 2008; Xia et al., *Blood* 102, 161-168, 2003).

It has been reported that the extensive vascular changes found beneath the orf virus lesions are in part, if not solely due to the expression of a VEGF homolog encoded by this virus. In the absence of a functional viral VEGF, the infected lesions lack not only the striking proliferation of blood vessels and dermal edema but also the distinctive pattern of epidermal hyperplasia and rete ridge formation seen in wild-type infections (Savory et al., *J Virol* 74, 10699-10706, 2000; Wise et al., *Virus Res* 128, 115-125, 2007). It has also been reported that purified orf virus VEGF, which has been designated VEGF-E, promotes angiogenesis and epidermal regeneration through its interaction with VEGFR-2, but shows negligible vascular leakage and tissue inflammation as it fails to bind VEGFR-1 (Inder et al., *Febs J* 275, 207-217, 2008; Inoue et al., *Arterioscler Thromb Vasc Biol* 27, 99-105, 2007; Kiba et al., *Biochem Biophys Res Commun* 301, 371-377, 2003; Wise et al., *J Biol Chem* 278, 38004-38014, 2003; Wise et al., *Cellular Microbiology* 14 (9) 1376-1390, 2012; Zheng et al., *Arterioscler Thromb Vasc Biol* 26, 2019-2026, 2006; Zheng et al., *Arterioscler Thromb Vasc Biol* 27, 503-511, 2007).

Interleukin-10 (IL-10), also known as human cytokine synthesis inhibitory factor (CSIF), is an anti-inflammatory cytokine. In humans IL-10 is encoded by the IL10 gene. This cytokine is produced primarily by monocytes and to a lesser extent by lymphocytes and keratinocytes. It has pleiotropic effects in immunoregulation and inflammation. It down-regulates the expression of Th1 cytokines, MHC class II antigens, and costimulatory molecules on macrophages. It also enhances B cell survival, proliferation, and antibody production. IL-10 can block NF-κB activity, and is involved in the regulation of the JAK-STAT signaling pathway. IL-10 is capable of inhibiting synthesis of pro-inflammatory cytokines such as IFN-γ, IL-2, IL-3, TNFα and GM-CSF made by cells such as macrophages and regulatory T-cells. It also displays a potent ability to suppress the antigen-presentation capacity of antigen presenting cells. However, it is also stimulatory towards certain T cells and mast cells and stimulates B cell maturation and antibody production. IL-10 is mainly expressed in monocytes and Type 2 T helper cells (TH2), mast cells, $CD4^+CD25^+Foxp3^+$ regulatory T cells, and also in a certain subset of activated T cells and B cells. It is released by cytotoxic T-cells to inhibit the actions of NK cells during the immune response to viral infection.

Many viruses exploit the strategy of using homologs of cellular cytokines or cytokine receptors to shield virus-infected cells from immune defenses and enhance virus survival in the host. Human cytomegalovirus (HCMV) is a species-specific betaherpesvirus that infects a majority of the world's population. HCMV establishes and maintains a life-long latent infection in primitive myeloid lineage cells. Following terminal cell differentiation of these cells into myeloid dendritic cells (DCs) and macrophages, latent virus has the ability to reactivate, resulting in the production of new, infectious virions and often severe disease in immunocompromised individuals. Only a subset of viral genes are transcriptionally active during latency, including HCMV UL111A, a gene that encodes homologs of the potent immunomodulatory cytokine human interleukin-10 (hIL-10). UL111A is transcriptionally active during both productive and latent phases of infection and encodes several viral IL-10 proteins which exert a diverse range of immunomodulatory functions, including inhibition of cytokine synthesis and major histocompatibility complex (MHC) expression by myeloid cells, stimulation of B cells, and suppression of DC maturation and cytotrophoblast function. See Avdic, S, et al., Viral Interleukin-10 Expressed by Human Cytomegalovirus during the Latent Phase of Infection Modulates Latently Infected Myeloid Cell Differentiation, *J. Virol.* July 2011 85: 7465-7471. A number of herpes viruses also harbor homologs of IL-10. Epstein-Barr virus (EBV)-encoded IL-10 (ebvIL-10), the first viral homolog of IL-10 identified, shares many but not all of the biological activities of cellular IL-10 and may play an important role in the host-virus interaction. In addition to EBV, the Orf poxvirus (OV), which can infect humans, has its own IL-10 homolog, ovIL-10. See Kotenko, S V, et al., Human cytomegalovirus harbors its own unique IL-10 homolog (cmvIL-10), *PNAS* 97: 1695-1700 (2000). ORFV-IL-10 is functionally similar to cellular IL-10 in that it has the capacity to inhibit cytokine synthesis in human, ovine and murine monocytes (Wise et. al., *J Gen Virol* 88, 1677-1682, 2007; Fleming et al., *J Virol* 71, 4857-4861, 1997; Haig et al., *Virus Res* 88, 3-16, 2002; Imlach et al., *J Gen Virol* 83, 1049-1058, 2002), impairs the maturation of murine and human dendritic cells (Chan et al., *J Gen Virol* 87, 3177-3181, 2006, Lateef et al., *J Gen Virol* 84, 1101-1109, 2003,) but also costimulates mast cells and thymocytes (Fleming et al., *J Virol* 71, 4857-4861, 1997; Haig et al., *Virus Res* 88, 3-16, 2002; Imlach et al., *J Gen Virol* 83, 1049-1058, 2002).

Despite advances in the understanding of the principles underlying the wound healing process, there remains a significant unmet need for suitable therapeutic options for wound care and tissue repair and improving and/or promoting wound healing, including wounds that do not heal at expected rates, such as delayed-healing wounds, incompletely healing wounds, and compromised wound healing such as is seen in chronic wounds, scarring and abnormal or excessive scarring, including keloid and hypertrophic scarring, atropic scarring, widespread scarring, and scar contractures, as well as adhesions including surgical adhesions. There is a need in the art for improved methods and compositions for treating conditions such as those caused by acute and chronic wounds, inflammation, fibrosis, scarring, and adhesions.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

The invention generally relates to combinations of a viral vascular endothelial growth factor and an anti-inflammatory cytokine, including, for example, an anti-inflammatory interleukin.

In one embodiment, the invention includes a viral vascular endothelial growth factor and an anti-inflammatory cytokine administered together or in combination. In another embodiment, the invention provides a composition comprising a viral vascular endothelial growth factor and an anti-inflammatory cytokine, together with a pharmaceutically acceptable carrier. In one embodiment, amounts of the viral vascular endothelial growth factor and anti-inflammatory cytokine, in combination or for separate administration, are effective to promote wound healing and to treat wounds, in particular acute wounds and wounds that do not heal at expected rates, such as delayed-healing wounds, incompletely healing wounds, chronic wounds, and dehiscent wounds. In other embodiments, amounts of the viral vascular endothelial growth factor and anti-inflammatory cytokine, in combination or for separate administration, are effective to reduce fibrosis, adhesions, inflammation or scarring.

In one embodiment, the invention includes a viral vascular endothelial growth factor and a mammalian anti-inflammatory cytokine. In another embodiment, the invention includes a viral vascular endothelial growth factor and a mammalian anti-inflammatory interleukin. In yet another embodiment, the invention includes a viral vascular endothelial growth factor and a mammalian IL-10.

In one embodiment, the invention includes a viral vascular endothelial growth factor and a viral anti-inflammatory cytokine. In another embodiment, the invention includes a viral vascular endothelial growth factor and a viral anti-inflammatory interleukin. In yet another embodiment, the invention includes a viral vascular endothelial growth factor and a viral IL-10. In still another embodiment, the invention includes a viral vascular endothelial growth factor and a parapoxvirus IL-10. In another embodiment, the invention includes a viral vascular endothelial growth factor and an orf virus IL-10.

In one embodiment, the viral vascular endothelial growth factor is a VEGF-E. In another embodiment, the viral vascular endothelial growth factor is a parapoxvirus VEGF, e.g., a parapoxvirus VEGF-E. In still another embodiment, the viral vascular endothelial growth factor is an orf virus VEGF, e.g., an orf virus VEGF-E.

Thus, one example of the invention includes a VEGF-E and a viral IL-10 and, in one embodiment, one or both of the VEGF-E and the viral IL-10 are from the orf virus.

In one embodiment, the viral vascular endothelial growth factor and a viral interleukin may be used as a combination. In another embodiment, the viral vascular endothelial growth factor and a viral interleukin may be used separately in combination.

In another aspect, the invention includes a viral vascular endothelial growth factor and a viral interleukin in combination with a pharmaceutical carrier. In one embodiment, the invention comprises a VEGF-E and a viral IL-10 in combination with a pharmaceutical carrier. In one embodiment, one or both of the VEGF-E and the viral IL-10 are from the orf virus.

In another aspect, the invention includes a kit comprising a viral vascular endothelial growth factor and an anti-inflammatory cytokine (e.g., a viral interleukin) in combination with a pharmaceutical carrier, together with instructions for therapeutic application to a subject. In one embodiment, the viral vascular endothelial growth factor is VEGF-E and the viral interleukin is a viral IL-10. In another embodiment, one or both of the VEGF-E and the viral IL-10 are from a parapaoxvirus, e.g., the orf virus.

In another aspect, the invention includes a kit comprising a viral vascular endothelial growth factor in combination with a pharmaceutical carrier and an anti-inflammatory cytokine (e.g., a viral interleukin) in combination with a pharmaceutical carrier, together with instructions for therapeutic application to a subject. In one embodiment, the viral vascular endothelial growth factor is VEGF-E and the viral interleukin is a viral IL-10. In another embodiment, one or both of the VEGF-E and the viral IL-10 are from a parapaoxvirus, e.g, the orf virus.

The invention also relates to the use of a viral vascular endothelial growth factor and an anti-inflammatory cytokine (e.g., a viral interleukin) in the treatment of acute wounds, delayed-, impaired- and slow-healing wounds, chronic wounds, and dehiscent wounds. In one embodiment, a VEGF-E and a viral IL-10 are used for treatment. In another embodiment, one or both of the VEGF-E and the viral IL-10 are from a parapaoxvirus, e.g, the orf virus.

The invention also relates the use of a viral vascular endothelial growth factor and an anti-inflammatory cytokine (e.g., a viral interleukin) to reduce fibrosis in a subject. In one embodiment, a VEGF-E and a viral IL-10 are used to reduce fibrosis. In another embodiment, one or both of the VEGF-E and the viral IL-10 are from a parapaoxvirus, e.g, the orf virus.

The invention also relates the use of a viral vascular endothelial growth factor and an anti-inflammatory cytokine (e.g., a viral interleukin) to reduce adhesions, or the formation of adhesions, in a subject. In one embodiment, a VEGF-E and a viral IL-10 are used to reduce adhesions, or the formation of adhesions. In another embodiment, one or both of the VEGF-E and the viral IL-10 are from a parapaoxvirus, e.g., the orf virus.

The invention also relates the use of a viral vascular endothelial growth factor and an anti-inflammatory cytokine (e.g., a viral interleukin) to reduce inflammation in a subject. In one embodiment, a VEGF-E and a viral IL-10 are used to reduce inflammation. In another embodiment, one or both of the VEGF-E and the viral IL-10 are from a parapaoxvirus, e.g., the orf virus.

The invention also relates the use of a viral vascular endothelial growth factor and an anti-inflammatory cytokine (e.g., a viral interleukin) to reduce scarring in a subject. In one embodiment, a VEGF-E and a viral IL-10 are used to reduce scarring. In another embodiment, one or both of the VEGF-E and the viral IL-10 are from a parapaoxvirus, e.g., the orf virus.

In one aspect, a viral vascular endothelial growth factor and an anti-inflammatory cytokine (e.g., viral interleukin) are administered to a subject together. In one embodiment of this aspect, the viral vascular endothelial growth factor is a VEGF-E and the viral interleukin is a viral IL-10. In another embodiment of this aspect of the invention, one or both of the VEGF-E and the viral IL-10 are from a parapaoxvirus, e.g., the orf virus.

In another aspect, a VEGF-E and a viral IL-10 are administered to a subject separately. In one embodiment of this aspect, the viral vascular endothelial growth factor is a VEGF-E and the viral interleukin is a viral IL-10. In another embodiment of this aspect of the invention, one or both of the VEGF-E and the viral IL-10 are from a parapaoxvirus, e.g., the orf virus.

The invention also relates the use of a viral vascular endothelial growth factor and an anti-inflammatory cytokine (e.g., a viral interleukin) in combination with one or more other agents useful for wound healing, or for reducing inflammation, adhesions, fibrosis and/or scarring.

Examples of such other agents include anti-connexin agents, for example anti-connexin polynucleotides (for example, connexin inhibitors such as alpha-I connexin oligodeoxynucleotides), anti-connexin peptides (for example, antibodies and antibody binding fragments) and peptidomimetics (for example, alpha-I anti-connexin peptides or peptidomimetics), gap junction closing or blocking compounds, hemichannel closing or blocking compounds, and connexin carboxy-terminal polypeptides, e.g., polypeptides that bind to osteopontin or a osteopontin binding site, anti-osteopontin polynucleotides, as well as anti-ostepontin agents, particularly anti-osteopontin polynucleotides. Anti-osteopontin peptidomimetics may be administered per se, or complexed to one or more other agents, for example, antennapedia in order to facilitate membrane transport.

Compositions and methods of the invention that employ one or more viral vascular endothelial growth factors and one or more anti-inflammatory cytokine (e.g., viral interleukin) species for the treatment of, for example, acute, delayed healing, and chronic wounds are described and claimed. In certain embodiments, compositions include therapeutically useful compositions, particularly pharmaceutical or veterinary compositions that comprise one or more viral vascular endothelial growth factors and/or one or more anti-inflammatory cytokine (e.g., viral interleukin) species in amounts effective to promote healing or tissue repair in a subject. As a result, healing of an injury or wound can be initiated and/or enhanced, and inflammation, adhesions, fibrosis and/or scarring can be reduced.

In embodiments of the invention, the viral vascular endothelial growth factor is a parapox virus VEGF. In certain embodiments, the viral vascular endothelial growth factor is an orf virus VEGF.

In embodiments of the invention, the viral interleukin species include viral IL-10. In other embodiments, the viral IL-10 is a parapox virus IL-10. In one embodiment, the viral IL-10 is an orf virus IL-10.

The methods, compositions and kits of the invention include, for example, injected, topical and inhaled delivery forms and formulations. Such delivery forms and formulations include those for the treatment of a subject, as described herein.

Pharmaceutical compositions are also provided in the form of a combined preparation, for example, as an admixture of one or more viral vascular endothelial growth factors and one or more anti-inflammatory cytokine (e.g., viral interleukin) species, alone, in conjunction or in combination with and one or more therapeutic agents, for example, one or more anti-connexin or anti-osteopontin agents, including anti-connexin and anti-osteopontin polynucleotides, peptide, and or peptidomimetic species.

The term "a combined preparation" includes a "kit of parts" in the sense that the combination partners as defined herein can be dosed independently or by use of different fixed combinations with distinguished amounts of the two or more agent species, i.e. simultaneously, separately or sequentially. The parts of the kit can then, for example, be administered simultaneously or chronologically staggered, that is, at different time points, with equal or different time intervals, and/or in the same or different numbers of dosings for any part of the kit of parts.

In some embodiments, a combined preparation is administered, wherein two or more separate compositions are administered to a subject, wherein the first composition comprises a therapeutically effective amount of one or more viral vascular endothelial growth factors and the second composition comprises a therapeutically effective amount of and one or more anti-inflammatory cytokine (e.g., viral interleukin) species. In other embodiments, a third composition is administered comprising one or more anti-connexin or anti-osteopontin polynucleotides, peptides, or peptidomimetics. In one embodiment, the anti-connexin agent is an anti-connexin43 agent.

Pharmaceutical compositions are provided for combined, simultaneous, separate, sequential, or sustained administration. In some embodiments, a composition comprising one or more viral vascular endothelial growth factors and/or one or more anti-inflammatory cytokine (e.g., viral interleukin) species is administered at or about the same time as one or more anti-connexin agents and/or anti-osteopontin agents. In one embodiment, a composition comprising one or more viral vascular endothelial growth factors and/or one or more anti-inflammatory cytokine (e.g., viral interleukin) species is administered within at least about 30, 60, 90, or 120 minutes, or about 3, 4, 5, 6, 8, 12, 24, 48, or 168 hours of one or more anti-connexin agents and/or anti-osteopontin agents.

In one aspect, the invention includes pharmaceutical compositions, including injectable, topical, systemic, and inhaled delivery forms and formulations, comprising a pharmaceutically acceptable carrier and therapeutically effective amounts of one or more viral vascular endothelial growth factors and/or one or more anti-inflammatory cytokine (e.g., viral interleukin) species, alone or together or in combination with one or more other therapeutic agent species, e.g., a first anti-connexin agent species, a second anti-connexin agent species, a first anti-osteopontin agent species, and/or and a second anti-osteopontin agent species. Such compositions are useful, for example, for wound healing, and other applications as described herein.

Examples of viral vascular endothelial growth factors include parapoxvirus VEGFs, as well as VEGFs from all orf virus strains that encode a VEGF-E (e.g., NZ2, NZ10, NZ7, D1701 and so on). Parapoxvirus VEGFs include VEGFs from parapoxvirus strains BPSV, PVNZ and PCPV, and all other strains that encode a VEGF-E. VEGFs from other viral species are included within the scope of the present inventions. In other embodiments, the viral VEGF can be any molecule, whether naturally occurring or non-naturally occurring (including derivatives or variants of a naturally occurring molecule designed or discovered (e.g., through random or directed mutagenesis)), that activates VEGFR-2 more than the VEGFR-1. In other embodiments, the viral VEGF can be any molecule, whether naturally occurring or non-naturally occurring (including derivatives or variants of a naturally occurring molecule designed or discovered (e.g., through random or directed mutagenesis)), that activates VEGFR-2 but does not appreciably bind to or activate VEGFR-1.

Examples of viral interleukin species include viral interleukins from orf viruses, EBVs, CMVs, including IL-10s from these and other viruses. Viral interleukins include poxvirus IL-17 homologues, the EBV CXCR homolog, and the KSHV Il-6 homolog and IL-8R homologue. These and all other viral interleukins with anti-inflammatory activity are within the scope of the invention. Poxviruses also have anti-inflammatory chemokine mimics, interleukin/TNF/chemokine binding proteins and other IL-119/20/22-like proteins. All such proteins having anti-inflammatory activity are within the scope of the present inventions.

Examples of anti-connexin and anti-ostepontin agents are polynucleotides, including antisense oligodeoxynucleotides. Examples of anti-connexin and anti-ostepontin polynucleotides include anti-connexin and anti-ostepontin oligodeoxynucleotides, including antisense (including modified and unmodified backbone antisense), RNAi, and miRNA and siRNA. Suitable anti-connexin peptides include peptides that bind connexin extracellular domains, for example, or connexin intracellular domains. Peptidomimetics may be complexed to one or more other agents, for example, antennapedia in order to facilitate membrane transport for binding to intracellular connexin regions and domains.

The present invention provides for an increase in the rate, extent, and/or quality of wound healing through the use of at least one viral vascular endothelial growth factor and at least one anti-inflammatory cytokine (e.g., viral interleukin) (alone or in combination with one or more therapeutic agent species) administered simultaneously, separately, or sequentially, or administered in combination.

The present invention provides for a decrease in inflammation through the use of at least one viral vascular endothelial growth factor and at least one anti-inflammatory cytokine (e.g., viral interleukin) (alone or in combination with one or more therapeutic agent species) administered simultaneously, separately, or sequentially, or administered in combination.

The present invention provides for a decrease in scarring and/or an increased quality of scar through the use of at least one viral vascular endothelial growth factor and at least one anti-inflammatory cytokine (e.g., viral interleukin) (alone or in combination with one or more therapeutic agent species) administered simultaneously, separately, or sequentially, or administered in combination.

In certain embodiments, the combined use of an at least one viral vascular endothelial growth factor and at least one anti-inflammatory cytokine (e.g., viral interleukin) administered simultaneously, separately, or sequentially, or in combination will have fewer administration time points and/or increased time intervals between administrations as a result of such combined use. In other such embodiments, the combined use allows a reduced frequency of administration. In other embodiments, combined use allows the use of reduced doses of such agents compared to the dose or doses that may be effective when the agent is administered alone.

In certain other embodiments, the combined use of an at least one viral vascular endothelial growth factor and at least one anti-inflammatory cytokine (e.g., viral interleukin) administered simultaneously, separately, or sequentially, or in combination with one or more other therapeutic agents, for example, one or more anti-connexin polynucleotides, peptides, or peptidomimetics and/or one or more anti-osteopontin polynucleotides, peptides, or peptidomimetics has an additive, synergistic, or super-additive effect in the promotion of the desired therapeutic outcome, for example, wound healing and for reduced inflammation, fibrosis, adhesion formation and scarring. In some of these embodiments, the administration of a combined preparation will have fewer administration time points and/or increased time intervals between administrations as a result of such combined use. In other such embodiments, the combined use allows a reduced frequency of administration. In other embodiments, combined use allows the use of reduced doses of such agents compared to the dose or doses that may be effective when the agent is administered alone.

In another aspect, the invention includes methods for administering a therapeutically effective amount of at least one viral vascular endothelial growth factor and at least one anti-inflammatory cytokine (e.g., viral interleukin) administered simultaneously, separately, or sequentially, or in combination. In some embodiments, the compositions are formulated, for example, in a delayed release preparation, a slow release preparation, an extended release preparation, a controlled release preparation, and/or in a repeat action preparation suitable for administration to a subject having a wound, including chronic wounds and wounds characterized in whole or in part by slow, delayed, or incomplete wound healing. Chronic wounds include diabetic ulcers (e.g., diabetic foot ulcers), venous ulcers, venous stasis ulcers, pressure ulcers, decubitus ulcers, vasculitic ulcers, arterial ulcers, infectious ulcers, burn ulcers, trauma-induced ulcers, inflammatory ulcers, and ulcerations associated with pyoderma gangrenosum. Chronic wounds also include ocular ulcers, including persistent epithelial defects. In some embodiments, the subject is diabetic; in others, the subject has a cardiovascular disease or condition, for example, venous hypertension, venous insufficiency and/or arterial insufficiency.

In certain other aspects, the invention relates to methods of using the compounds and compositions of the invention to treat subjects suffering from or at risk for various diseases, disorders, and conditions associated with a wound, including acute wounds and wounds that do not heal at expected rates, including delayed healing and chronic wounds. Treatment of a subject, e.g., for a wound or other indication as indicated herein, with one or more pharmaceutical compositions of the invention, may comprise their simultaneous, separate, sequential or sustained administration.

In yet another aspect, the invention includes methods for treating a subject having or suspected of having or predisposed to, or at risk for, any diseases, disorders and/or conditions characterized in whole or in part by a wound or a tissue in need of repair. Such compositions include, for example, topical and inhaled delivery forms and formulations.

In another aspect, the invention provides methods of treatment comprising administering to a subject a pharmaceutical composition of the invention in one or more therapeutically effective amounts for use in the treatment of a wound, including for example, acute, as well as wounds that do not heal at expected rates, including delayed healing and chronic wounds.

In another aspect, the invention provides methods of treatment comprising administering to a subject in need thereof a composition comprising therapeutically effective amounts of at least one viral vascular endothelial growth factor and at least one anti-inflammatory cytokine (e.g., viral interleukin) administered simultaneously, separately, or sequentially, or in combination, alone or in combination with one or more anti-connexin and/or anti-osteopontin agents. Also within the scope of the present invention is pretreatment prior to surgery. This will reduce local damage at points of incision, excision or revision, for example, and prime cells for healing.

In yet another aspect, the invention provides methods of treatment comprising administering to a subject in need thereof a first composition and at least one other therapeutic composition (e.g., a second composition, second and third compositions, etc.) comprising at least one viral vascular endothelial growth factor and at least one anti-inflammatory cytokine (e.g., viral interleukin). In embodiments of this aspect, the "first" composition comprises a therapeutically effective amount of at least one viral vascular endothelial growth factor and/or at least one anti-inflammatory cytokine (e.g., viral interleukin) administered simultaneously, separately, or sequentially, or in combination, although this is not meant to imply that such composition is administered before, more frequently, or via a different route than the other therapeutic composition(s). In other words, in some of these embodiments, the first composition is administered first, while in others, the second composition is administered first.

In embodiments involving the administration of three different therapeutic compositions, such methods, for example, can comprise simultaneous administration of each of the compositions according to the same or different dosing or administration regimen.

In a further aspect, the invention provides methods for improving or reducing scar formation in a subject in need thereof, for improving or reducing fibrosis in a subject, and for improving or reducing adhesion formation in a subject, comprising administering to said subject a therapeutically effective amount of a pharmaceutical composition comprising an at least one viral vascular endothelial growth factor and at least one anti-inflammatory cytokine (e.g., viral interleukin) administered simultaneously, separately, or sequentially, or in combination, alone or in combination with one or more other therapeutic agents.

In certain embodiments methods of combination therapy include the administration of at least one viral vascular endothelial growth factor and at least one anti-inflammatory cytokine (e.g., viral interleukin) administered simultaneously, separately, or sequentially, or in combination, either some, or all of which are provided in amounts or doses that are less than those used when the agent or agents is/are administered alone, i.e., when they are not administered in combination, either physically or in the course of treatment of a wound or other condition to be improved. Such lesser amounts of agents administered are typically from about one-half, one-third, one-fourth, one-fifth, one-sixth, one-eighth, one-tenth, or about one-twentieth the amount when administered alone.

In a further aspect, the invention includes transdermal patches, dressings, pads, wraps, matrices, and bandages capable of being adhered or otherwise associated with the skin of a subject, said articles being capable of delivering a therapeutically effective amount of an at least one viral vascular endothelial growth factor and at least one anti-inflammatory cytokine (e.g., viral interleukin) administered simultaneously, separately, or sequentially, or in combination, alone or in combination with one or more therapeutic agents, to a subject.

In another aspect, the invention includes an article of manufacture comprising a vessel or vessels containing a therapeutically effective amount of an at least one viral vascular endothelial growth factor and at least one anti-inflammatory cytokine (e.g., viral interleukin) for administration simultaneously, separately, or sequentially, or in combination (alone or in combination with one or more other therapeutic agents), and instructions for use, including use for the treatment of a subject.

The invention includes an article of manufacture comprising packaging material containing one or more dosage forms containing at least one viral vascular endothelial growth factor and at least one anti-inflammatory cytokine (e.g., viral interleukin) administered simultaneously, separately, or sequentially, or in combination, alone or together with dosage forms containing one or more other therapeutic agents, wherein the packaging material has a label that indicates that the dosage form can be used for a subject having or suspected of having or predisposed to any of the diseases, disorders and/or conditions described or referenced herein, including diseases, disorders and/or conditions characterized in whole or in part by acute, impaired, delayed or chronic wound healing, by inflammation, by scarring, by fibrosis, or by adhesions. Such dosage forms include, for example, topical delivery forms and formulations, powdered delivery forms and formulations, delivery forms and formulations suitable for injection or infusion (including dry or powdered compositions that must be reconstituted with a suitable diluent prior to administration), and delivery forms and formulations suitable for instillation. Suitable formulations deliver an amount of a therapeutic agent suitable to achieve a desired therapeutic effect. Examples of topical formulations include foams, sprays, and gels. Examples of gels include polyoxyethylene-polyoxypropylene copolymer-based gels and carboxymethylcellulose-based and related cellulose gels, as well as alginate gels, with pluronic gels being particularly useful.

The invention also includes methods for the use of therapeutically effective amounts of compositions of the invention in the manufacture of medicaments, including, for example, topical delivery forms and formulations. Such medicaments include those for the treatment of a subject as described herein, including for the treatment of acute wounds, delayed, impaired- and slow healing wounds, chronic wounds and dehiscent wounds.

In another aspect, the invention provides for the use of at least one viral vascular endothelial growth factor and at least one anti-inflammatory cytokine (e.g., viral interleukin) to be administered simultaneously, separately, or sequentially, or in combination in the manufacture of pharmaceutical products for the promotion of wound healing, improved and/or reduced scarring, improved and/or reduced inflammation, reduced fibrosis, or reduced adhesion formation in a patient in need thereof. In some of these embodiments, the product includes a wound dressing or wound healing promoting matrix. For example, the wound dressing or matrix is provided in the form of a solid substrate with a composition comprising an at least one viral vascular endothelial growth factor and at least one anti-inflammatory cytokine (e.g., viral interleukin) dispersed on or in the solid substrate.

In yet another embodiment, the invention provides for the use of compounds and compositions of the invention in conjunction or in combination with connective tissue growth factor (CTGF) inhibitors, e.g., CTGF antisense compounds. In another embodiment, the invention provides for the use of compounds and compositions of the invention in conjunction or in combination with PDGF receptor inhibitors to, for example, treat fibrosis and/or to reduce adhesions and scar formation. PDGF receptor inhibitors include, for example, receptor blockers, receptor antagonists. CTGF and PDGF receptor inhibitors also include monoclonal antibodies, polyclonal antibodies, antibody fragments (including, for example, Fab, F(ab')$_2$ and Fv fragments; single chain antibodies; single chain Fvs; and single chain binding molecules such as those comprising, for example, a binding domain, hinge, CH2 and CH3 domains, recombinant antibodies and antibody fragments which are capable of binding an antigenic determinant (e.g., an epitope) that makes contact with a particular antibody or other binding molecule, including antibodies and antibody binding fragments directed against CTGF or PDGF receptors. In another embodiment, the invention provides for the use of compounds and compositions of the invention in conjunction or in combination or in combination with PDGF receptor agonists to, for example, treat wounds.

In yet another embodiment, the invention provides for the use of compounds and compositions of the invention in conjunction or in combination with the application of artificial skin products, including, for example Dermagraft® (a single-layered cryopreserved dermal substitute composed of human fibroblasts, extracellular surrounding substance and a bioabsorbable framework), Apligraf® (living, bilayered skin construct with an epidermal layer formed by human keratinocytes and a dermal layer composed of human fibroblasts in a bovine Type 1 collagen web), Integra® (two-layer membrane system for skin replacement comprising a dermal replacement layer made of a porous template of fibers of bovine tendon collagen and glycosaminoglycan (chondroitin-6-sulfate) and an epidermal substitute layer made of thin silicone to control moisture loss), AlloDerm® (acellular dermal matrix), Cyzact™ (human dermal fibroblasts delivered via a fibrin), ICX-SKN (a combination of fibroblasts and fibrin matrix that are remodeled to produce a collagen matrix), Keragraft™ (a human stem cell-derived product being developed for wound care as an autologous epidermal equivalent), OASIS® Wound Matrix (biologically derived extracellular matrix-based wound product created from porcine-derived acellular small intestine submucosal), OrCel™ (two-layer cellular template in which human epidermal keratinocytes and dermal fibroblasts are cultured in two separate layers onto a bovine collagen sponge), TransCyte® (human fibroblast-derived temporary skin substitute consisting of a polymer membrane and neonatal human fibroblast cells), and so on. The compounds and compositions of the invention are also useful in conjunction or in combination with the application of other dressings to promote wound healing, including, for example, BioBrane. The compounds and compositions of the invention may also be used in conjunction or in combination with the application of other types of scaffolds or dressings to promote wound healing, including, for example, spray on cells being developed by HealthPoint (a cell therapy spray suspension known as HP802-247, which consists of two components that are sprayed sequentially on the wound bed at the time of treatment: a fibrinogen solution and a cell preparation containing a mixture of growth arrested, living, allogeneic epidermal keratinocytes and dermal fibroblasts) and cultured allogenic keratinocytes.

The inventions also relate to the use of an anti-osteopontin agent, including peptides and peptidomimetics, for example an anti-osteopontin polynucleotide species, alone or in combination with one or more other agents useful in the treatment of acute, delayed healing and chronic wounds.

These and other aspects of the present inventions, which are not limited to or by the information in this Brief Summary, are provided below.

BRIEF DESCRIPTION OF THE FIGURES

A brief summary of each of the figures is provided below.

DETAILED DESCRIPTION

As indicated in the Brief Summary and described in detail herein, the inventions relate to the use of a viral VEGF with regenerative properties and an anti-inflammatory viral interleukin in combination for accelerating/improving wound healing while reducing scarring and inflammation. In one embodiment, the viral VEGF is VEGF-E and viral interleukin is IL-10. For example, a VEGF-E and a viral IL-10 from the orf virus may be used. Various Examples show the surprising attributes of a combination of treatment with a viral VEGF with regenerative properties and with an anti-inflammatory viral interleukin.

Figure 1:
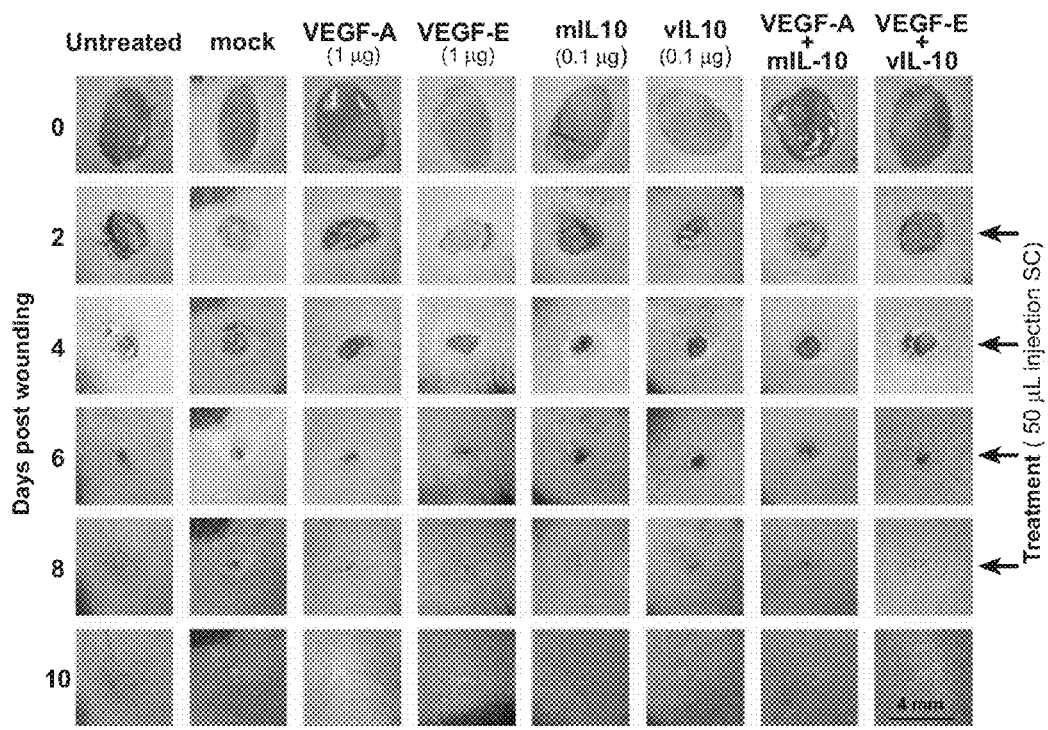
FIG. 1. Combination treatment of viral VEGF-E and viral IL-10 accelerates cutaneous tissue repair to a greater extent than the individual treatments or their mammalian equivalents. (A) Photographs of the healing process of 4 mm dermal full-thickness punch wounds at the time points indicated during treatment with different viral and mammalian factors. Timing of treatments is indicated on the right. (B) Kinetics of skin wound closure in groups of mice with local administration of the indicated viral and mammalian factors to the wound site (n=8 per group). Values significantly less than mock-treated wounds ($P \leq 0.05$) are indicated by an asterisk. Significant differences, between comparative treatments at given time points, are indicated with a hash.
Figure 1:
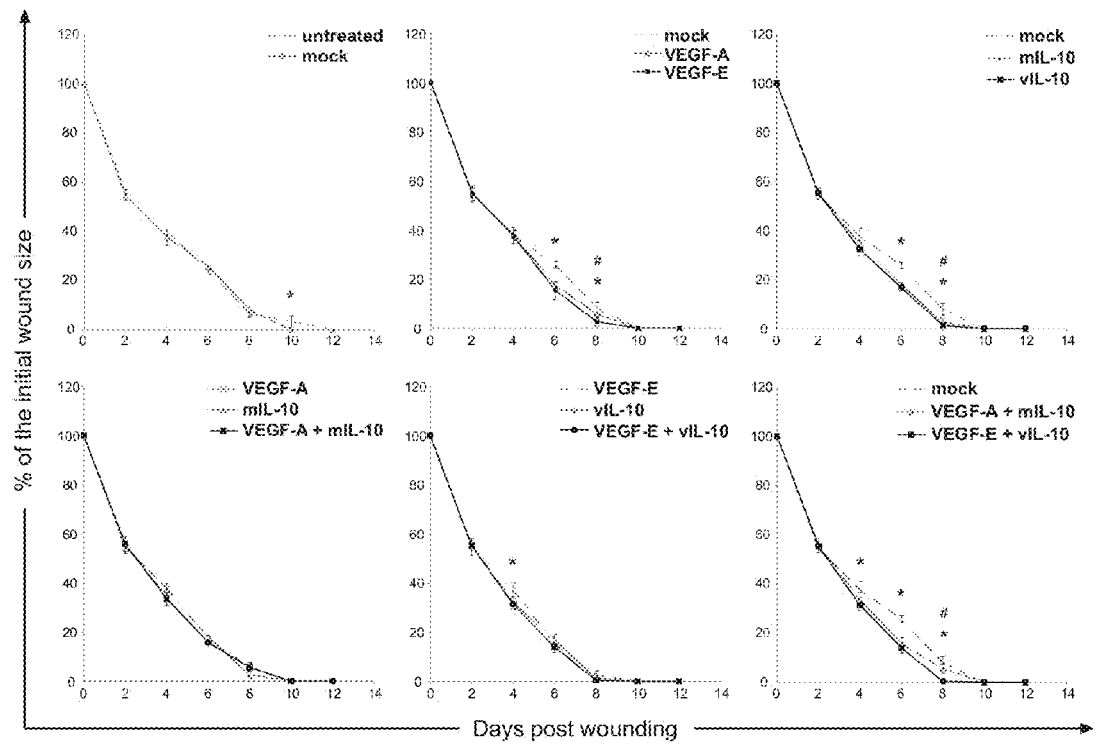
Figure 3:
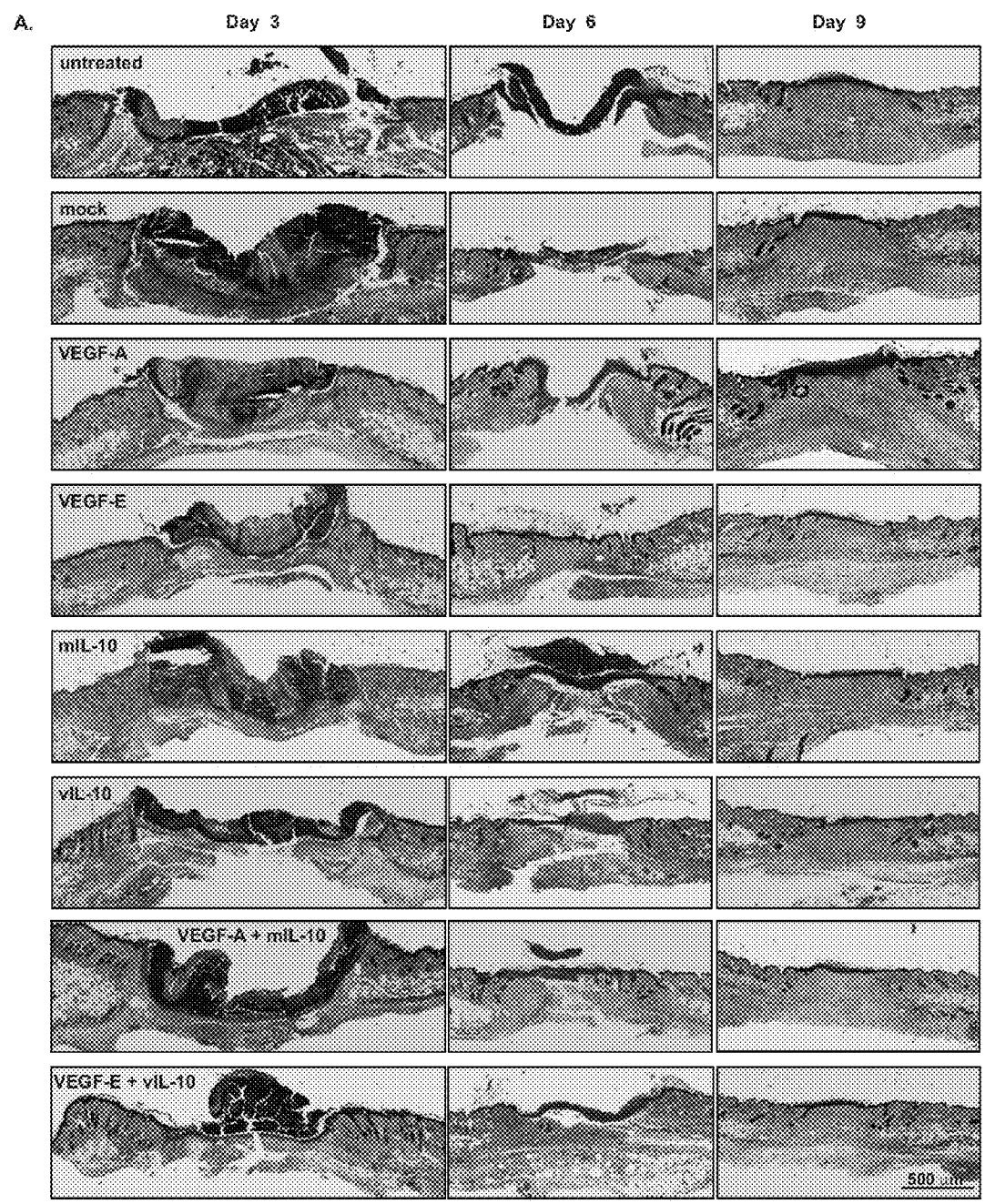
FIG. 3. Combination treatment of VEGF and IL-10 enhances epidermal regeneration to a greater extent than the individual treatments. (A) Epidermal regeneration was examined in wounded skin treated with different viral and mammalian factors. Skin biopsies taken at days 3, 6 and 9 were fixed in zinc salts solution and paraffin-embedded, then 4 μm sections were stained with MSB trichrome and photographed. Scale is indicated. (B) A schematic of a wound section with histological features labeled. Re-epithelialisation in each section is calculated as the percentage of total wound width covered by neo-epidermis as indicated. (C) The rate of wound re-epithelialisation was quantitated in 6 serial sections from 2 wounds from each of 4 mice using ImageJ and is expressed as the mean+/−SE. (D) The area (2/section) of the neo-epidermis is expressed as the mean+/−E. Values significantly greater than that of untreated skin ($P \leq 0.05$) are indicated by an asterisk. Significant differences between individual mammalian and viral treatments or between individual and combination treatments or between mammalian and viral combination treatments are indicated with a hash.
Figure 3:
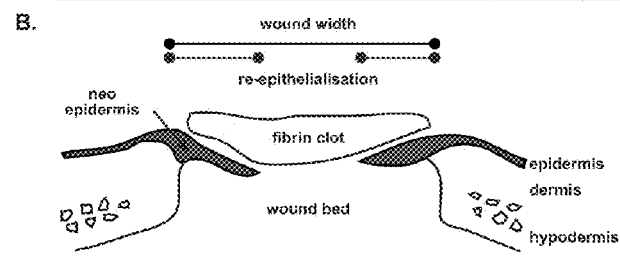
Figure 3:
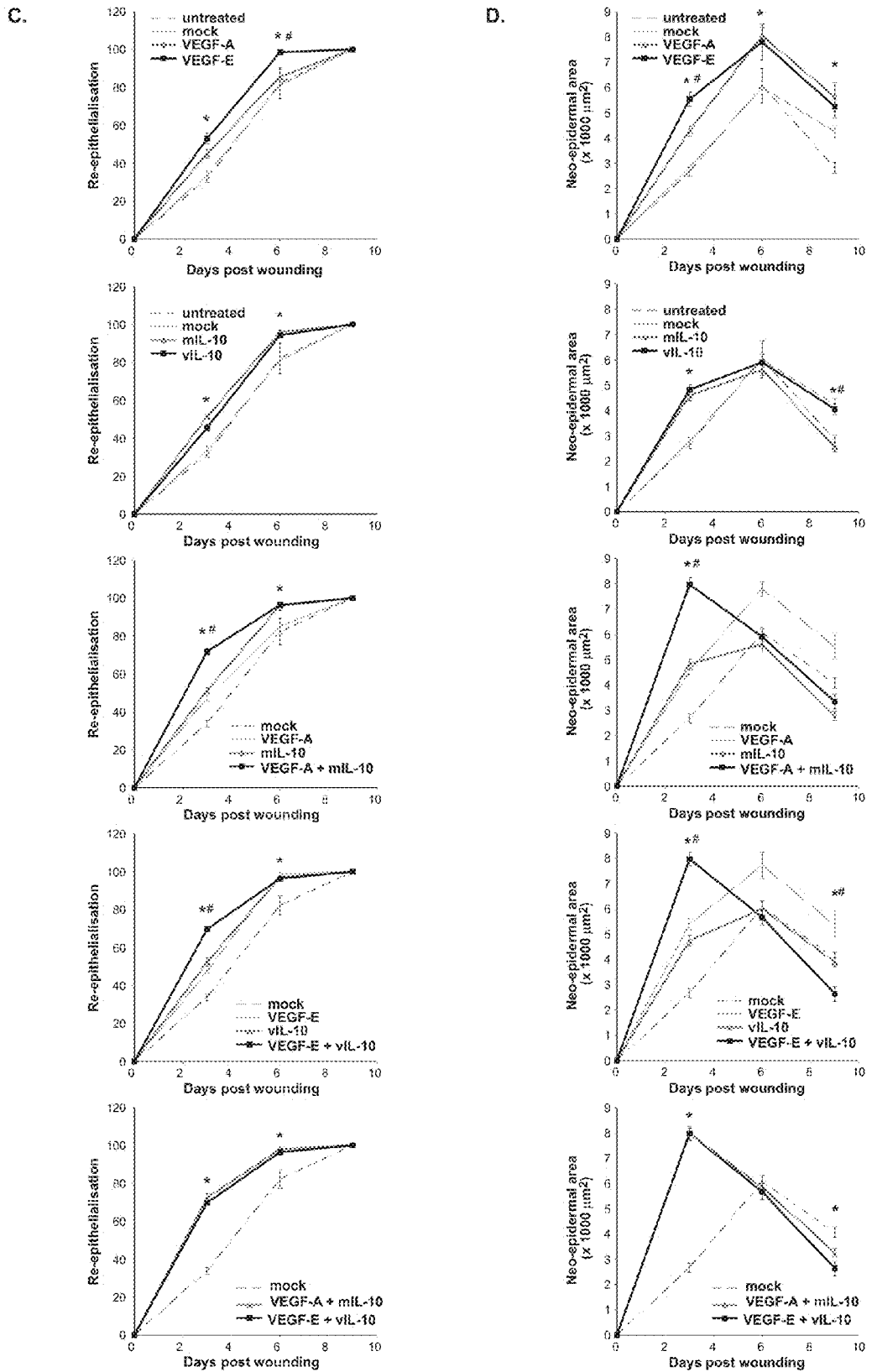
Figure 4:
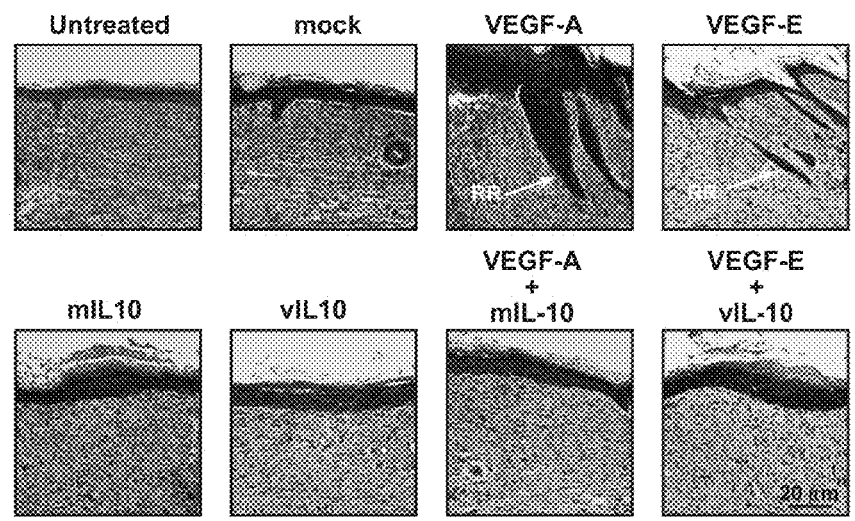
FIG. 4. Combination treatment of VEGF and IL-10 promotes epidermal resolution to a greater extent than the individual VEGF treatments. (A) Epidermal resolution was examined in wounded skin treated with different viral and mammalian factors. Zinc-fixed, paraffin-embedded skin sections from wound biopsies taken on day 9 were stained with MSB trichrome and photographed. Scale is indicated in the bottom right panel and examples of rete ridges (RR) are labeled. Changes in rete ridge formation were quantitated in 6 serial sections from 2 wounds from each of 4 mice using ImageJ. (B) The length of rete ridges projecting from the neo-epidermis is expressed as the mean+/−SE. Values significantly greater than that of untreated or mock-treated skin ($P \leq 0.05$) are indicated by an asterisk or hash, respectively.
Figure 4:
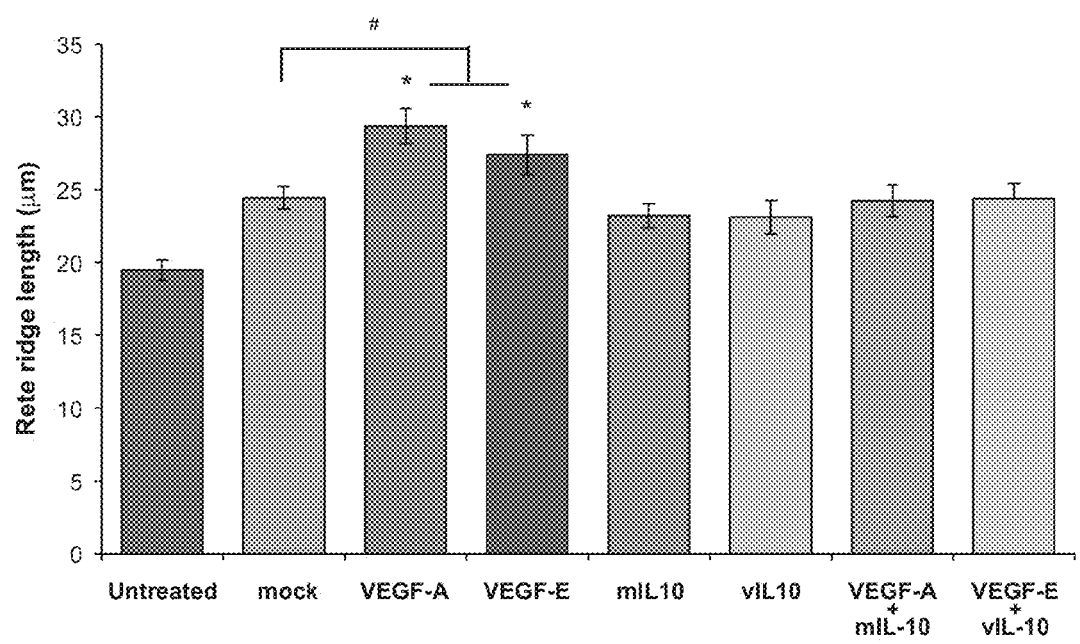
Figure 5:
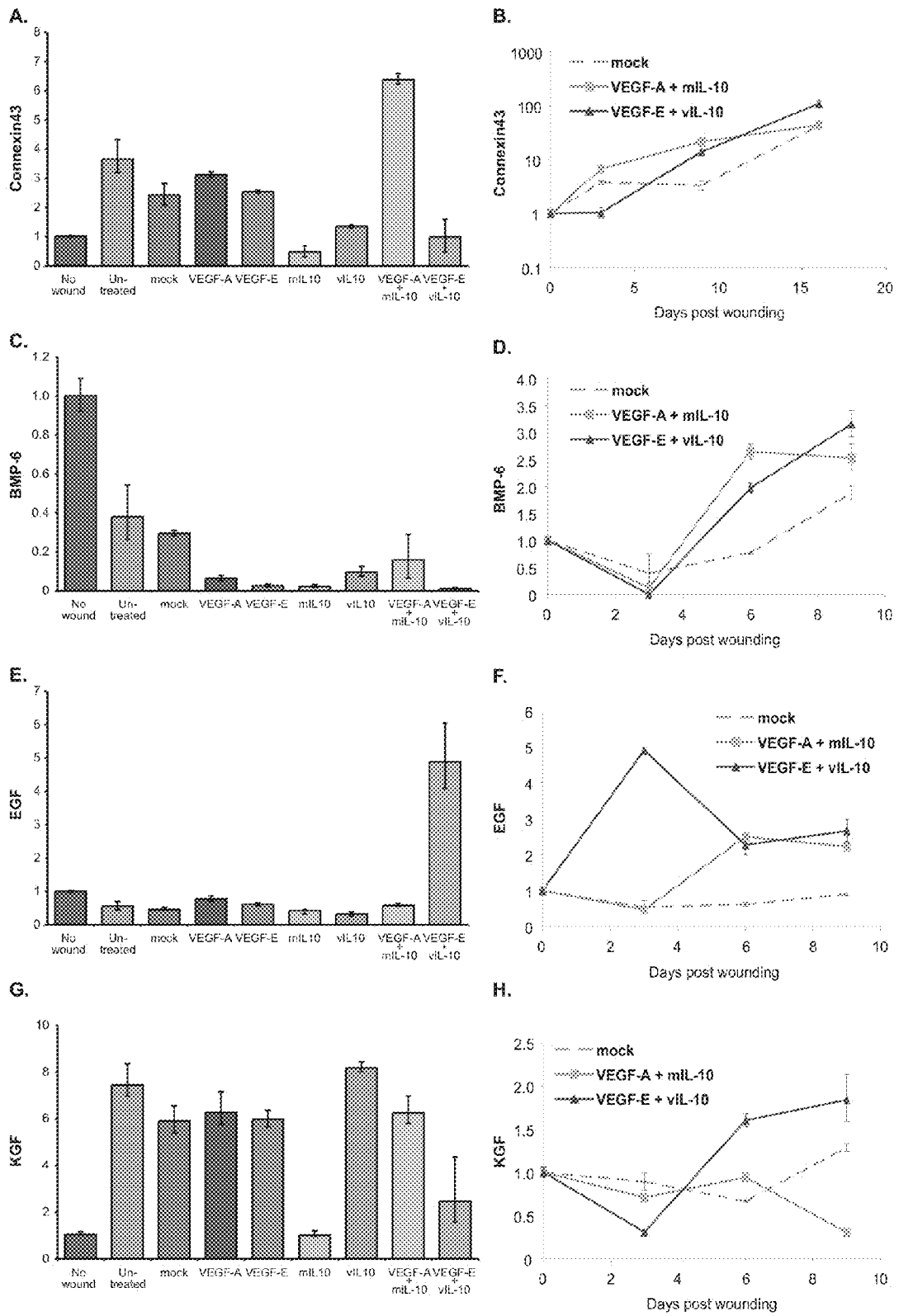
FIG. 5. Combination treatment of viral VEGF and IL-10 promotes epidermal resolution by altering the timing and level of key regulators of epidermal repair. The expression of key epidermal regulators in wounded skin treated with different viral and mammalian factors was examined over time using quantitative RT-PCR. cDNA was prepared by reverse transcription of total RNA (4 left flank wounds combined/treatment group). The level of (A) connexin43, (C) BMP-6, (E) EGF and (G) KGF mRNA, for all treatments, three days post wounding, are shown in the left panel. The levels of (B) connexin43, (D) BMP-6, (F) EGF and (H) KGF mRNA, for combination treatments, over the course of healing, are shown in the right panel. All mRNA levels are relative to the levels of GAPDH and unwounded skin. Values represent the mean±SE (n=3) and were consistent with values determined when the procedure was repeated with the 4 right flank wounds from each treatment group.

In Example 2, a combination treatment of viral VEGF-E and viral IL-10 reduces wound size to a greater extent than the individual viral treatments or the cellular combination (see FIG. 1). It also demonstrates that the combination treatment of viral VEGF-E and viral IL-10 enhances wound closure to a greater extent than the mammalian (also referred to as the "cellular") combination (see FIG. 2). As shown in Examples 3 and 5, a combination treatment of viral VEGF-E and viral IL-10 also enhances epidermal regeneration to a greater extent than the individual treatments (see FIGS. 3 and 5). Examples 4 and 5, additionally, demonstrate that a combination treatment of viral VEGF-E and viral IL-10 prevents the epidermal hyperplasia induced by VEGF treatment alone (see FIGS. 4 and 5).

Figure 6:
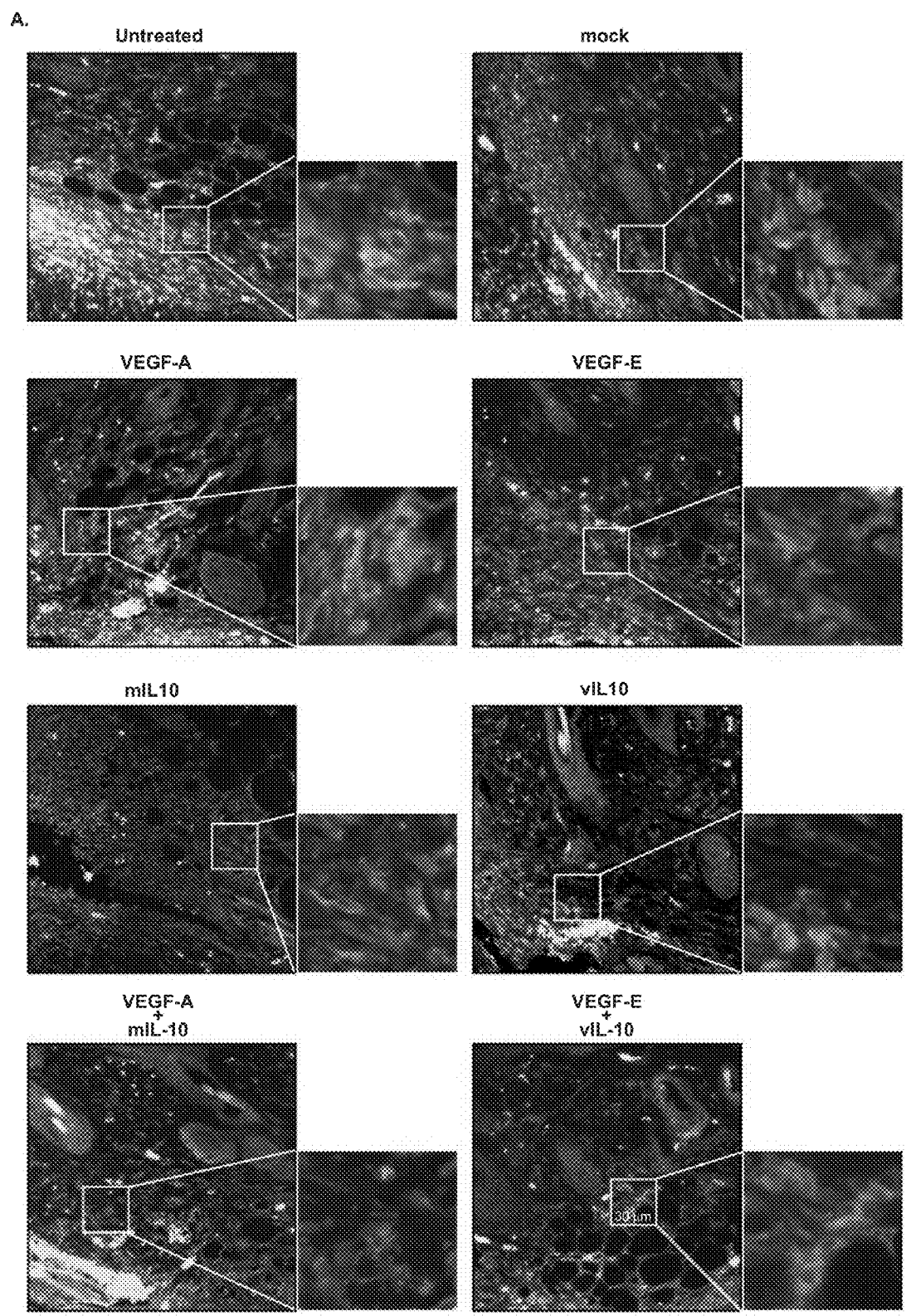
FIG. 6. Combination treatment of VEGF and IL-10 reduces inflammatory cell recruitment into the wound to a similar extent as individual IL-10 treatments. (A) Zinc-fixed, paraffin-embedded skin sections from wound biopsies taken on day 6 were stained for the macrophage marker F4/80 (green staining; blue, nuclear staining). Representative images are shown of wounded skin treated with different viral and mammalian factors. Scale is indicated in the bottom right panel and examples of F4/80+ve cells are enlarged. (B) The number of inflammatory cells within 0.57 mm of the wound edge was quantified from 2 wounds from each of 4 mice. Values are expressed as the mean F4/80+ve macrophages per 1000 $mm^2 \pm SE$. Values significantly below that of untreated wounds are indicated by an asterisk ($P \leq 0.05$).
Figure 6:
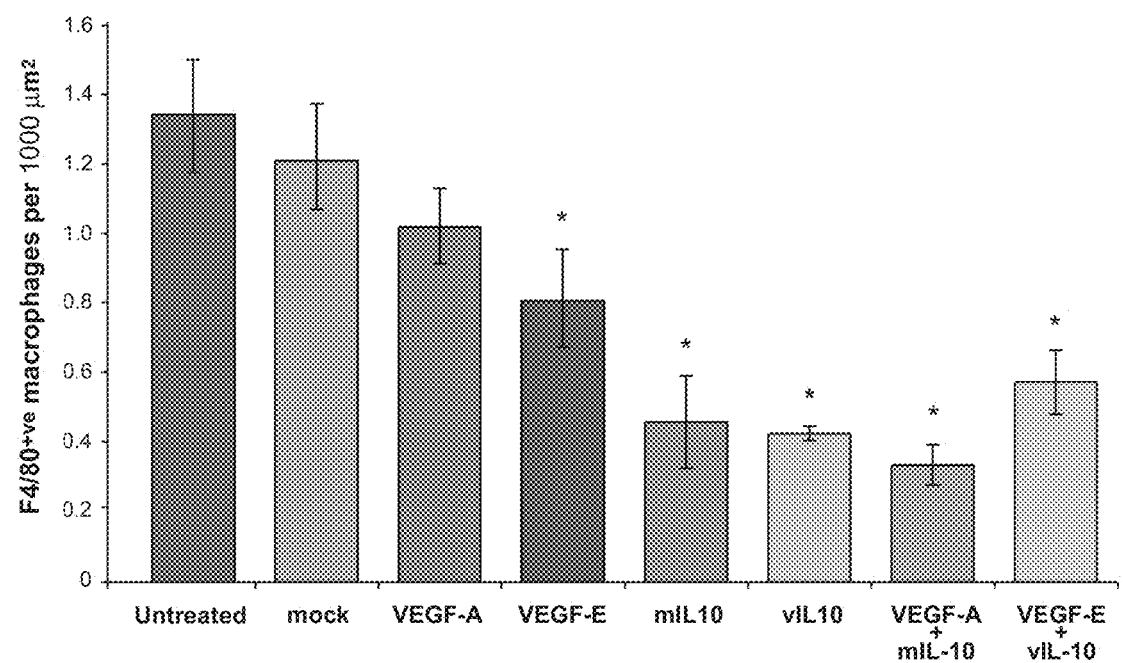
Figure 7:
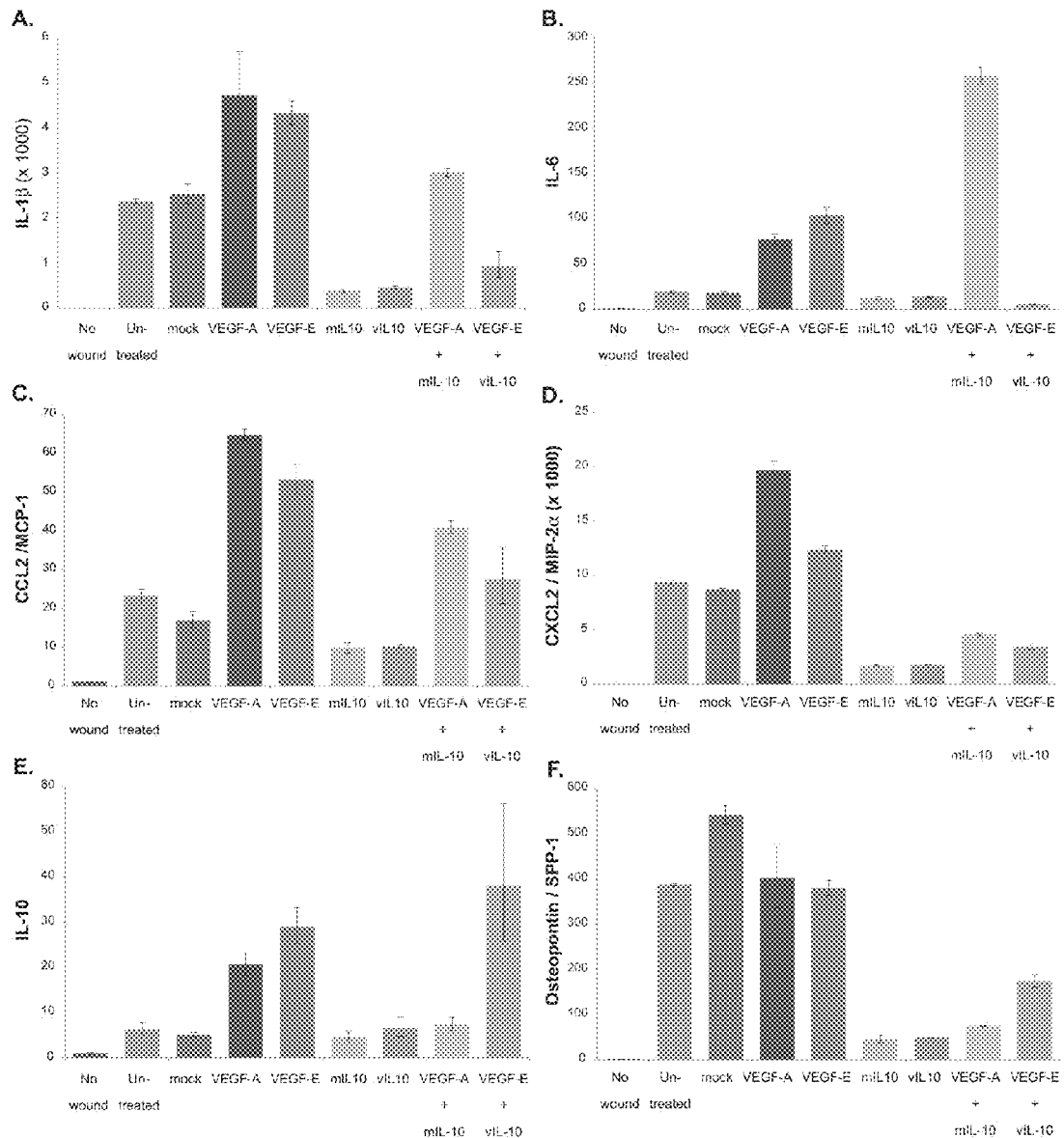
FIG. 7. Combination treatment of viral VEGF and IL-10 reduces wound inflammation by altering the timing and level of key regulators of inflammatory cell migration and activation. The expression of key inflammatory regulators in wounded skin treated with different viral and mammalian factors was examined over time using quantitative RT-PCR. cDNA was prepared by reverse transcription of total RNA (4 left flank wounds combined/treatment group). The level of (A) IL-1β, (B) IL-6, (C) CCL2/MCP-1, (D) CXCL2/MIP-2α, (E) IL-10, and (F) Osteopontin/SPP-1 mRNA are shown for all treatments three days post wounding. All mRNA levels are relative to the levels of GAPDH and unwounded skin. Values represent the mean±SE (n=3) and were consistent with values determined when the procedure was repeated with the 4 right flank wounds from each treatment group.
Figure 8:
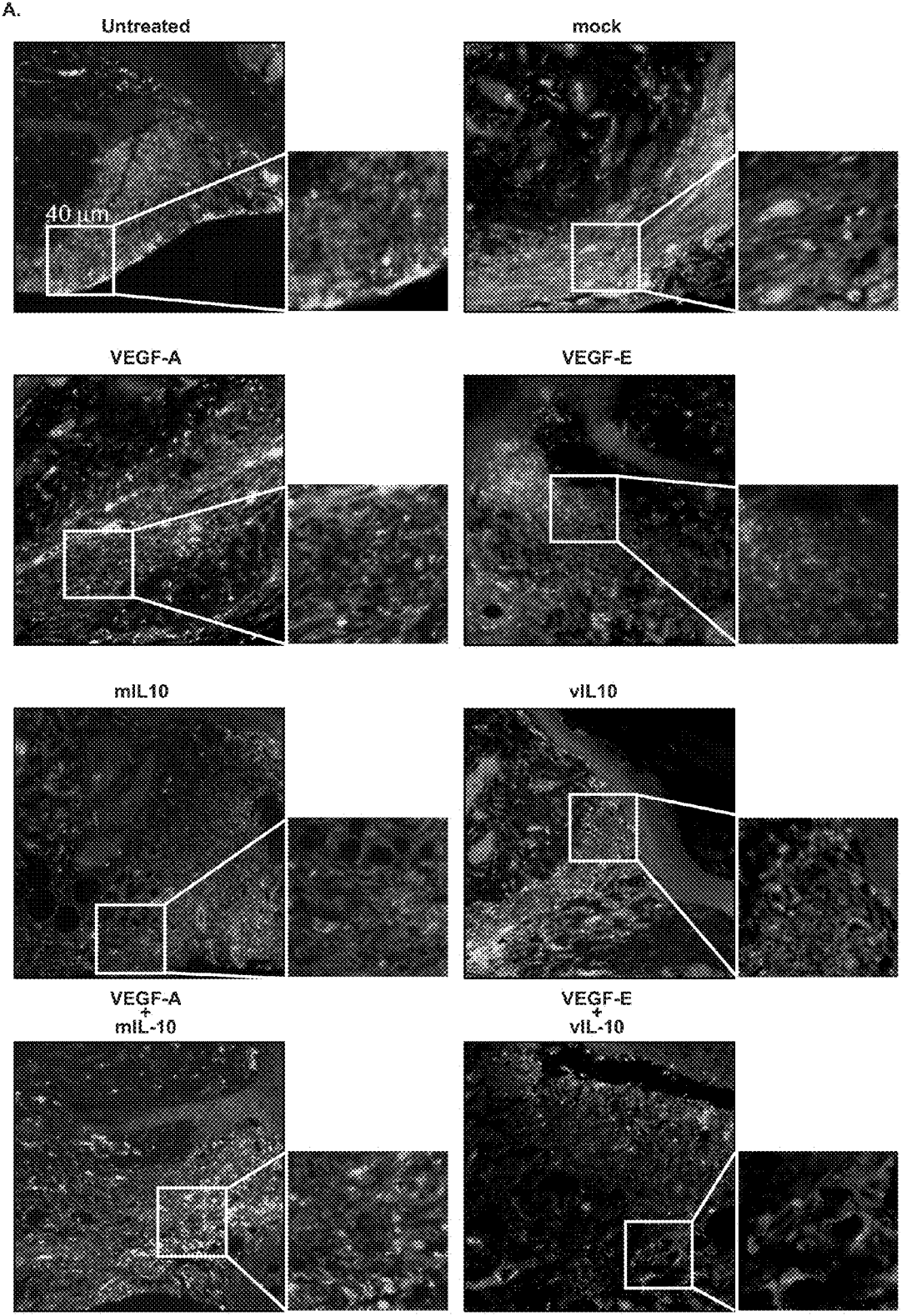
FIG. 8. Combination treatment of VEGF and IL-10 reduces myofibroblast differentiation. The addition of VEGF to its respective IL-10 did not diminish the ability of the viral or mammalian IL-10 to reduce myofibroblast differentiation. (A) Zinc-fixed, paraffin-embedded skin sections from wound biopsies taken on day 6 were stained for the fibroblast marker vimentin (green staining) and the myofibroblast marker αSMA (red staining; blue, nuclear staining). Representative images are shown of wounded skin treated with different viral and mammalian factors. Scale is indicated and examples of stained cells are enlarged. (B) The intensity of red αSMA staining within the granulation tissue was quantified from two wounds from each of 4 mice. Values are expressed as the total αSMA intensity±SE. Values significantly below that of untreated wounds are indicated by an asterisk ($P \leq 0.05$).
Figure 8:
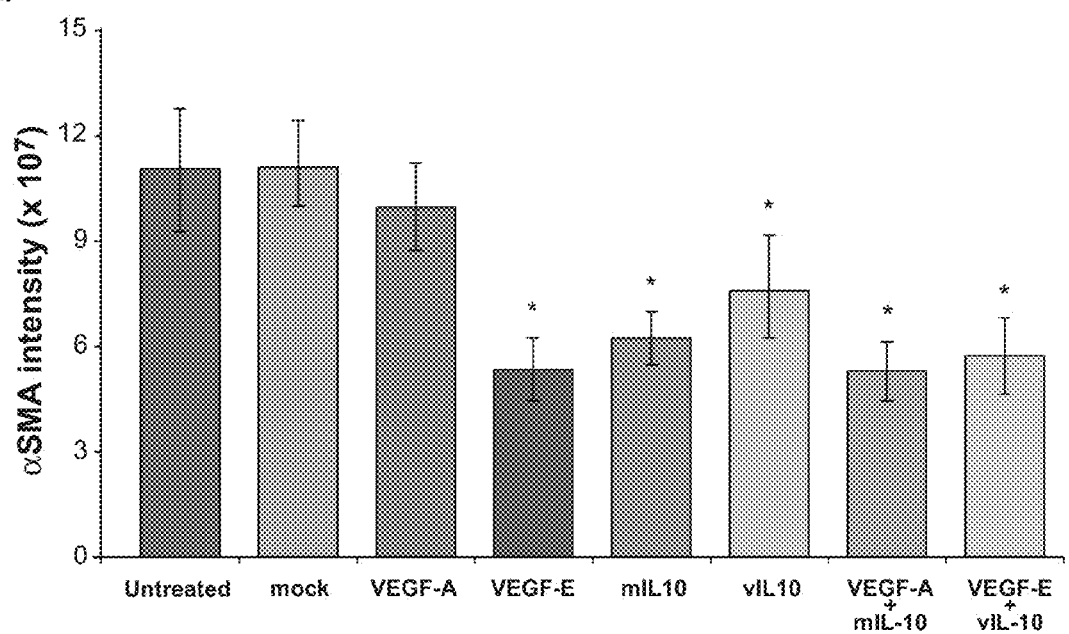
Figure 9:
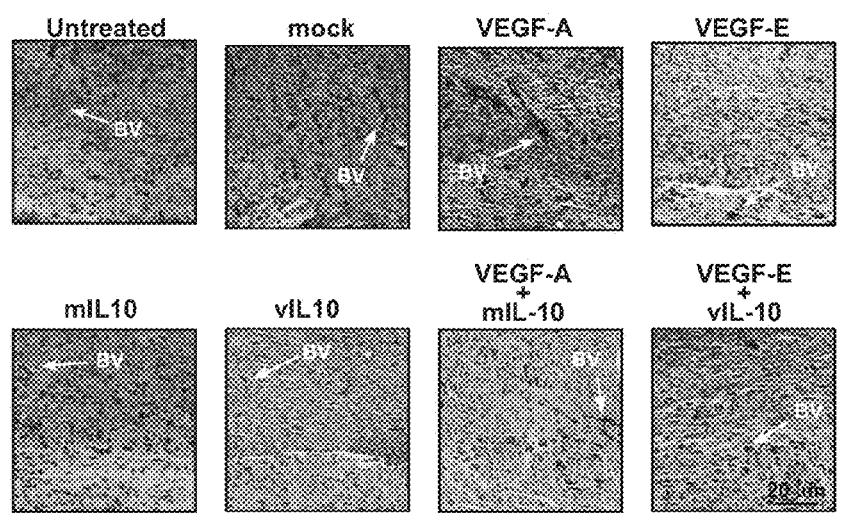
FIG. 9. Combination treatment of VEGF and IL-10 promotes vascular regeneration to a similar extent as individual VEGF treatments. (A) Re-vascularization of the neo-dermis was examined in wounded skin treated with different viral and mammalian factors. Zinc-fixed, paraffin-embedded skin sections from wound biopsies taken on day 9 were stained with MSB trichrome and photographed. Scale is indicated in the bottom right panel and examples of blood vessels (BV) are labeled. (B) The extent of dermal vascularization was quantified in 6 serial sections from 2 wounds from each of 4 mice by determining the fraction of dermis containing blood. Values are expressed as the mean areal fraction±SE. The areal fractions significantly above that of untreated wounds are indicated by an asterisk ($P \leq 0.05$).
Figure 9:
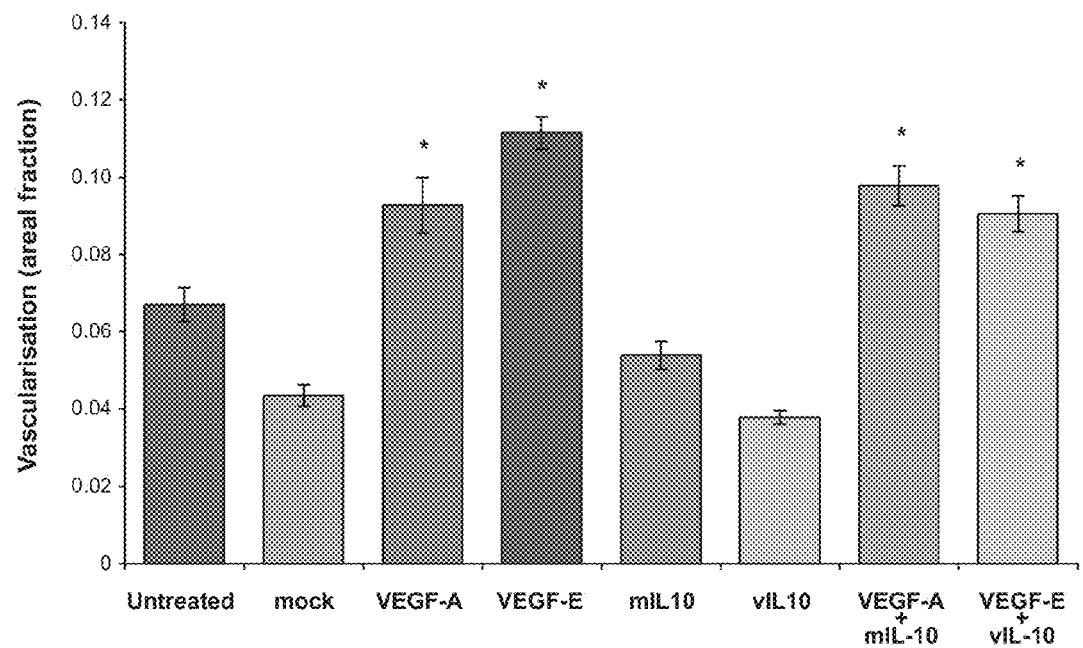
Figure 10:
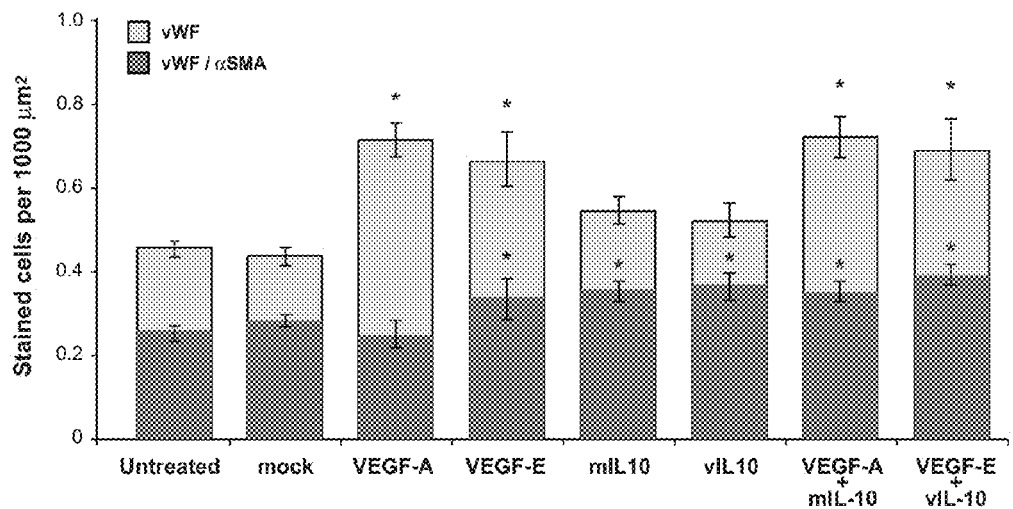
FIG. 10. Combination treatment of VEGF and IL-10 accelerates blood vessel maturation in the wound to a similar extent as individual VEGF treatments. (A) Zinc-fixed, paraffin-embedded skin sections from wound biopsies taken on day 9 were stained for the endothelial cell marker vWF and the periocyte marker αSMA (green, vWF staining; red, αSMA staining; blue, nuclear staining). Representative images are shown of wounded skin treated with different viral and mammalian factors. Scale is indicated in the bottom right panel and examples of red blood cells (auto-fluoresce orange/yellow) immature $vWF^{+ve}$ endothelial cells (ECs only) and mature vessels containing $vWF^{+ve}$ endothelial cells surrounded by $\alpha SMA^{+ve}$ periocytes (EC/periocyte) are enlarged and labelled. B. The total number of $vWF^{+ve}$ cells within the neo-dermis and the proportion associated with $\alpha SMA^{+ve}$ cells were quantified from 2 wounds from each of 4 mice. Values are expressed as the mean $vWF^{+ve}$ cells per 1000 $\mu m^2 \pm SE$. The average proportion of total $vWF^{+ve}$ cells found adjacent to $\alpha SMA^{+ve}$ cells, for each treatment, is shaded dark grey. Values significantly above that of untreated wounds are indicated by an asterisk ($P \leq 0.05$). (C) The total number of red blood cells within the neo-dermis was also quantified from two wounds from each of 4 mice. Values are expressed as the mean red blood cells per 1000 $\mu m^2 \pm SE$. Values significantly below that of untreated wounds are indicated by an asterisk ($P \leq 0.05$).
Figure 10:
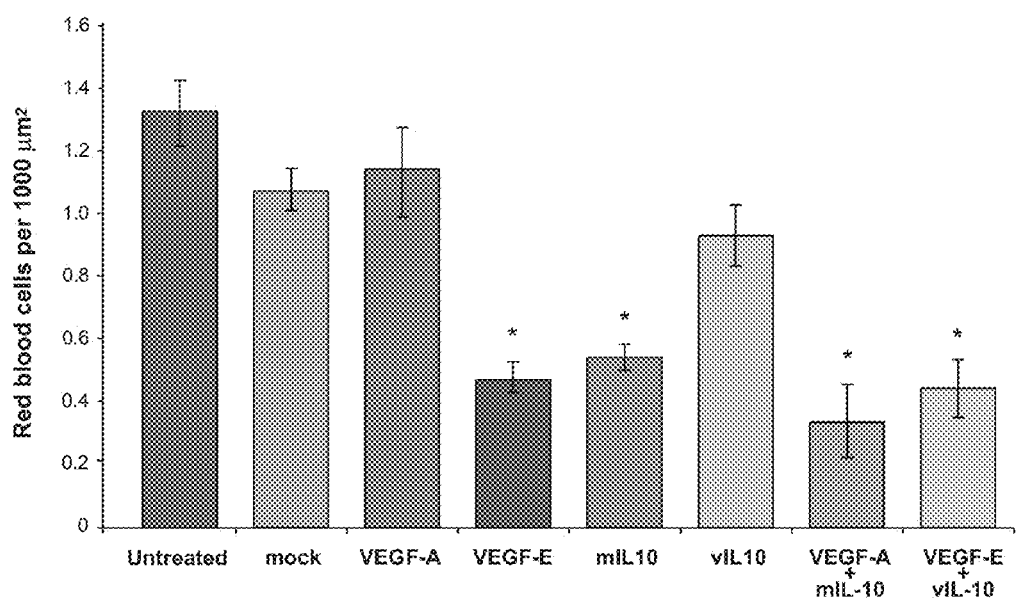
Figure 12:
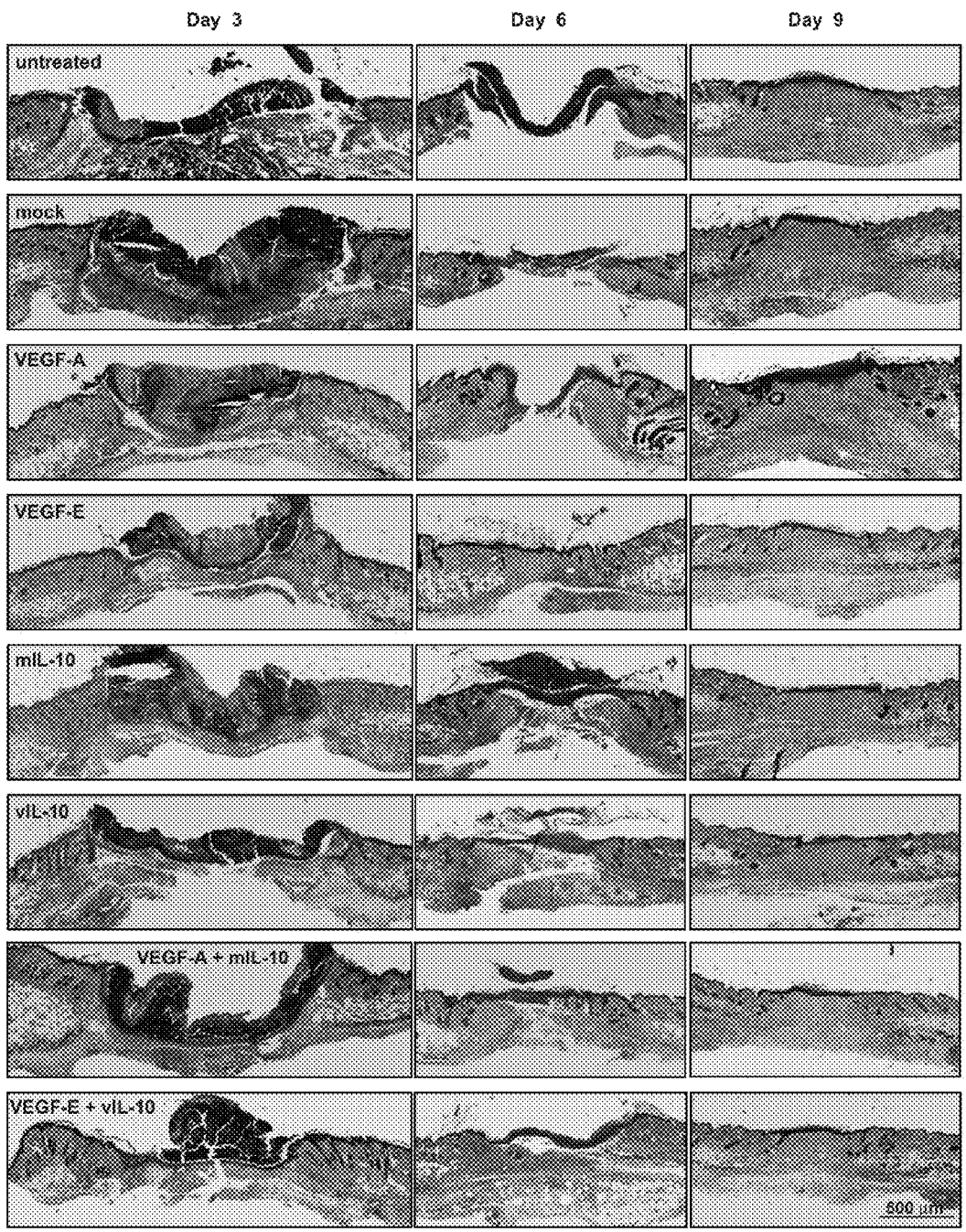
FIG. 12. Combination treatment with the viral VEGF and IL-10 accelerates dermal wound closure to a greater extent than the individual factors or mammalian combination but results in less granulation tissue formation than all other treatments. (A) Dermal regeneration was examined in wounded skin treated with different viral and mammalian factors. Skin biopsies taken at days 3, 6 and 9 were fixed in zinc salts solution and paraffin-embedded, then 4 µm sections were stained with MSB trichrome and photographed. Scale is indicated in the bottom right panel. (B) A schematic of a wound section with histological features labeled. Dermal coverage was calculated as the percentage of area of wound bed covered by granulation tissue as indicated. (C) Dermal coverage was quantified from 6 serial sections from 2 wounds from each of 4 mice using ImageJ and is expressed as the mean+/−SE. (D) The area (2/section) of the granulation tissue is expressed as the mean+/−SE. Values significantly greater than that of untreated skin ($P \leq 0.05$) are indicated by an asterisk. Significant differences between individual mammalian and viral treatments or between individual and combination treatments or between mammalian and viral combination treatments are indicated with a hash.
Figure 12:
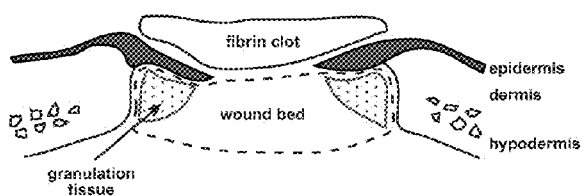
Figure 12:
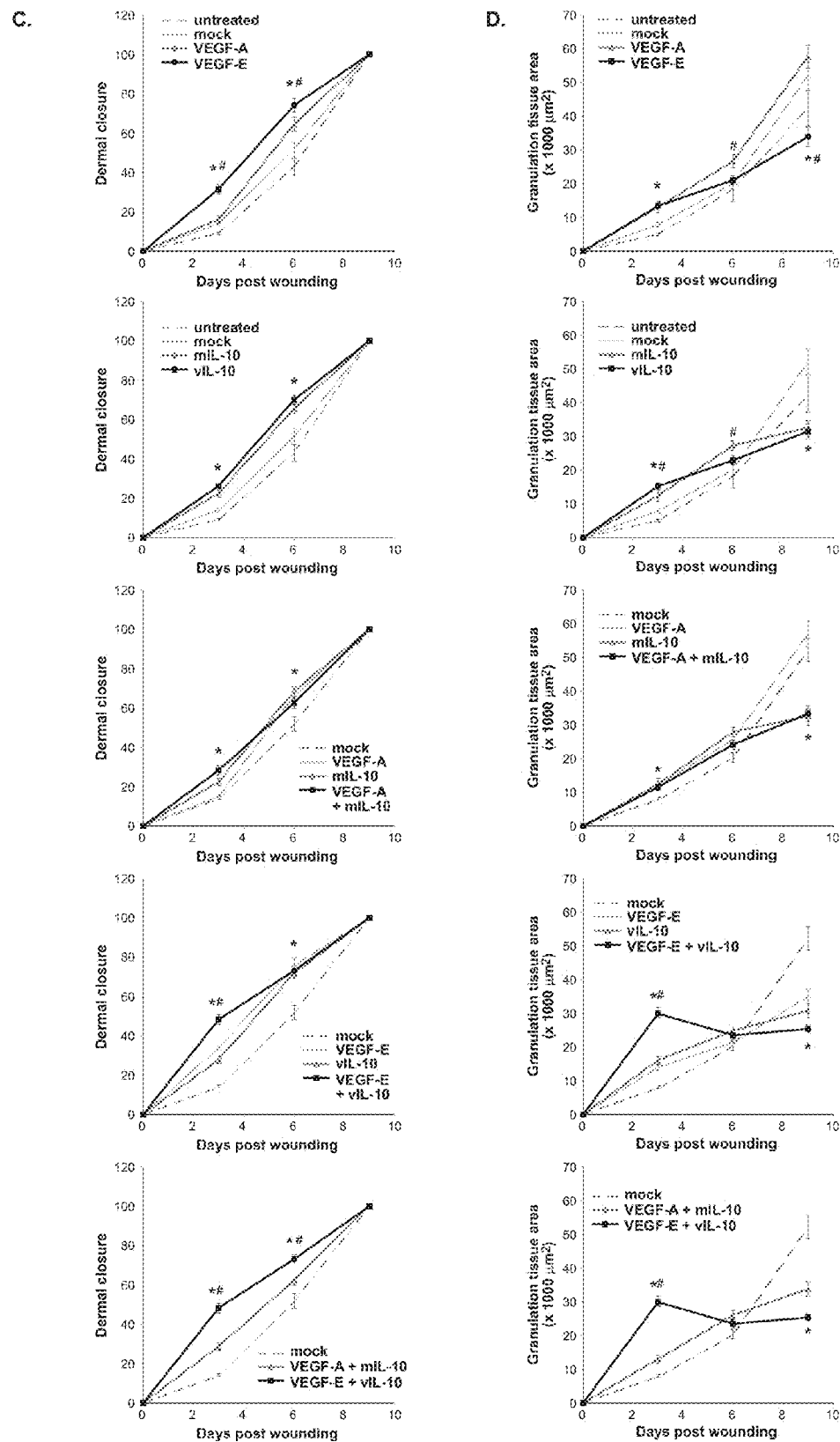
Figure 13:
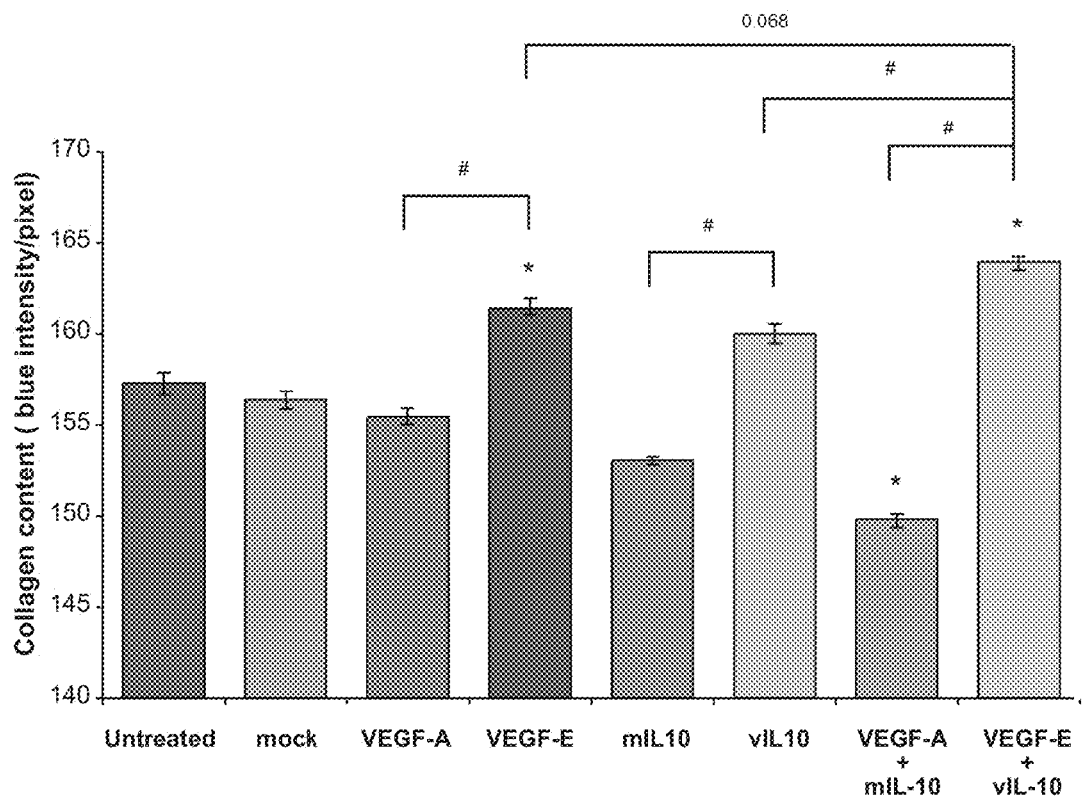
FIG. 13. Combination treatment with the viral VEGF and IL-10 accelerates granulation tissue remodeling to a greater extent than the individual treatments and the mammalian equivalents. Collagen content within the granulation tissue, of MSB trichrome-stained sections from skin biopsies taken at day 9, was calculated as the intensity of blue staining per pixel and is expressed as the mean+/−SE. Values significantly greater than that of untreated skin ($P \leq 0.05$) are indicated by an asterisk. Significant differences between treatments are indicated with a hash or the P value is stated.
Figure 14:
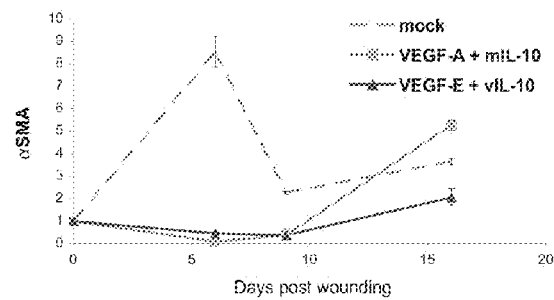
FIG. 14. Combination treatment of viral VEGF and IL-10 enhances granulation tissue remodelling by altering the timing and level of key regulators of dermal maturation. The expression of key dermal regulators in wounded skin treated with different viral and mammalian factors was examined over time using quantitative RT-PCR. cDNA was prepared by reverse transcription of total RNA (4 left flank wounds combined/treatment group). The level of (A) αSMA, (B) TGF-1β, (C) TGF-β3, (D) p53, (E) type III collagen and (F) type I collagen mRNA are shown for combination treatments over the course of healing. All mRNA levels are relative to the levels of GAPDH and unwounded skin. Values represent the mean±SE (n=3) and were consistent with values determined when the procedure was repeated with the 4 right flank wounds from each treatment group.
Figure 14:
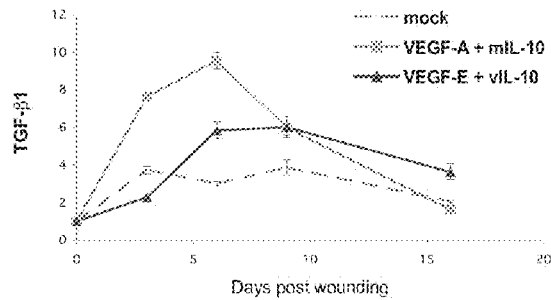
Figure 14:
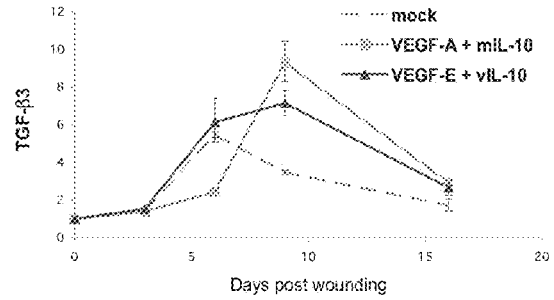
Figure 14:
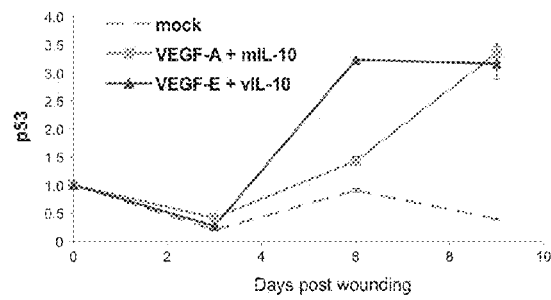
Figure 14:
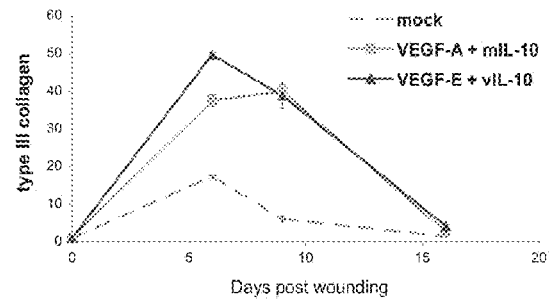
Figure 14:
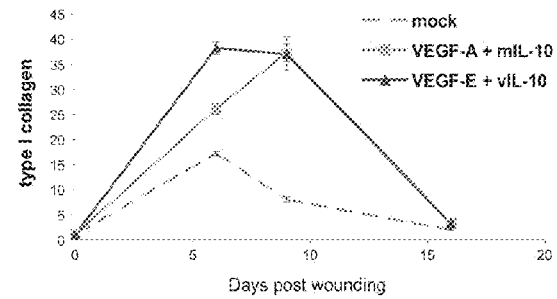

In Examples 6 and 7, the combination treatment of viral VEGF-E and viral IL-10 is shown to decrease wound inflammation and, importantly, to prevent the inflammatory response induced by VEGF treatment alone (see FIGS. 6 and 7). Example 8 demonstrates that the combination treatment of viral VEGF-E and viral IL-10 also reduces myofibroblast differentiation and will limit wound contraction (see FIG. 8). Examples 9, 10 and 11 show that the combination treatment of viral VEGF-E and viral IL-10 can promote wound re-vascularization (see FIGS. 9-11). The combination treatment of viral VEGF-E and viral IL-10 was also shown in Examples 12-14 to enhance dermal regeneration and granulation tissue remodeling to a greater extent than the individual viral treatments or the mammalian/cellular combination (see FIGS. 12-14).

Figure 15:
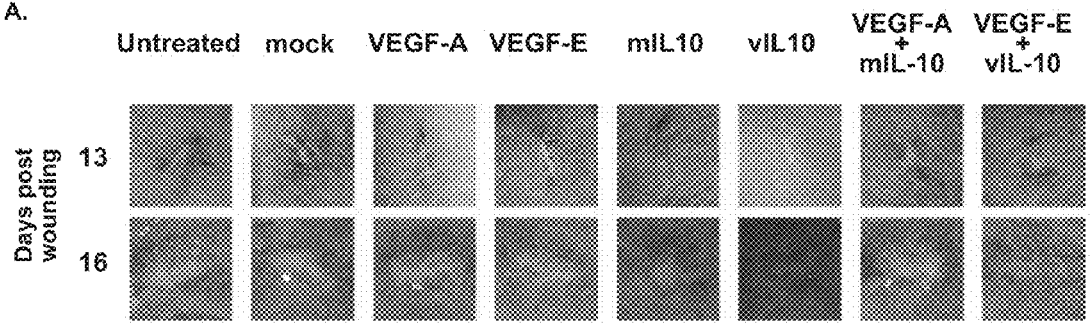
FIG. 15. Combination treatment of viral VEGF-E and IL-10 enhances scar resolution to a greater extent than the individual treatments or the mammalian equivalents. (A) Photographs of the healed punch wounds at the indicated time points following treatment with different viral and mammalian factors. (B) External wounds (day 13) were scored visually on a scale of 1:5, where one represented a fully resolved wound while five denoted that an obvious scar and are presented as the mean+/−SE (n=8 wounds per group, scored by 6 observers). (C) The area of internal scars (day 16) were measured using Image J and are presented as the mean+/−SE (n=8). Values significantly less than mock-treated wounds ($P \leq 0.05$) are indicated by an asterisk. Significant differences between certain treatments are indicated with a hash.
Figure 15:
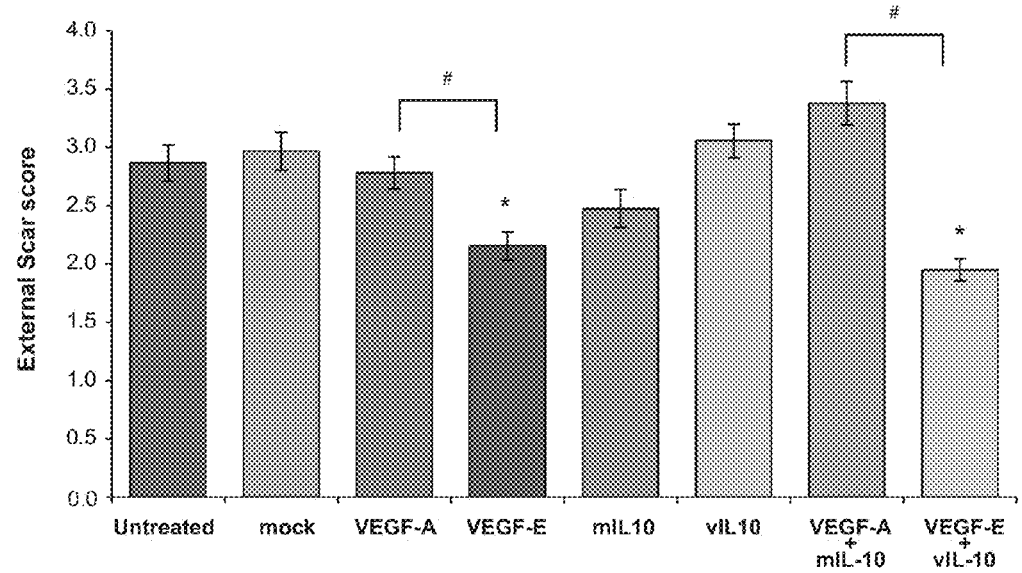
Figure 15:
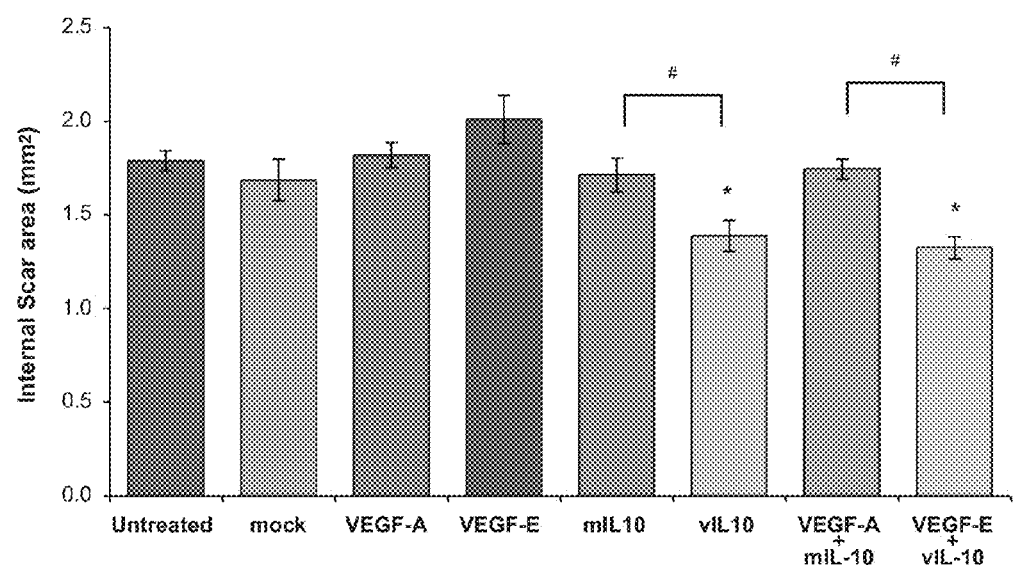

Example 15 demonstrates that the combination treatment of viral VEGF-E and viral IL-10 visually improves scar resolution and reduces scar size to a greater extent than the individual viral treatments or the mammalian/cellular combination (see FIG. 15).

In summary, as shown in Examples 2 and 12-15 and related FIGS. 1 and 12-15, combining a viral VEGF with regenerative properties and an anti-inflammatory viral interleukin, such as VEGF-E and viral IL-10, for example, enhances wound closure and dermal regeneration/remodeling, and limits scarring, to a greater extent than the individual viral treatments or the mammalian/cellular combination. Additionally, as shown in Examples 3-5 and FIGS. 3-5, treatment with a combination of VEGF with regenerative properties and an anti-inflammatory interleukin from a viral source, enhances epidermal regeneration and resolution to a greater extent than the individual treatments. Importantly, combining a virally-sourced VEGF and anti-inflammatory interleukin does not impair the ability of the interleukin, for example vIL-10, to decrease inflammation and myofibroblast differentiation and prevents the inflammatory side effects of VEGF treatment. This is demonstrated in Examples 6-8 (see related FIGS. 6-8). Another important aspect of the inventions is that combining a viral VEGF and a viral interleukin, such as VEGF-E and vIL-10, for example, does not impair the ability of the VEGF to enhance wound re-vascularization (see Examples 9-11, and FIGS. 9-11).

DEFINITIONS

As used herein, a "disorder" is any disorder, disease, or condition that would benefit from an agent that initiates, accelerates, promotes or enhances wound healing (including acute wounds, dehiscent wounds, and slow-healing delayed-healing and chronic wounds), reduces inflammation, reduces or lessens scarring, improves scar quality, reduces fibrosis, and/or reduces adhesions. For example, diseases, disorders, and conditions include acute wounds. Diseases, disorders, and conditions also include dehiscent wounds, and slow-healing delayed-healing and chronic wounds. Also included are diseases, disorders, and conditions characterized by excess production of fibrous material, including excess production of fibrous material within the extracellular matrix. Also included are diseases, disorders and conditions characterized by replacement of normal tissue elements by abnormal, non-functional, and/or excessive accumulation of matrix-associated components. Also included are diseases, disorders and conditions characterized by adhesion formation. Also included is any disorder, disease, or condition that would benefit from an agent that promotes wound healing and/or reduces swelling, inflammation, and/or scar formation (including abnormal and excessive scarring, including keloid scars, hypertrophic scars, widespread (stretched) scars, and atrophic (depressed) scars). For example, included are wounds resulting from surgery or trauma, wounds that do not heal at expected rates (such as delayed-healing wounds, incompletely healing wounds, chronic wounds, and dehiscent wounds), and wounds associated abnormalities in connection with neuropathic, ischemic, microvascular pathology, pressure over bony area (tailbone (sacral), hip (trochanteric), buttocks (ischial), or heel of the foot), reperfusion injury, and valve reflux etiology and conditions. Also included are diseases, disorders and conditions that would benefit from enhanced cellular migration, lessened cellular adhesion, scarring and inflammation as described herein.

As used herein, "subject" refers to any mammal, including humans, domestic and farm animals, and zoo, sports, and pet animals, such as dogs, horses, cats, sheep, pigs, cows, etc. The preferred mammal herein is a human, including adults, children, and the elderly. A subject may also be a bird, including zoo, sports, and pet birds. Preferred sports animals are horses and dogs. Preferred pet animals are dogs and cats.

As used herein, "preventing" means preventing in whole or in part, or ameliorating or controlling, or reducing or halting the production or occurrence of the thing or event, for example, the disease, disorder or condition, to be prevented.

As used herein, a "therapeutically effective amount" or "effective amount" in reference to the compounds or compositions of the instant invention refers to the amount sufficient to induce a desired biological, pharmaceutical, or therapeutic result. That result can be alleviation of the signs, symptoms, or causes of a disease or disorder or condition, or any other desired alteration of a biological system. In the present invention, the result will involve preventing fibrosis. In another aspect of the present invention, the result will involve the prevention and/or reduction of adhesions. In another aspect of the present invention, the result will involve the prevention and/or reduction of scarring and abnormal scarring, as well as prevention and/or reduction of excessive scar formation and other types of abnormal proliferation of tissue, including keloid scars, hypertrophic scars, widespread scars, and atrophic scars. In another aspect of the present invention, the result will involve the prevention and/or reduction of inflammation in any tissue or organ.

According to a further aspect, the result will involve the promotion and/or improvement of wound healing and closure of wounds, in whole or in part, including improvements in rates of healing. Other benefits include reductions in swelling, inflammation and/or scar formation, in whole or in part.

As used herein, the terms "treating" and "treatment" refer to both therapeutic treatment and prophylactic or preventative measures. Those in need of treatment include those already with the disease, disorder or condition as well as those prone to having the disease, disorder or condition or diagnosed with the disease, disorder or condition or those in which the disease, disorder or condition is to be prevented. Thus, by way of example, the promotion of wound healing, the reduction of inflammation, the promotion of cell migration, the reduction of cellular adhesion, anti-fibrotic applications of compounds and compositions and formulations of the invention administered prior to the formation of fibrosis or fibrotic tissue are within the scope of the present invention, as are anti-adhesion applications of compounds and compositions and formulations of the invention administered prior to the formation of an adhesion, and anti-scarring applications of compounds and compositions and formulations of the invention administered prior to scar formation including, for example, in a scar reduction surgery or procedure (or surgical pre-treatment).

As used herein, a "viral VEGF" include vascular endothelial growth factors of viral origin, and include viral VEGFs with regenerative properties, as well as naturally occurring or non-naturally occurring molecules that mimic the regenerative properties of vascular endothelial growth factors of viral origin (e.g., VEGF-E). For example, viral VEGFs that promote angiogenesis are included, as are viral VEGFs that promote epidermal regeneration. In one embodiment, the viral VEGF may be a VEGF-E. In another embodiment, the viral VEGF is orf virus VEGF. Examples of other viral vascular endothelial growth factors include parapoxvirus VEGFs, as well as VEGFs from all orf virus strains that encode a VEGF-E (e.g., NZ2, NZ10, NZ7, D1701 and so on). Parapoxvirus VEGFs include VEGFs from parapoxvirus strains BPSV, PVNZ and PCPV, and all other strains that encode a VEGF-E. VEGFs from other viral species are included. In other embodiments, the viral VEGF can be any molecule, whether naturally occurring or non-naturally occurring (including derivatives or variants of a naturally occurring molecule designed or discovered (e.g., through random or directed mutagenesis)), that activates VEGFR-2 more than the VEGFR-1. In other embodiments, the viral VEGF can be any molecule, whether naturally occurring or non-naturally occurring (including derivatives or variants of a naturally occurring molecule designed or discovered (e.g., through random or directed mutagenesis)), that activates VEGFR-2 but does not appreciably bind to or activate VEGFR-1.

As used herein, an "anti-inflammatory cytokine" is a cytokine of viral or mammalian origin that is useful in controlling or ameliorating inflammation.

As used herein, a "viral anti-inflammatory cytokine" is a cytokine of viral origin that is useful in controlling or ameliorating inflammation. Similarly, a "mammalian anti-inflammatory cytokine" is a cytokine of mammalian origin that is useful in controlling or ameliorating inflammation.

As used herein, a "mammalian anti-inflammatory interleukin" is an interleukin of mammalian origin that is useful in controlling or ameliorating inflammation.

As used herein, the terms "mammalian" and "cellular" in the context of, for example, an anti-inflammatory cytokine or an anti-inflammatory interleukin are intended to mean the same thing, that is (e.g.) the cytokine or interleukin is from a cellular or mammalian origin.

As used herein, an "anti-inflammatory viral interleukin" is an interleukin of viral origin that is useful in controlling or ameliorating inflammation. Anti-inflammatory viral interleukins include IL-10 of viral origin. For example, anti-inflammatory viral interleukins include IL-10 from the orf virus. Other examples of viral interleukin species include viral interleukins from orf viruses, EBVs, CMVs, including IL-10s from these and other viruses. Viral interleukins include poxvirus IL-17 homologues, the EBV CXCR homolog, and the KSHV IL-6 homolog and IL-8R homologue. These and all other viral interleukins with anti-inflammatory activity are within the scope of the present invention. Poxviruses also have anti-inflammatory chemokine mimics, interleukin/TNF/chemokine binding proteins and other IL-119/20/22-like proteins. All such proteins having anti-inflammatory activity are within the scope of the present invention.

The terms "peptidomimetic" and "mimetic" include naturally occurring and synthetic chemical compounds that may have substantially the same structural and functional characteristics of protein regions that they mimic. In the case of connexin proteins, these may mimic, for example, the extracellular loops of connexin-repeating domains in the extracellular region of connexin proteins involved in connexin repeat association, adherens junction formation and maintenance, and cell-cell adhesion.

"Peptide analogs" refer to the compounds with properties analogous to those of the template peptide and may be non-peptide drugs. "Peptidomimetics" (also known as "mimetic peptides"), which include peptide-based compounds, also include such non-peptide based compounds such as peptide analogs. Peptidomimetics that are structurally similar to therapeutically useful peptides may be used to produce an equivalent or enhanced therapeutic or prophylactic effect. Generally, peptidomimetics are structurally identical or similar to a paradigm polypeptide (i.e., a polypeptide that has a biological or pharmacological function or activity), but can also have one or more peptide linkages optionally replaced by a linkage selected from the group consisting of, for example, —CH$_2$NH—, —CH$_2$S—, —CH$_2$—CH$_2$—, —CH=CH— (cis and trans), —COCH$_2$—, —CH(OH)CH$_2$—, and —CH$_2$SO—. The mimetic can be either entirely composed of natural amino acids, or non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity. For example, in one embodiment, a mimetic composition may be useful as an anti-connexin agent if it is capable of down-regulating biological actions or activities of connexin proteins, connexin complexes, or adherens junctions, such as, for example, preventing the head-to-head association of connexin repeats of opposing connexin extracellular domains on adjoining cells, association of connexin proteins in the same cell, formation of connexin complexes in cells, association of connexin complexes with the actin cytoskeleton, and/or adherens junction formation.

The terms "modulator" and "modulation" of activity, as used herein in its various forms, refers to inhibition in whole or in part of the expression or action or activity of a compound, for example, a connexin protein, connexin complex, or adherens junction, and may function as anti-connexin agents.

In general, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants may be referred to herein as "proteins," and shall be deemed to be a "protein" unless otherwise indicated. The term "fragment" of a protein refers to a polypeptide comprising fewer than all of the amino acid residues of the protein. A "domain" of a protein is also a fragment, and comprises the amino acid residues of the protein often required to confer activity or function.

As used herein, "simultaneously" is used to mean that the one or more agents of the invention, for example, vascular endothelial growth factor and anti-inflammatory cytokine, are administered concurrently, whereas the term "in combination" is used to mean they are administered, if not simultaneously or in physical combination, then "sequentially" within a time frame that they both are available to act therapeutically. Thus, administration "sequentially" may permit one agent to be administered within minutes (for example, 1, 2, 3, 4, 5, 10, 15, 20, 25, 30) minutes or a matter of hours, days, weeks, or months after the other, provided that both are present in effective amounts. The time delay between administration or administrations of the components will vary depending on the exact nature of the components, the interaction between them, and their respective half-lives.

The term "dressing" refers to a dressing for topical application to a wound (or to a tissue or organ) and excludes compositions suitable for systemic administration. For example, the one or more viral VEGFs and/or anti-inflammatory viral interleukins may be dispersed in or on a solid sheet of wound contacting material such as a woven or nonwoven textile material, or may be dispersed in a layer of foam such as polyurethane foam, or in a hydrogel such as a polyurethane hydrogel, a polyacrylate hydrogel, gelatin, carboxymethyl cellulose, pectin, alginate, and/or hyaluronic acid hydrogel, for example in a gel or ointment. In certain embodiments the one or more viral VEGFs and/or anti-inflammatory viral interleukins are dispersed in or on a biodegradable sheet material that provides sustained release of the active ingredients into the wound, for example a sheet of freeze-dried collagen, freeze-dried collagen/alginate mixtures (available under the Registered Trade Mark FIBRACOL from Johnson & Johnson Medical Limited) or freeze-dried collagen/oxidized regenerated cellulose (available under the Registered Trade Mark PROMOGRAN from Johnson & Johnson Medical Limited).

As used herein, "matrix" includes for example, matrices such as collagen, acellular matrices, crosslinked biological scaffold molecules, tissue-based matrices (including pig-based wound healing matrices), cultured epidermal autografts, cultured epidermal allografts, tissue-engineered skin, collagen and glycosaminoglycan dermal matrices inoculated with autologous fibroblasts and keratinocytes, AlloDerm® (a nonliving allogeneic acellular dermal matrix with intact basement membrane complex), living skin equivalents (e.g., Dermagraft® (living allogeneic dermal fibroblasts grown on degradable scaffold), TransCyte® (an extracellular matrix generated by allogeneic human dermal fibroblasts), Apligraf® (a living allogeneic bilayered construct containing keratinocytes, fibroblasts and bovine type I collagen), Integra® (two-layer membrane system for skin replacement comprising a dermal replacement layer made of a porous template of fibers of bovine tendon collagen and glycosaminoglycan (chondroitin-6-sulfate) and an epidermal substitute layer made of thin silicone to control moisture loss), Cyzact™ (human dermal fibroblasts delivered via a fibrin), ICX-SKN (a combination of fibroblasts and fibrin matrix that are remodeled to produce a collagen matrix), Keragraft™ (a human stem cell-derived product being developed for wound care as an autologous epidermal equivalent), OASIS® Wound Matrix (biologically derived extracellular matrix-based wound product created from porcine-derived acellular small intestine submucosal), and OrCel™ (allogeneic fibroblasts and keratinocytes seeded in opposite sides of bilayered matrix of bovine collagen), BioBrane, cultured allogenic keratinocytes, animal derived dressings (e.g., Oasis's porcine small intestinal submucosa acellular collagen matrix; and E-Z Derm's acellular xenogeneic collagen matrix), tissue-based bioengineered structural frameworks, scaffolds, biomanufactured bioprostheses, and other implanted or applied structures such as for example, vascular grafts suitable for cell infiltration and proliferation useful in the promotion of wound healing. A matrix is also provided by a cell therapy spray suspension known as HP802-247, being developed by HealthPoint, which consists of two components that are sprayed sequentially on the wound bed at the time of treatment: a fibrinogen solution and a cell preparation containing a mixture of growth arrested, living, allogeneic epidermal keratinocytes and dermal fibroblasts.

Additional suitable biomatrix material may include chemically modified collagenous tissue to reduce antigenicity and immunogenicity. Other suitable examples include collagen sheets for wound dressings, antigen-free or antigen reduced acellular matrix (Wilson, et al., *Trans Am Soc Artif Intern* 1990; 36:340-343), or other biomatrices that have been engineered to reduce the antigenic response to the xenograft material. Other matrices useful in promotion of wound healing may include for example, processed bovine pericardium proteins comprising insoluble collagen and elastin (Courtman, et al., *J Biomed Mater Res* 1994; 28:655-666) and other acellular tissue which may be useful for providing a natural microenvironment for host cell migration to accelerate tissue regeneration (Malone, et al., *J Vasc Surg* 1984; 1:181-91). In certain embodiments, the matrix material may be supplemented with one or more anti-connexin agents, anti-osteopontin agents, anti-connexin43 agents, and/or the one or more therapeutic agents for site-specific release of such agents and/or viral VEGFs and/or anti-inflammatory viral interleukins.

Wounds and Wound Classification

Chronic wounds, slow healing wounds, and incomplete healing wounds often result in infection and can lead to amputation or death. It has been discovered that use of certain compounds, including those described or referenced herein, may block, inhibit, or alter cell communications, which may promote closure and healing in chronic, slow healing, and incomplete healing wounds.

By "wound" is meant an injury to any tissue, including, for example, acute, delayed, slow, or difficult to heal wounds, and chronic wounds. Examples of wounds may include both open and closed wounds. Wounds include, for example, burns, incisions, excisions, lacerations, abrasions, puncture or penetrating wounds, surgical wounds, contusions, hematomas, crushing injuries, and ulcers. Also included are wounds that do not heal at expected rates.

By a "wound that does not heal at the/an expected rate" is meant an injury to any tissue that does not heal in an expected or typical time frame, including delayed, slow, or difficult to heal wounds (including delayed or incompletely healing wounds), and chronic wounds. Examples of wounds that do not heal at the expected rate include diabetic ulcers, diabetic foot ulcers, vasculitic ulcers, arterial ulcers, venous ulcers, venous stasis ulcers, pressure ulcers, decubitus ulcers, infectious ulcers, trauma-induced ulcers, burn ulcers, ulcerations associated with pyoderma gangrenosum, and mixed ulcers.

As described herein, a delayed or difficult to heal wound may include, for example, a wound that is characterized at least in part by one or more of 1) a prolonged inflammatory phase, 2) a slow forming extracellular matrix, and 3) a stalled or decreased rate of epithelialization.

In the art, the term "chronic wound" refers generally to a wound that has not healed within about three months, but can be wounds that have not healed within about one or two months. Chronic skin wounds include, for example, pressure ulcers, diabetic ulcers, venous ulcers, arterial ulcers, inflammatory ulcers, and mixed ulcers. The chronic wound may be an arterial ulcer that can include ulcerations resulting from complete or partial arterial blockage. The chronic wound may be a venous stasis ulcer, which can include ulcerations resulting from a malfunction of the venous valve and the associated vascular disease. The chronic wound may be a trauma-induced ulcer.

As used herein, chronic wound can also include, for example, a wound that is characterized at least in part by 1) a chronic self-perpetuating state of wound inflammation, 2) a deficient and defective wound extracellular matrix (ECM), 3) poorly responding (senescent) wound cells (e.g. fibroblasts), limited ECM production, and 4) failure of re-epithelialization due in part to lack of the necessary ECM orchestration and lack of scaffold for migration.

Chronic wounds can also be characterized, for example, by 1) prolonged inflammation and proteolytic activity, leading to ulcerative lesions, including, for example, diabetic, pressure (decubitus), venous, and arterial ulcers, 2) prolonged fibrosis in the wound leading to scarring, 3) progressive deposition of matrix in the affected area, 4) longer repair times, 5) less wound contraction, 6) slower re-epithelialization, and 7) increased thickness of granulation tissue.

Exemplary chronic wounds also include "pressure ulcers." Exemplary pressure ulcers may include all four stages of wound classifications based on AHCPR (Agency for Health Care Policy and Research, U.S. Department of Health and Human Services) guidelines, including for example, Stage 1.

A Stage 1 pressure ulcer is an observable pressure related alteration of intact skin whose indicators as compared to the adjacent or opposite area on the body may include changes in one or more of the following: skin temperature (warmth or coolness), tissue consistency (firm or boggy feel), and/or sensation (pain, itching). The ulcer appears as a defined area of persistent redness in lightly pigmented skin, whereas in darker skin tones, the ulcer may appear with persistent red, blue, or purple hues. Stage 1 ulceration may include non-blanchable erythema of intact skin and the heralding lesion of skin ulceration. In individuals with darker skin, discoloration of the skin, warmth, edema, induration, or hardness may also be indicators of stage 1 ulceration. Stage 2 ulceration may be characterized by partial thickness skin loss involving epidermis, dermis, or both. The ulcer is superficial and presents clinically as an abrasion, blister, or shallow crater. Stage 3 ulceration may be characterized by full thickness skin loss involving damage to or necrosis of subcutaneous tissue that may extend down to, but not through, underlying fascia. The ulcer presents clinically as a deep crater with or without undermining of adjacent tissue. Stage 4 ulceration may be characterized by full thickness skin loss with extensive destruction, tissue necrosis, or damage to muscle, bone, or supporting structures (e.g., tendon, joint capsule, etc.).

Exemplary chronic wounds also include "decubitus ulcers." Exemplary decubitus ulcer may arise as a result of prolonged and unrelieved pressure over a bony prominence that leads to ischemia. The wound tends to occur in patients who are unable to reposition themselves to off-load weight, such as paralyzed, unconscious, or severely debilitated persons. As defined by the U.S. Department of Health and Human Services, the major preventive measures include identification of high-risk patients; frequent assessment; and prophylactic measures such as scheduled repositioning, appropriate pressure-relief bedding, moisture barriers, and adequate nutritional status. Treatment options may include, for example, pressure relief, surgical and enzymatic debridement, moist wound care, and bacterial load control. Certain embodiments of the invention involve treating a chronic wound characterized by a decubitus ulcer or ulceration that results from prolonged, unrelieved pressure over a bony prominence that leads to ischemia.

Exemplary chronic wounds also include "arterial ulcers." Arterial ulcers include those characterized by complete or partial arterial blockage, which may lead to tissue necrosis and/or ulceration. Signs of arterial ulcer can include, for example, pulselessness of the extremity; painful ulceration; small, punctate ulcers that are usually well circumscribed; cool or cold skin; delayed capillary return time (briefly push on the end of the toe and release, normal color should return to the toe in about 3 seconds or less); atrophic-appearing skin (for example, shiny, thin, dry); and loss of digital and pedal hair.

Exemplary chronic wounds also include "venous ulcers." Exemplary venous ulcers include the most common type of ulcer affecting the lower extremities and may be characterized by malfunction of the venous valve. The normal vein has valves that prevent the backflow of blood. When these valves become incompetent, the backflow of venous blood causes venous congestion. Hemoglobin from the red blood cells escapes and leaks into the extravascular space, causing the brownish discoloration commonly noted. It has been shown that the transcutaneous oxygen pressure of the skin surrounding a venous ulcer is decreased, indicating that there are forces obstructing the normal vascularity of the area. Lymphatic drainage and flow also plays a role in these ulcers. A venous ulcer can appear near the medial malleolus and usually occurs in combination with an edematous and indurated lower extremity; it may be shallow, not too painful, and may present with a weeping discharge from the affected site.

Exemplary chronic wounds also include "venous stasis ulcers." Exemplary venous stasis ulcer are characterized by chronic passive venous congestion of the lower extremities that results in local hypoxia. One possible mechanism of pathogenesis of these wounds includes the impediment of oxygen diffusion into the tissue across thick perivascular fibrin cuffs. Another mechanism is that macromolecules leaking into the perivascular tissue trap growth factors needed for the maintenance of skin integrity. Additionally, the flow of large white blood cells slows due to venous congestion, occluding capillaries, becoming activated, and damaging the vascular endothelium to predispose to ulcer formation.

Exemplary chronic wounds further include "diabetic foot ulcers." Diabetic patients with exemplary diabetic foot ulcer are prone to foot ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy can lose the ability to sense a sustained pressure insult and, as a result, tissue ischemia and necrosis may occur leading to, for example, plantar ulcerations. Additionally, microfractures in the bones of the foot, if unnoticed and untreated, may result in disfigurement, chronic swelling, and additional bony prominences. Microvascular disease is one of the significant complications for diabetics that may also lead to ulcerations.

Exemplary chronic wounds can include "traumatic ulcers." Formation of exemplary traumatic ulcers may occur as a result of traumatic injuries to the body. These injuries include, for example, compromises to the arterial, venous, or lymphatic systems; changes to the bony architecture of the skeleton; loss of tissue layers—epidermis, dermis, subcutaneous soft tissue, muscle or bone; damage to body parts or organs and loss of body parts or organs.

Exemplary chronic wounds can include "burn ulcers" including, for example, ulceration that occur as a result of a burn injury, including a first degree burn (i.e., superficial, reddened area of skin); a second degree burn (a blistered injury site which may heal spontaneously after the blister fluid has been removed); a third degree burn (burn through the entire skin and usually require surgical intervention for wound healing); scalding (may occur from scalding hot water, grease or radiator fluid); a thermal burn (may occur from flames, usually deep burns); a chemical burn (may come from acid and alkali, usually deep burns); an electrical burn (either low voltage around a house or high voltage at work); an explosion flash (usually superficial injuries); and contact burns (usually deep and may occur from muffler tail pipes, hot irons, and stoves).

As used herein, a delayed or difficult to heal wound may include, for example, a wound that is characterized at least in part by 1) a prolonged inflammatory phase, 2) a slow forming extracellular matrix (ECM), and 3) a decreased rate of epithelialization.

As used herein, "fibrotic" diseases, disorders, or conditions include those mentioned herein, and further include acute and chronic, clinical or sub-clinical presentation, in which fibrogenic associated biology or pathology is evident. Fibrotic diseases, disorders, or conditions include diseases, disorders or conditions characterized, in whole or in part, by the excess production of fibrous material, including excess production of fibrotic material within the extracellular matrix, or the replacement of normal tissue elements by abnormal, non-functional, and/or excessive accumulation of matrix-associated components. Fibrotic diseases, disorders, or conditions include, for example, fibrogenic-related biology or pathology characterized by fibrosis.

Exemplary fibrotic diseases, disorders, and conditions include, for example, scleroderma (including morphea, generalized morphea, or linear scleroderma), kidney fibrosis (including glomerular sclerosis, renal tubulointerstitial fibrosis, progressive renal disease or diabetic nephropathy), cardiac fibrosis (e.g., myocardial fibrosis), pulmonary fibrosis (e.g., glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fascilitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myleoid leukemia, acute myelogenous leukemia, myelodysplastic syndrome, myeloproferative syndrome, gynecological cancer, Kaposi's sarcoma, Hansen's disease, collagenous colitis, and acute fibrosis.

Fibrotic diseases, disorders, and conditions can also include contractures. Contractures, including post-operative contractures, refer to a permanent or long term reduction of range of motion due to tonic spasm or fibrosis, or to loss of normal tissue compliance, motion, or equilibrium (e.g., muscle, tendon, ligament, fascia, synovium, joint capsule, other connective tissue, or fat). In general, the condition of contracture may involve a fibrotic response with inflammatory components, both acute and chronic. Some of which may be associated with surgery, including a release procedure. Hereditary contractures such as Dupytren's contracture, Peyronie's disease, and Ledderhose's disease are also included.

Fibrosis can be either chronic or acute. Fibrotic conditions include excessive amounts of fibrous tissue, including excessive amounts of extracellular matrix accumulation within a tissue, forming tissue that causes dysfunction and, potentially, organ failure. Chronic fibrosis includes fibrosis of the major organs, most commonly lung, liver, kidney, and/or heart. Acute fibrosis (usually with a sudden and severe onset and of short duration) occurs typically as a common response to various forms of trauma including injuries, ischemic illness (e.g. cardiac scarring following heart attack), environmental pollutants, alcohol and other types of toxins, acute respiratory distress syndrome, radiation, and chemotherapy treatments. All tissues damaged by trauma can become fibrotic, particularly if the damage is repeated.

Response to injury involves coordinated and temporally regulated patterns of mediators and sequence of cellular events in tissues subsequent to injury. The initial injury triggers a coagulation cascade and an acute local inflammatory response followed by mesenchymal cell recruitment, proliferation, and matrix synthesis. Uncontrolled matrix accumulation, often involving aberrant cytokine pathways, can lead to fibrotic conditions or disorders. Progressive fibrosis in vital organs such as the lung, kidney, liver, heart, brain, and bone marrow, is both a major cause of illness and death.

Adhesions

Within other aspects of the invention, methods are provided for treating, reducing the incidence or severity of, and/or preventing or retarding adhesions, surgical adhesions, and/or secondary surgical adhesions by administering to a patient a viral VEGF and an anti-inflammatory viral interleukin.

Adhesion formation is a complex process in which bodily tissues that are normally separate grow together. For example, post-operative adhesions have been reported to occur in about 60% to 90% of patients undergoing major gynecological surgery. Surgical trauma as a result of tissue (e.g., epithelial, connective, muscle, and nerve tissue) drying, ischemia, thermal injury, infection, or the presence of a foreign body, has long been recognized as a stimulus for tissue adhesion formation. These adhesions are a major cause of failed surgical therapy and are the leading cause of bowel obstruction and infertility. Other adhesion-treated complications include chronic pelvic pain, urethral obstruction, and voiding dysfunction.

Generally, adhesion formation is an inflammatory reaction in which factors are released, increasing vascular permeability and resulting in fibrinogen influx and fibrin deposition. This deposition forms a matrix that bridges the abutting tissues. Fibroblasts accumulate, attach to the matrix, deposit collagen, and induce angiogenesis. If this cascade of events can be prevented within 4 to 5 days following surgery, adhesion formation can be inhibited.

Secondary surgical adhesions may also form as a result of a corrective surgical procedure designed to correct and existing adhesion. The procedure may be a release or separation procedure.

A wide variety of animal models can be used to assess a particular therapeutic composition or treatment regimen for its therapeutic potential. Briefly, peritoneal adhesions have been observed to occur in animals as a result of inflicted severe damage that usually involves two adjacent surfaces. Injuries may be mechanical, due to ischemia, or as a result of the introduction of foreign material. Mechanical injuries include crushing of the bowel and stripping or scrubbing away the outer layers of bowel wall. Dividing major vessels to loops of the intestine induces ischemia. Foreign material that may be introduced into the area includes talcum, gauze sponges, toxic chemicals, bacteria, and feces.

Presently, typical animal models to evaluate prevention of formation of adhesions include the rabbit uterine horn model which involves the abrasion of the rabbit uterus, the rabbit uterine horn devascularization modification model which involves abrasion, devascularization of the uterus, and the rabbit cecal sidewall model which involves the excision of a patch of parietal peritoneum plus the abrasion of the cecum. Those and other reported evaluation models are described herein.

Anti-Connexin Agents

Anti-connexin agents of the invention described herein are capable of modulating (e.g., blocking or inhibiting or down-regulating) or affecting connexin activity and function, connexin complex formation and maintenance, adherens junction formation and maintenance, and cell-cell adhesion. Thus, certain anti-connexin agents described herein modulate cellular adhesion (i.e., cell-to-cell adhesion). Certain anti-connexin agents are adherens junction modulation agents. Such anti-connexin agents are generally targeted to messenger RNA (mRNA) molecules (or the genes encoding them) that, when translated, result in connexin protein synthesis and localization to the cell membrane, where they are available for adherens junction formation. Other anti-connexin agents interfere with connexin complex and/or adherens junction formation. Thus, an anti-connexin agents provided herein may directly or indirectly reduce coupling and communication between cells or reduce or block communication (or the transmission of molecules) between adjoining cells. The connexin is, for example, N-connexin.

Any anti-connexin agent that is capable of eliciting a desired modulation of connexin activity, connexin complex formation, and/or adherens junction formation may be used in practicing the invention. Such compounds include, for example, proteins and polypeptides, polynucleotides, and other organic compounds, and they may, for example, block the function or expression of adherens junctions in whole or in part, or down-regulate the production of one or more connexin proteins, connexin complexes, and/or adherens junctions in whole or in part. Such agents have been described in the scientific and patent literature.

Certain anti-connexin agents provide downregulation of connexin expression (for example, by downregulation of mRNA transcription or translation) or otherwise decrease or inhibit the activity of a connexin protein, a connexin complex, or adherens junctions. In the case of downregulation, this will have the effect of reducing direct cell-cell adhesion mediated by adherens junctions.

Examples of anti-connexin agents include agents that decrease or inhibit expression or function of connexin mRNA and/or protein or that decrease activity, expression, or formation of a connexin protein species, connexin complexes, or adherens junctions. Anti-connexin agents include anti-connexin polynucleotides, such as antisense polynucleotides and other polynucleotides (such as miRNAs and polynucleotides having siRNA or ribozyme functionalities), as well as antibodies and antigen-binding fragments thereof, and peptides and polypeptides, including peptidomimetics and peptide analogs that modulate connexin or adherens junction activity or function, and deoxyribozymes. Anti-connexin agents are, by way of example, anti-N-connexin agents.

Synthesis of antisense polynucleotides and other polynucleotides that can serve as anti-connexin polynucleotides, such as miRNA, RNAi, siRNA, and ribozyme polynucleotides as well as polynucleotides having modified and mixed backbones, is known to those of skill in the art. See e.g. Stein C. A. and Krieg A. M. (eds), Applied Antisense Oligonucleotide Technology, 1998 (Wiley-Liss). Methods of synthesizing desired antibodies and antigen-binding fragments, as well as desired peptides and polypeptides, including peptidomimetics and peptide analogs, are known to those of skill in the art. See e.g. Lihu Yang et al., Proc. Natl. Acad. Sci. U.S.A., 1; 95 (18): 10836-10841 (Sep. 1, 1998); Harlow and Lane (1988) "Antibodies: A Laboratory Manuel" Cold Spring Harbor Publications, New York; Harlow and Lane (1999) "Using Antibodies" A Laboratory Manuel, Cold Spring Harbor Publications, New York.

Connexin binding proteins, including peptides, peptidomimetics, antibodies, antigen-binding antibody fragments, and the like, are also suitable modulators of adherens junctions. Such agents have also been described in the scientific and patent literature.

Anti-connexin agents include peptides comprising an amino acid sequence corresponding to a connexin domain motif from a connexin protein (e.g., E-connexin, N-connexin, etc.). Other embodiments are directed to an anti-connexin agent that is a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids encoded by a connexin gene, for example, an N-connexin gene as set forth in Example 1, below. In certain anti-connexin agents provided herein, the extracellular domains of N-connexin may be used to develop the particular peptide sequences. The peptides need not have an amino acid sequence identical to those portions of naturally occurring N-connexin, and conservative amino acid changes may be made such that the peptides retain binding activity or functional activity. Alternatively, peptides may target other regions of the extracellular domain.

Certain anti-connexin agents described herein are capable of modulation or affecting (e.g. blocking or inhibiting) adhesion between cells. Thus, certain adherens junction modulation agents described herein modulate cellular adhesion. As used herein, "adherens junction modulation agent" broadly includes any agent or compound that prevents, decreases, or modulate, in whole or in part, the activity, function, formation, or stability of an adherens junction. In certain embodiments, an adherens junction modulation agent prevents or decreases, in whole or in part, the function of an adherens junction. Exemplary adherens junction modulation agents may include, without limitation, polynucleotides, polypeptides (e.g. peptiditomimetics, antibodies, binding fragments thereof, and synthetic constructs), and other adherens junction modulating agents.

Dosage Forms and Formulations and Administration

A therapeutically effective amount of each of the agents of the invention may be administered simultaneously, separately, or sequentially and in any order. The agents may be administered separately or as a fixed combination. When not administered as a fixed combination, methods include the sequential administration of a viral VEGF and an anti-inflammatory viral interleukin.

Where a viral VEGF and an anti-inflammatory viral interleukin are administered in combination, either or both may be provided in amounts or doses that are less than those used when the agent or agents are administered alone, i.e., when they are not administered in combination, either physically or in the course of treatment of a wound. Such lesser amounts of agents administered are typically from about one-twentieth to about one-tenth the amount or amounts of the agent when administered alone, and may be about one-eighth the amount, about one-sixth the amount, about one-fifth the amount, about one-fourth the amount, about one-third the amount, and about one-half the amount when administered alone. In certain embodiments, the agents are administered sequentially within at least about one-half hour of each other. The agents may also be administered with about one hour of each other, with about one day to about one week of each other, or as otherwise deemed appropriate.

The agents of the invention of the may be administered to a subject in need of treatment, such as a subject with any of the diseases or conditions mentioned herein. The condition of the subject can thus be improved. A viral VEGF and an anti-inflammatory viral interleukin may thus be used in the treatment of the subject's body by therapy. They may be used in the manufacture of a medicament to treat any of the conditions mentioned herein.

The viral VEGFs and anti-inflammatory viral interleukins of the invention are often used in the various compositions and methods of the invention in a substantially isolated form. It will be understood that the product may be mixed with carriers or diluents that will not interfere with the intended purpose of the product and still be regarded as substantially isolated. A product of the invention may also be in a substantially purified form, in which case it will generally comprise about e.g. at least about 80%, 85%, or 90%, e.g. at least about 95%, at least about 98% or at least about 99% of the protein or dry mass of the preparation.

Depending on the intended route of administration, the pharmaceutical products, pharmaceutical compositions, combined preparations and medicaments of the invention may, for example, take the form of solutions, suspensions, instillations, salves, creams, gels, foams, ointments, emulsions, lotions, paints, sustained release formulations, or powders, and typically contain e.g. about 0.1%-95% of active ingredient(s), and more typically about 0.2%-70%. Other suitable formulations include pluronic gel-based formulations, carboxymethylcellulose (CMC)-based formulations, and hyroxypropylmethylcellulose (HPMC)-based formulations. Suitable formulations including pluronic gel, have for example about 10 to about 15 percent, about 15-20 percent, about 20-25 percent, and about 25-30 percent, suitably about 22 percent, pluronic gel. Other useful formulations include slow or delayed release preparations and instillations.

Gels or jellies may be produced using a suitable gelling agent including, but not limited to, gelatin, tragacanth, alginate, or a cellulose derivative and may include glycerol as a humectant, emollient, and preservative. Ointments are semisolid preparations that consist of the active ingredient incorporated into a fatty, waxy, or synthetic base. Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

In certain embodiments the agents of the invention are combined with a pharmaceutically acceptable carrier or diluent to produce a pharmaceutical composition. Suitable carriers and diluents include isotonic saline solutions, for example phosphate-buffered saline. Suitable diluents and excipients also include, for example, water, saline, dextrose, glycerol, or the like, and combinations thereof. In addition, if desired substances such as wetting or emulsifying agents, stabilizing, or ph buffering agents may also be present.

The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, and amino acid copolymers.

Pharmaceutically acceptable salts can also be present, e.g., mineral acid salts such as hydrochlorides, hydrobromides, phosphates, sulfates, and the like; and the salts of organic acids such as acetates, propionates, malonates, benzoates, and the like.

Suitable carrier materials include any carrier or vehicle commonly used as a base for creams, lotions, gels, emulsions, lotions, or paints for topical administration. Examples include emulsifying agents, inert carriers including hydrocarbon bases, emulsifying bases, non-toxic solvents, or water-soluble bases. Particularly suitable examples include pluronics, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol, honey (including manuka honey), and stearyl alcohol.

In certain embodiments, the pharmaceutically acceptable carrier or vehicle is a gel, suitably a nonionic polyoxyethylene-polyoxypropylene copolymer gel, for example, a Pluronic gel, such as, for example, Pluronic F-127 (BASF Corp.). This gel is particularly useful as it is a liquid at low temperatures but rapidly sets at physiological temperatures, which confines the release of the agent to the site of application or immediately adjacent that site. Pharmaceutical carriers also include liposomes, nanosomes, and the like.

An auxiliary agent such as casein, gelatin, albumin, glue, sodium alginate, carboxymethylcellulose, methylcellulose, hydroxyethylcellulose, or polyvinyl alcohol may also be included in the formulation of the invention.

Other suitable formulations include pluronic gel-based formulations, carboxymethylcellulose (CMC)-based formulations, and hyroxypropylmethylcellulose (HPMC)-based formulations. The composition may be formulated for any desired form of delivery, including topical, instillation, parenteral, intramuscular, subcutaneous, or transdermal administration. Other useful formulations include slow or delayed release preparations.

Transdermal delivery can be carried out by methods known in the art or later discovered, including, for example, methods directed to 1) the use of chemical penetration enhancers or skin enhancers; 2) liposome-mediated delivery; 3) iontophoresis; 4) electroporation; 5) sonophoresis; 6) mechanical (e.g., microporation) devices. Exemplary methods suitable for transdermal delivery of the agents disclosed herein can include, for example, methods directed to enhancing the transport of material across the skin pores by increasing the rate of transport across existing pores or by amplifying the number of available skin pores through the creation of artificial pores.

Transdermal delivery can be carried out by the use of chemical or penetration enhancers, including for example, an pharmaceutically acceptable oil of vegetable, nut, synthetic or animal origin including emu oil, ethoxylated oil, PEG, linoleic acid, ethanol, 1-methanol, and/or agents which delipidize the stratum corneum. Suitable oils include meadowfoam oil, castor oil, jojoba oil, corn oil, sunflower oil, sesame oil, and emu oil, all of which may be optionally ethoxylated. Exemplars include those as described in U.S. Pat. Nos. 7,291, 591, 7,201,919, 7,052,715, 7,033,998, 6,946,144; 6,951,658, 6,759,056, 6,720,001, 6,224,853, 5,695,779, and 6,750,291. In addition, transdermal patches can also be adapted for delivery of dry powder or lyophilized drugs, and exemplars include those described in U.S. Pat. No. 5,983,135.

Transdermal delivery can be carried out by liposome mediated delivery methods (e.g., delivery facilitated by application of lipophilic membrane active agents). Suitable exemplars may include those described in U.S. Pat. Nos. 5,910, 306, 5,718,914, and 5,064,655.

Transdermal delivery systems can also be employed in conjunction or in combination with a wide variety of iontophoresis or electrotransport systems. Illustrative electrotransport drug delivery systems are disclosed in U.S. Pat. Nos. 5,147,296, 5,080,646, 5,169,382, and 5,169,383.

The term "electrotransport" refers, in general, to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent, or, for "reverse" electrotransport, samples or enhances sampling of the agent. The electrotransport of the agents into or out of the human body may be achieved in various manners.

Transdermal delivery can be carried out by iontophoretic methods (e.g., delivery facilitated by application of low level electrical field to the skin over time). Suitable exemplars may include those described in U.S. Pat. Nos. 6,731,987, 6,391,015, 6,553,255, 4,940,456, 5,681,580, and 6,248,349.

Also, transdermal delivery can be carried out by electroporation methods (e.g., delivery facilitated by brief application of high voltage pulse to create transient pores in the skin). Suitable exemplars may include U.S. Pat. Nos. 7,008,637, 6,706,032, 6,692,456, 6,587,705, 6,512,950, 6,041,253, 5,968,006, and 5,749,847.

Transdermal delivery can be carried out by sonophoresis methods (e.g., delivery facilitated by application of pulses of low frequency ultrasound to increase skin permeability). Suitable exemplars may include U.S. Pat. Nos. 7,232,431, 7,004,933, 6,842,641, 6,868,286, 6,712,805, 6,575,956, 6,491,657, 6,487,447, 623,499, and 6,190,315.

Transdermal delivery can be carried out by methods comprising the use of mechanical devices and/or creation of artificial micropores or microchannels (e.g., microprojections) by inducing mechanical alterations or disruptions in the structural elements, thermal stability properties, membrane fluidity and integrity of the dermal architecture and substructures. Suitable exemplars may include MicroPor (Altea Therapeutics), MacroFlux (Alza Corporation), as well as those as described in U.S. Pat. Nos. 6,893,655, 6,730,318, 5,484,604, 5,362,308, 5,320,850, and 5,279,544, and US re-examination certificate RE35474.

Other suitable formulations are formulations that may be inhaled. Still other suitable formulations are formulations that may be injected.

The effective dose for a given subject or condition typically lies within the dose that is therapeutically effective for at least 50% of the population, and that exhibits little or no toxicity at this level.

The effective dosage of each of the viral VEGF and anti-inflammatory mammalian or viral cytokine (e.g., interleukin) (and/or other therapeutic agent(s), if any) employed in the methods and compositions of the invention may vary depending on a number of factors including the particular viral VEGF and anti-inflammatory interleukin employed, the combinational partner (if any), the mode of administration, the frequency of administration, the condition being treated, the severity of the condition being treated, the route of administration, the needs of a patient sub-population to be treated or the needs of the individual patient which different needs can be due to age, sex, body weight, relevant medical condition specific to the patient.

The dose at which a viral VEGF and an anti-inflammatory mammalian or viral cytokine (e.g., interleukin) (and/or other therapeutic agent(s), if any) is administered to a patient will depend upon a variety of factors such as the age, weight and general condition of the patient, the condition that is being treated, and the particular agents being administered.

A suitable therapeutically effective dose of a viral VEGF, for example, may be from about 1 to about 312.5 $\mu g/cm^2$ or about 0.2 to about 40 µMol. A suitable therapeutically effective dose of an anti-inflammatory mammalian or viral cytokine (e.g., interleukin) may be from about 15 ng to about 80 $\mu g/cm^2$, or about or 2 nMol to about 10 µMol.

Doses may be administered in any form, including topically and by injection or instillation. If administered by injection or instillation the dose or doses are administered approximately once per linear centimeter of the tissue target, e.g. a wound.

Doses may be administered daily, or in other regimens, e.g., twice daily, once every other day, once per week and so on. Doses may also be administered or applied daily for from about two to about seven to fourteen days, or any number of days within this range.

Therapeutically effective doses of anti-connexin agent(s) (and/or other therapeutic agent(s), if any) are published in the art.

Alternatively, the dosage of each of a viral VEGF and an anti-inflammatory viral cytokine (e.g., an interleukin) (and/or other therapeutic agent composition(s), if any) in the composition or compositions may be determined by reference to the composition's or compositions' concentration relative to the size, length, depth, area, or volume of the area to which it will be applied. For example, in certain topical applications, dosing of the pharmaceutical compositions may be calculated based on mass (e.g. grams) of or the concentration in a pharmaceutical composition (e.g. µg/ul) per length, depth, area, or volume of the area of application. Useful doses range from about 1 to about 10 micrograms per square centimeter of wound size. Certain doses will be about 1-2, about 1-5, about 2-4, about 5-7, and about 8-10 micrograms per square centimeter of wound size. Other useful doses are greater than about 10 micrograms per square centimeter of wound size, including at least about 15 micrograms per square centimeter of wound size, at least about 20 micrograms per square centimeter of wound size, at least about 25 micrograms per square centimeter of wound size, about 30 micrograms per square centimeter of wound size, at least about 35 micrograms per square centimeter of wound size, at least about 40 micrograms per square centimeter of wound size, at least about 50 micrograms per square centimeter of wound size, and at least about 100 to at least about 150 micrograms per square centimeter of wound size. Other doses include about 150-200 micrograms per square centimeter, about 200-250 micrograms per square centimeter, about 250-300 micrograms per square centimeter, about 300-350 micrograms per square centimeter, about 350-400 micrograms per square centimeter, and about 400-500 micrograms per square centimeter, and 500-1000 micrograms per square centimeter, and at least about 600-1000 micrograms per square centimeter.

In certain embodiments, the viral VEGF and/or anti-inflammatory mammalian or viral cytokine (e.g., interleukin) composition or compositions (and/or other therapeutic agent composition(s), if any) may be applied at about 0.01 micromolar (µM) or 0.05 µM to about 200 µM, or up to 300 µM or up to 400, 500, 600, 700, 800, 900 µM or up to 1000 µM or up to 2000 µM or up to 3200 µM or more final concentration at the treatment site and/or adjacent to the treatment site, and any doses and dose ranges within these dose numbers. In certain embodiments, a viral VEGF and/or anti-inflammatory mammalian or viral cytokine (e.g., interleukin) composition or compositions (and/or other therapeutic agent composition(s), if any) are applied at about 0.05 µM to about 100 µM or more final concentration, more typically, a viral VEGF and/or anti-inflammatory mammalian or viral cytokine (e.g., interleukin) composition or compositions (and/or other therapeutic agent composition(s), if any) is applied at about 1.0 µM to about 50 µM final concentration, and even more typically, at about 5-10 µM to about 30-50 µM final concentration. Additionally, the viral VEGF and/or anti-inflammatory mammalian or viral cytokine (e.g., interleukin)

composition or compositions (and/or other therapeutic agent composition(s), if any) may be applied at about 8 µM to about 20 µM final concentration, and alternatively a viral VEGF and/or anti-inflammatory mammalian or viral cytokine (e.g., interleukin) composition or compositions (and/or other therapeutic agent composition(s), if any) is applied at about 10 µM to about 20 µM final concentration, or at about 10 to about 15 µM final concentration. In certain other embodiments, the viral VEGF and/or anti-inflammatory mammalian or viral cytokine (e.g., interleukin) composition or compositions (and/or other therapeutic agent composition(s), if any) is applied at about 10 µM final concentration. In yet another embodiment, the viral VEGF and/or anti-inflammatory mammalian or viral cytokine (e.g., interleukin) composition or compositions (and/or other therapeutic agent composition(s), if any) is applied at about 1-15 µM final concentration. In other embodiments, the viral VEGF and/or anti-inflammatory mammalian or viral cytokine (e.g., interleukin) composition or compositions (and/or other therapeutic agent composition (s), if any) is applied at about a 20 µM, 30 µM, 40 µM, 50 µM, 60 µM, 70 µM, 80 µM, 90 µM, 100 µM., 10-200 µM, 200-300 µM, 300-400 µM, 400-500 µM, 500-600 µM, 600-700 µM, 700-800 µM, 800-900 µM, 900-1000 or 1000-1500 µM, or 1500 µM-2000 µM or 2000 µM-3000 µM or greater.

Viral VEGF and/or anti-inflammatory mammalian or viral cytokine (e.g., interleukin) dose amounts also include, for example, about 0.1-1, 1-2, 2-3, 3-4, or 4-5 micrograms (µg), from about 5 to about 10 µg, from about 10 to about 15 µg, from about 15 to about 20 µg, from about 20 to about 30 µg, from about 30 to about 40 µg, from about 40 to about 50 µg, from about 50 to about 75 µg, from about 75 to about 100 µg, from about 100 µg to about 250 µg, and from 250 µg to about 500 µg. Dose amounts from 0.5 to about 1.0 milligrams or more or also provided, as noted above. Dose volumes will depend on the size of the site to be treated, and may range, for example, from about 25-100 µL to about 100-200 µL, from about 200-500 µL to about 500-1000 µL. Milliliter doses are also appropriate for larger treatment sites.

Still other dosage levels between about 1 nanogram (ng)/kg and about 1 mg/kg body weight per day of each of the agents described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 0.01 mg per kg body weight, about 0.01 mg to about 0.1 mg per kg body weight, or about 0.1 mg to about 1 mg per kg body weight. In certain embodiments, the dosage of each of the subject compounds will generally be in the range of about 0.001 mg to about 0.01 mg per kg body weight, about 0.01 mg to about 0.1 mg per kg body weight, about 0.1 mg to about 1 mg per kg body weight. If more than one viral VEGF and/or anti-inflammatory mammalian or viral cytokine (e.g., interleukin) is used, the dosage of each viral VEGF and/or anti-inflammatory mammalian or viral cytokine (e.g., interleukin) need not be in the same range as the other. For example, the dosage of one viral VEGF and/or anti-inflammatory mammalian or viral cytokine (e.g., interleukin) may be between about 0.01 mg to about 10 mg per kg body weight, and the dosage of another viral VEGF and/or anti-inflammatory mammalian or viral cytokine (e.g., interleukin) (or other therapeutic agent) may be between about 0.1 mg to about 1 mg per kg body weight.

All doses and dose ranges referenced herein are applicable, for example, to viral VEGFs and/or anti-inflammatory viral cytokines (e.g., interleukins) referenced herein, as well as to polynucleotide therapeutic, including anti-connexin agents that comprise oligonucleotides. These dose ranges are also applicable, for example, to viral VEGFs and/or anti-inflammatory viral cytokines (e.g., interleukins) as well as to therapeutic agents, including anti-connexin agents, that comprise proteins and peptides, as well as mimetic peptides and peptidomimetics.

As noted herein, the doses of a viral VEGF and/or anti-inflammatory mammalian or viral cytokine (e.g., interleukin) composition or compositions (and/or other therapeutic agent composition(s), if any) administered in combination, can be adjusted down from the doses administered when given alone. The combined use of several agents may reduce the required dosage for any individual agent because the onset and duration of effect of the different agents may be complementary. In an embodiment, the combined use of two or more viral VEGFs and/or anti-inflammatory mammalian or viral cytokines (e.g., interleukins) has an additive, synergistic, or super-additive effect. In some cases, the combination of one or more viral VEGFs and/or one or more anti-inflammatory mammalian or viral cytokines (e.g., interleukins) in combination with either or both, have an additive effect. In other cases, the combination can have greater-than-additive effect. Such an effect is referred to herein as a "supra-additive" effect, and may be due to synergistic or potentiated interaction.

The term "supra-additive" refers to a mean acceleration in wound healing, or reduction in inflammation, scarring, fibrosis or adhesion formation produced by administration of a combination of one or more viral VEGFs with one or more anti-inflammatory mammalian or viral cytokines (e.g., interleukins) administered in combination with either or both, and is statistically significantly higher than the sum of the acceleration in wound healing, or reduction in inflammation, scarring, fibrosis or adhesion formation by the individual administration of either of the agents alone. Whether the result is "statistically significantly higher" than the expected additive value of the individual compounds may be determined by a variety of statistical methods as described herein and/or known by one of ordinary skill in the art. The term "synergistic" refers to a type of supra-additive inhibition which, for example, has the ability to accelerate wound healing, or reduce inflammation, scarring, fibrosis or adhesion formation, for example. The term "potentiated" refers to type of supra-additive effect in which the therapeutic agents administered in combination individually have the increased ability to accelerate wound healing, or reduce inflammation, scarring, fibrosis or adhesion formation, by way of example.

In general, potentiation may be assessed by determining whether the combination treatment produces a mean decrease, by way of example, in accelerating wound healing, or reducing inflammation, scarring, fibrosis or adhesion formation in a treatment group that is statistically significantly supra-additive when compared to the sum of the mean decrease in accelerating wound healing, or reducing inflammation, scarring, fibrosis or adhesion formation produced by the individual treatments in their treatment groups respectively. The mean acceleration in or enhancement of or improvement in wound healing, for example, may be calculated as the difference between control group and treatment group mean acceleration in or enhancement of or improvement in wound healing. The fractional acceleration of wound healing, for example, "fraction affected" (Fa), may be calculated by dividing the treatment group mean acceleration in wound healing by control group mean acceleration in or enhancement of or improvement in wound healing. Testing for statistically significant potentiation requires the calculation of Fa for each treatment group. The expected additive Fa for a combination treatment may be taken to be the sum of mean Fas from groups receiving either element of the combination. The Two-Tailed One-Sample T-Test, for example, may be used to evaluate how likely it is that the result obtained by the experiment is due to chance alone, as measured by the p-value. A value of less than 0.05 is considered statistically significant, that is, not likely to be due to chance alone. Thus, Fa for the combination treatment group must be statistically significantly higher than the expected additive Fa for the single element treatment groups to deem the combination as resulting in a potentiated supra-additive effect.

Whether a synergistic effect results from a combination treatment may be evaluated by the median-effect/combination-index isobologram method (Chou, T., and Talalay, P. (1984) Ad. Enzyme Reg. 22:27-55). This analysis may be performed using computer software tools, such as CalcuSyn, Windows Software for Dose Effect Analysis (Biosoft (D, Cambridge UK). Any method known or later developed in the art for analyzing whether a supra-additive effect exists for a combination therapy is contemplated for use in screening for suitable agents for use in combination as described herein.

In another embodiment, the combined use of one or more viral VEGFs with one or more anti-inflammatory mammalian or viral cytokines (e.g., interleukins) reduces the effective dose of any such agent compared to the effective dose when said agent administered alone. In certain embodiments, the effective dose of the agent when used in combination is about $1/15$ to about $1/2$, about $1/10$ to about $1/3$, about $1/8$ to about $1/6$, about $1/5$, about $1/4$, about $1/3$ or about $1/2$ the dose of the agent when used alone.

In another embodiment, the combined use of one or more viral VEGFs with one or more anti-inflammatory mammalian or viral cytokines (e.g., interleukins) reduces the frequency in which said agent is administered compared to the frequency when said agent is administered alone. Thus, these combinations allow the use of lower and/or fewer doses of each agent than previously required to achieve desired therapeutic goals.

The doses may be administered in single or divided applications. The doses may be administered once, or application may be repeated. As indicated above, application may be repeated daily or weekly or more often until, for example, wound healing is promoted, or a repeat application may be made in the event that, for example, wound healing slows or is stalled. Doses may be applied 1-7 days or more apart. In the case of a chronic wound, for example, repeat applications may be made, for example, weekly, or bi-weekly, or daily or in other frequency for example if and when, for example, wound healing slows or is stalled. For some indications, such as certain ocular uses, more frequent dosing, up to hourly may employed.

In combination therapies, the viral VEGF(s) and the anti-inflammatory mammalian or viral cytokine(s) (e.g., interleukin(s)) can be administered by the same or different routes. The various agents can be administered separately at different times during the course of therapy, or concurrently in divided or single combination forms.

In some combination therapy embodiments, the viral VEGF(s) and the anti-inflammatory mammalian or viral cytokine(s) (e.g., interleukin(s)) is/are administered in two or more separate compositions. In some of these embodiments, the first composition is administered before the second composition. In other embodiments, the first composition is administered after the second composition. In still other embodiments, the first composition is administered before and after the second composition. In yet other embodiments, the second composition is administered before and after the first composition. In further such embodiments, the first composition is administered about the same time as the second composition.

In one embodiment, the viral VEGF(s) and the anti-inflammatory viral interleukin(s) is/are delivered by injection (peripherally or directly to a site). In one aspect, the injection is made at or adjacent to a site or wound, e.g., 1-10 mm from the site or wound edge. In other embodiments, the injection is made about 1-8, 1-7, 1-6, 1-5, 1-4, 1-3 and 1-2 mm from the site or wound edge. In still other embodiments, the injection is made about 2-8, 2-7, 2-6, 2-5, 2-4 and 2-3 mm from the site or wound edge. In one embodiment, the injection is made 2-4 or 2-5 mm from the site or wound edge. In sies of administration, including wounds, that have length greater than about 1 cm, the injections are made about once every linear centimeter. In one embodiment the injection in angled in toward a wound or other site of administration, in another embodiment, the injection(s) is/are made into the dermis of a wound, or by intradermal, intra-tissue or intra-organ injection In another embodiment, the viral VEGF(s) and the anti-inflammatory viral interleukin(s) is/are delivered by topical administration (peripherally or directly to a site), including but not limited to topical administration using solid supports (such as dressings and other matrices) and medicinal formulations (such as gels, mixtures, suspensions and ointments). In one embodiment, the solid support comprises a biocompatible membrane or insertion into a treatment site. In another embodiment, the solid support comprises a dressing or matrix. In one embodiment of the invention, the solid support composition may be a slow release solid support composition in which the viral VEGF(s) and the anti-inflammatory mammalian or viral cytokine(s) (e.g., interleukin(s)), alone or in admixture or combination with one or more additional therapeutic agents, is/are dispersed in a slow release solid matrix such as a matrix of alginate, collagen, or a synthetic bioabsorbable polymer. In certain embodiments, the solid support composition is sterile or low bio-burden. In one embodiment, a wash solution comprising a viral VEGF and an anti-inflammatory viral mammalian or viral cytokine (e.g., interleukin) can be used.

The delivery of a formulation of the invention comprising one or more active ingredients, over a period of time, in some instances for about 1-2 hours, about 2-4 hours, about 4-6 hours, about 6-8, or about 12-24 hours or longer, may be a particular advantage in more severe injuries or conditions.

While the delivery period will be dependent upon both the site at which the accelerating wound healing, or reducing inflammation, scarring, fibrosis or adhesion formation is to be induced, continuous or slow-release delivery for about 0.5-1 hour, about 1-2 hours, about 2-4 hours, about 4-6 hours, about 6-8, or about 12-24 hours or longer is provided. In accordance with the present invention, this is achieved by inclusion of a viral VEGF(s) and an anti-inflammatory viral interleukin(s), alone or in combination, in a formulation(s) together with a pharmaceutically acceptable carrier or vehicle, particularly in the form of a formulation for continuous or slow-release administration.

As noted, the viral VEGF(s) and the anti-inflammatory mammalian or viral cytokine(s) (e.g., interleukin(s)) of the invention may be administered before, during, or immediately following wounding, for example, or following a procedure likely or suspected to result in inflammation, a scar, an adhesion, or fibrosis, for example, or within about 180, or about 120, or about 90, or about 60, or about 30 days, but typically, for example, within about 10, about 9, about 8, about 7, about 6, about 5, about 4, about 3, or about 2 days or less, and most typically within about 24, about 12, about 10, about 9, about 8, about 7, about 6, about 5, about 4, about 3, about 2 hours or within about 60, about 45, about 30, about 15, about 10, about 5, about 4, about 3, about 2, about 1 minutes following wounding or following a procedure likely or suspected to result in an adhesion, for example. The one or more agents of the invention may also be administered before and/or during a procedure likely or suspected to result in an adhesion, for example.

The agents and agent combinations of the invention can be administered in any manner that achieves a desired result. Exemplary methods include peritubular administration (either direct application at the time of surgery or with endoscopic, ultrasound, CT, MRI, or fluoroscopic guidance); "coating" the surgical implant; and placement of a drug-eluting polymeric implant at the surgical site. In one embodiment, 0.5% to 20% of the viral VEGF(s) and the anti-inflammatory viral interleukin(s) by weight is loaded into a polymeric carrier and applied to the peritubular (mesenteric) surface as a "paste", "film", or "wrap" which releases the drug over a period of time such that the incidence of surgical adhesions is reduced. During endoscopic procedures, the polymer preparation may be applied as a "spray", via delivery ports in the endoscope, to the mesentery of the abdominal and pelvic organs manipulated during the operation. In another embodiment, the peritubular composition is about 0.1% to about 5% active ingredient by weight. In another embodiment, a polymeric coating containing about 0.1% to about 20% or more of active agent(s) is applied to the surface of the surgical implant (e.g., breast implant, artificial joint, vascular graft, etc.) to prevent encapsulation/inappropriate scarring, for example, in the vicinity of the implant. In yet another embodiment, a polymeric implant containing about 0.01% to about 20% or more of active agent or agents by weight is applied directly to the surgical site (e.g., directly into the sinus cavity, chest cavity, abdominal cavity, or at the operative site during neurosurgery) such that adhesion formation, for example, is prevented or reduced. In one embodiment, one or more active agents can be administered via fluoroscopically guided intra-articular injection.

In another embodiment, lavage fluid containing about 1 to about 100 µg/cm$^2$ (typically about 10 to about 50 µg/cm$^2$) of a viral VEGF(s) and an anti-inflammatory mammalian or viral cytokine(s) (e.g., interleukin(s)) would be used at the time of or immediately following surgery and administered during surgery or intraperitoneally, by a physician. In all of the embodiments, these agents, alone or in combination with other therapeutic agents, would be administered at equivalent doses adjusted for potency and tolerability of the agent.

The routes of administration and dosages described herein are intended only as a guide since a skilled physician will determine the optimum route of administration and may adjust the dosage for any particular patient and condition.

Any of the agents and methods of treating a subject having a disease, disorder or condition referenced or described herein and treating subjects before or following a surgical procedure may utilize the administration of any of the doses, dosage forms, formulations, and/or compositions herein described.

Dressings and Matrices

In one aspect, one or more active agents are provided in the form of a dressing or matrix. In certain embodiments, the one or more agents of the invention are provided in the form of a liquid, semi solid or solid composition for application directly, or the composition is applied to the surface of, or incorporated into, a solid contacting layer such as a dressing gauze or matrix. The dressing composition may be provided for example, in the form of a fluid or a gel. One or more active agents may be provided in combination with conventional pharmaceutical excipients for topical application. Suitable carriers include: Pluronic gels, Poloxamer gels, Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA.

In addition to the biological matrices previously mentioned, suitable dressings or matrices may include, for example, the following with a viral VEGF(s) and an anti-inflammatory mammalian or viral cytokine(s) (e.g., interleukin(s)) (or other active agents to be administered alone or in combination therewith):

1) Absorptives: suitable absorptives may include, for example, absorptive dressings, which can provide, for example, a semi-adherent quality or a non-adherent layer, combined with highly absorptive layers of fibers, such as for example, cellulose, cotton or rayon. Alternatively, absorptives may be used as a primary or secondary dressing.

2) Alginates: suitable alginates include, for example, dressings that are non-woven, non-adhesive pads and ribbons composed of natural polysaccharide fibers or xerogel derived from seaweed. Suitable alginates dressings may, for example, form a moist gel through a process of ion exchange upon contact with exudate. In certain embodiments, alginate dressings are designed to be soft and conformable, easy to pack, tuck or apply over irregular-shaped areas. In certain embodiments, alginate dressings may be used with a second dressing.

3) Antimicrobial Dressings: suitable antimicrobial dressings may include, for example, dressings that can facilitate delivery of bioactive agents, such as, for example, silver and polyhexamethylene biguanide (PHMB), to maintain efficacy against infection, where this is needed or desirable. In certain embodiments, suitable antimicrobial dressings may be available as for example, as sponges, impregnated woven gauzes, film dressings, absorptive products, island dressings, nylon fabric, non-adherent barriers, or a combination of materials.

4) Biological & Biosynthetics: suitable biological dressings or biosynthetic dressings may include, for example, gels, solutions or semi-permeable sheets derived from a natural source, e.g., pigs or cows. In certain embodiments, a gel or solution is applied to the treatment site and covered with a dressing for barrier protection. In another embodiment, a biological-based (e.g., pig intestinal mucosa or bladder tissue) or biosynthetic-based sheet is placed in situ which may act as membrane, remaining in place after a single application, or the may be biological dressings or biosynthetic dressings may be prepared in advance to include the therapeutics agents.

5) Collagens: suitable collagen dressings may include, for example, gels, pads, particles, pastes, powders, sheets or solutions derived from for example, bovine, porcine or avian sources or other natural sources or donors. In certain embodiments, the collagen dressing may interact with treatment site exudate to form a gel. In certain embodiments, collagen dressing may be used in combination with a secondary dressing.

6) Composites: suitable composite dressings may include, for example, dressings that combine physically distinct components into a single product to provide multiple functions, such as, for example, a bacterial barrier, absorption, and adhesion. In certain embodiments, the composite dressings are comprised of, for example, multiple layers and incorporate a semi- or non-adherent pad. In certain embodiments, the composite may also include for example, an adhesive border of non-woven fabric tape or transparent film. In certain other embodiments, the composite dressing may function as for example, either a primary or a secondary dressing and in yet another embodiment, the dressing may be used in combination with topical pharmaceutical composition.

7) Contact Layers: suitable contact layer dressings may include, for example, thin, non-adherent sheets placed on an area to protect tissue from for example, direct contact with other agents or dressings applied to the treatment site. In certain embodiments, contact layers may be deployed to conform to the shape of the area of the treatment site and are porous to allow exudate to pass through for absorption by an overlying, secondary dressing. In yet another embodiment, the contact layer dressing may be used in combination with topical pharmaceutical composition.

8) Elastic Bandages: suitable elastic bandages may include, for example, dressings that stretch and conform to the body contours. In certain embodiments, the fabric composition may include for example, cotton, polyester, rayon, or nylon. In certain other embodiments, the elastic bandage may for example, provide absorption as a second layer or dressing, to hold a cover in place, to apply pressure or to cushion a treatment site.

9) Foams: suitable foam dressings may include, for example, sheets and other shapes of foamed polymer solutions (including polyurethane) with small, open cells capable of holding fluids. Exemplary foams may be for example, impregnated or layered in combination with other materials. In certain embodiments, the absorption capability may be adjusted based on the thickness and composition of the foam. In certain other embodiments, the area in contact with the treatment site may be non-adhesive for easy removal. In yet another embodiment, the foam may be used in combination with an adhesive border and/or a transparent film coating that can serve as an anti-infective barrier.

10) Gauzes & Non-Woven dressings: suitable gauze dressings and woven dressings may include, for example, dry woven or non-woven sponges and wraps with varying degrees of absorbency. Exemplary fabric composition may include, for example, cotton, polyester, or rayon. In certain embodiments, gauzes and non-woven dressing may be available sterile or non-sterile in bulk and with or without an adhesive border. Exemplary gauze dressings and woven dressings may be used for cleansing, packing and covering a variety of treatment sites.

11) Hydrocolloids: suitable hydrocolloid dressings may include, for example, wafers, powders or pastes composed of gelatin, pectin, or carboxymethylcellulose. In certain embodiment, wafers are self-adhering and available with or without an adhesive border and in a wide variety of shapes and sizes. Exemplary hydrocolloids are useful on areas that require contouring. In certain embodiments, powders and pastes hydrocolloids may use used in combination with a secondary dressing.

12) Hydrogels (Amorphous): suitable amorphous hydrogel dressings may include, for example, formulations of water, polymers and other ingredients with no shape, designed to donate moisture and to maintain a moist healing environments and or to rehydrate the treatment site. In certain embodiments, hydrogels may be used in combination with a secondary dressing cover.

13) Hydrogels: Impregnated Dressings: suitable impregnated hydrogel dressings may include, for example, gauzes and non-woven sponges, ropes and strips saturated with an amorphous hydrogel. Amorphous hydrogels may include for example, formulations of water, polymers and other ingredients with no shape, designed to donate moisture to a dry treatment site and to maintain a moist healing environment.

14) Hydrogel Sheets: suitable hydrogel sheets may include for example, three-dimensional networks of cross-linked hydrophilic polymers that are insoluble in water and interact with aqueous solutions by swelling. Exemplary hydrogels are highly conformable and permeable and can absorb varying amounts of drainage, depending on their composition. In certain embodiments, the hydrogel is non-adhesive against the treatment site or treated for easy removal.

15) Impregnated Dressings: suitable impregnated dressings may include, for example, gauzes and non-woven sponges, ropes and strips saturated with a solution, an emulsion, oil, gel or some other pharmaceutically active compound or carrier agent, including for example, saline, oil, zinc salts, petrolatum, xeroform, and scarlet red as well as the compounds described herein.

16) Silicone Gel Sheets: suitable silicone gel sheet dressings may include, for example, soft covers composed of cross-linked polymers reinforced with or bonded to mesh or fabric.

17) Solutions: suitable liquid dressings may include, for example, mixtures of multiprotein material and other elements found in the extracellular matrix. In certain embodiments, exemplary solutions may be applied to the treatment site after debridement and cleansing and then covered with an absorbent dressing or a nonadherent pad.

18) Transparent Films: suitable transparent film dressings may include polymer membranes of varying thickness coated on one side with an adhesive. In certain embodiments, transparent films are impermeable to liquid, water and bacteria but permeable to moisture vapor and atmospheric gases. In certain embodiments, the transparency allows visualization of the treatment site.

19) Fillers: suitable filler dressings may include, for example, beads, creams, foams, gels, ointments, pads, pastes, pillows, powders, strands, or other formulations. In certain embodiments, fillers are non-adherent and may include a time-released antimicrobial. Exemplary fillers may be useful to maintain a moist environment, manage exudate, and for treatment of for example, partial- and full-thickness wounds, infected wounds, draining wounds, and deep wounds that require packing.

Wound Treatment

General Aspects

The present invention is directed to pharmaceutical compositions and their methods of use wherein the composition(s) comprises therapeutically effective amounts of a viral VEGF(s) and an anti-inflammatory mammalian or viral cytokine(s) (e.g., interleukin(s)) (alone or in combination with one or more therapeutic agents). The compositions are useful, for example, in enhancing or promoting healing of wounds, for example, including acute wounds and wounds that do not heal at expected rates, such as chronic wounds and other wounds that may be slow to heal or refractory to conventional wound treatment or wound healing promoting therapies, and other diseases, disorders and conditions described herein, including diseases, disorders and conditions characterized by inflammation or unwanted inflammation. Chronic wounds are often characterized by unwanted inflammation.

Equally, in instances of other tissue damage (particularly wounds) the methods and compositions of the invention are effective in promoting the wound healing process, reducing swelling and inflammation, and in minimizing scar formation. These formations are useful in treating fibrotic diseases, disorders and conditions and in treating, reducing the incidence or severity of or preventing or retarding adhesions, surgical adhesions and/or secondary surgical adhesions. The formulations have clear benefit in the treatment of wounds, whether the result of external trauma (including burns), internal trauma, or surgical intervention, as well as chronic wounds.

Compositions

In one aspect, the invention provides compositions for use in therapeutic wound treatment, which comprises a viral VEGF(s) and an anti-inflammatory mammalian or viral cytokine(s) (e.g., interleukin(s)). In another aspect, the invention provides compositions for use in therapeutic wound treatment, which comprises a viral VEGF(s) and an anti-inflammatory mammalian or viral cytokine(s) (e.g., interleukin(s)) and at least one other therapeutic agent, for example, an anti-connexin agent and/or an anti-osteopontin agent. In certain embodiments, the compositions further comprise a pharmaceutically acceptable carrier or vehicle.

In one embodiment, an anti-connexin agent is selected from a group consisting of: an anti-connexin polynucleotide, an anti-connexin peptide or peptidomimetic, an adherens junction modulator, and a connexin complex modulator for wound treatment. In another embodiment, an anti-osteopontin agent is selected from a group consisting of: an anti-osteopontin polynucleotide, an anti-osteopontin peptide or peptidomimetic for wound treatment.

In other embodiments, an anti-connexin or anti-osteopontin polynucleotide is an antisense polynucleotide. In one form, the composition contains one or more antisense polynucleotides to the mRNA of one connexin protein or one osteopontin protein only. For example, the connexin protein is connexin43. In another form, the composition comprises an anti-connexin peptide or peptidomimetic and an antisense polynucleotide to the mRNA of a connexin or osteopontin protein. Again, the connexin is, for example, connexin43.

Accordingly, in one aspect, the invention provides compositions for use in treating wounds, including chronic and slow or delayed healing wounds. In another aspect, the invention provides compositions for use in treating fibrosis or fibrotic diseases, disorders, or conditions. In an alternate aspect, the invention provides compositions for use in preventing and/or treating abnormal or excessive scarring and/or excessive tissue proliferation and related disorders and conditions. In a further aspect, the invention provides compositions and methods for their use in preventing and/or decreasing adhesions, including surgical adhesions. In a further aspect, the invention provides compositions and methods for their use in preventing and/or decreasing inflammation.

Kits, Medicaments and Articles of Manufacture

Optionally, a viral VEGF(s) and an anti-inflammatory mammalian or viral cytokine(s) (e.g., interleukin(s)), either alone or in combination with one or more other therapeutic agents, may also be used in the manufacture of the medicament.

In one aspect, the invention provides a kit comprising one or more compositions or formulations described. For example, the kit may include a composition or compositions comprising an effective amount of a viral VEGF(s) and an anti-inflammatory mammalian or viral cytokine(s) (e.g., interleukin(s)), either alone or together, and optionally in combination with one or more other therapeutics agents, for example, anti-connexin agent species and/or anti-osteopontin agents.

Articles of manufacture are also provided, comprising a vessel containing a composition or formulation of the invention as described herein and instructions for use for the treatment of a subject. For example, in another aspect, the invention includes an article of manufacture comprising a vessel containing a therapeutically effective amount of one or more anti-connexin agents, either alone or in combination with one or more other therapeutic agents, and instructions for use, including use for the treatment of a subject. In one embodiment, a viral VEGF(s) and an anti-inflammatory mammalian or viral cytokine(s) (e.g., interleukin(s)) are provided in separate vessels. In another embodiment, a viral VEGF(s) and an anti-inflammatory mammalian or viral cytokine(s) (e.g., interleukin(s)) are provided in the same vessel.

In one aspect, the invention provides for a kit for treating wounds, including chronic and slow or delayed healing wounds. In another aspect, the invention provides a kit for treating fibrosis or fibrotic diseases, disorders, or conditions. According to an alternate aspect, the invention provides a kit for preventing and/or treating abnormal or excessive scarring and/or excessive tissue proliferation and conditions comprising one or more of the formulations described. In another aspect, the invention provides a kit for preventing and/or decreasing adhesions comprising one or more compositions or formulations described. In another aspect, the invention provides a kit for preventing and/or decreasing inflammation comprising one or more compositions or formulations described.

Articles of manufacture are provided for preventing and/or treating wounds, including chronic and slow or delayed healing wounds. In another aspect, articles of manufacture are provided for preventing and/or treating fibrosis or fibrotic diseases, disorders, or conditions. Articles of manufacture are also provided for preventing and/or treating abnormal or excessive scarring and/or excessive tissue proliferation and related disorders and conditions. Additional articles of manufacture are provided for preventing and/or decreasing adhesions as described herein. Additional articles of manufacture are provided for preventing and/or decreasing inflammation as described herein.

Treatment

The compositions and formulations of the invention may be used in conjunction or in combination with a composition for promoting the healing of wounds, for example, and can also be used to reduce swelling, inflammation, and/or scarring. The compositions and formulations of the invention may also be used in conjunction or in combination with a composition for promoting and/or improving the healing of acute or chronic wounds, including slow-healing and delayed healing wounds. In one aspect, the wound will be the result of surgery or trauma or underlying medical condition, e.g., diabetes, peripheral edema, vasculitis, or cardiovascular disease.

In one aspect the invention is directed to a method of promoting or improving wound healing in a subject, comprising administering therapeutically effective amounts of a viral VEGF(s) and an anti-inflammatory mammalian or viral cytokine(s) (e.g., interleukin(s)), either alone or in physical combination with each other. In certain embodiments, such administration is effective to reduce inflammation, promote cell migration to accelerate wound closure or otherwise improve healing, and/or to facilitate epithelial growth and surface recovery. In certain embodiments, the administration of one or more compositions of the invention is effective to reduce or prevent scar formation, including abnormal scar formation.

In one aspect the invention is directed to a method of promoting or improving wound healing in a subject, comprising administration of a viral VEGF(s) and an anti-inflammatory mammalian or viral cytokine(s) (e.g., interleukin(s)), alone or together, and optionally in concert with or in combination with one or more other therapeutic agents in an amount effective to improve wound healing.

In yet a further aspect, the invention provides a method of decreasing scar formation and/or improving scar appearance in a patient who has suffered a wound, e.g., a surgical wound (such as in, for example, cosmetic, scar revision, and other surgeries), which comprises the step of administering a viral VEGF(s) and an anti-inflammatory mammalian or viral cytokine(s) (e.g., interleukin(s)), alone or together, and optionally in concert with or in combination with one or more other therapeutic agents in an amount effective to improve healing at and immediately adjacent the site of said wound. Again, the wound may be the result of trauma or surgery, for example, with the formulation being applied to the wound immediately prior to surgical repair and/or closure thereof. As noted herein, in methods to reduce or improve scar formation or appearance, or prevent or reduce inflammation, a viral VEGF(s) and an anti-inflammatory mammalian or viral cytokine(s) (e.g., interleukin(s)), may be administered in combination with, or after or prior to, administration of a suitable amount of another wound healing agent, for example, an anti-connexin agent or anti-osteopontin agent.

In one aspect the invention is directed to a method of reducing, preventing, or ameliorating tissue damage (including inflammation damage) in a subject, comprising administration of a viral VEGF(s) and an anti-inflammatory mammalian or viral cytokine(s) (e.g., interleukin(s)), alone or together, and optionally in concert with or in combination with one or more other therapeutic agents in an amount effective to reduce, prevent, or ameliorate tissue damage (including inflammation damage).

In a further aspect, the invention is directed to a method of reducing swelling and/or inflammation, for example as part of treating an acute or chronic wound and/or tissue (including tissue subjected to physical trauma) which comprises the step of administering a viral VEGF(s) and an anti-inflammatory mammalian or viral cytokine(s) (e.g., interleukin(s)), alone or together, and optionally in concert with or in combination with one or more other therapeutic agents, to or proximate to said wound or tissue. In one embodiment the wound is the result of physical trauma to tissue, including dermal tissue (leading, for example, to a pressure ulcer or diabetic ulcer or other ulcer) and neuronal tissue such as the brain, spinal cord, or optic nerve, or skin or eye.

In one aspect the invention is directed to sustained administration of a viral VEGF(s) and an anti-inflammatory mammalian or viral cytokine(s) (e.g., interleukin(s)), either alone or in combination with one or more other therapeutic agents, for example, one or more anti-connexin agents and/or anti-osteopontin agents. In one embodiment, the agent or agents are administered for at least at least about 0.5 hours, about 1-24 hours, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours or at least about 24 hours. According to one embodiment, the wound is a chronic wound. Suitable subjects include a diabetic subject. Other subjects include, for example, those with peripheral edema, vasculitis, or cardiovascular disease. Other subjects include, for example, those with venous disease, including venous insufficiency, or arterial disease, including arterial insufficiency.

In one aspect, the present invention provides a method of treating a subject having a wound that comprises sustained administration of an effective amount of a viral VEGF(s) and an anti-inflammatory mammalian or viral cytokine(s) (e.g., interleukin(s)), either alone or in combination with one or more other therapeutic agents, for example, one or more anti-connexin agents and/or anti-osteopontin agents, to the wound.

In another aspect, methods for treating a subject having a chronic wound are provided. Such methods include administering to the subject a viral VEGF(s) and an anti-inflammatory mammalian or viral cytokine(s) (e.g., interleukin(s)), either alone or in combination with one or more other therapeutic agents, for example, one or more anti-connexin agents and/or anti-osteopontin agents.

In one aspect the invention is directed to a method for treatment or prophylaxis of a chronic wound comprising administering to a subject in need thereof an effective amount of a viral VEGF(s) and an anti-inflammatory mammalian or viral cytokine(s) (e.g., interleukin(s)), either alone or in combination with one or more other therapeutic agents, for example, one or more anti-connexin agents and/or anti-osteopontin agents. In one embodiment, the chronic wound is a chronic skin wound and a composition of the present invention is administered to the skin or a tissue associated with the skin of said subject for an effective period of time. A chronic skin wound suitable for treatment may, for example, be selected from the group consisting of pressure ulcers, diabetic ulcers, venous ulcers, arterial ulcers, vasculitic ulcers, and mixed ulcers, and other noted herein. The chronic wound may be an arterial ulcer, which comprises ulcerations resulting from complete or partial arterial blockage. The chronic wound may be a venous stasis ulcer, which comprises ulcerations resulting from a malfunction of the venous valve and the associated vascular disease. The chronic wound may be a trauma-induced ulcer. The chronic, slow- or delayed-healing wound may be, for example, dermal or ocular, associated with another organ tissue (e.g., kidney, bowel, liver, lung), or in the CNS.

When not administered as a fixed combination, certain combination therapy methods include the sequential administration of a viral VEGF(s) and an anti-inflammatory mammalian or viral cytokine(s) (e.g., interleukin(s)), optionally in combination with one or more other therapeutic agents, for example, one or more anti-connexin agents and/or anti-osteopontin agents. For example, the agents are administered sequentially within at least about one-half hour of each other. The agents may also be administered with about one to 12 hours of each other, within about 12 to 24 hours of each other, within about one day to about one week of each other, or as otherwise deemed appropriate.

In one embodiment the method for treatment or prophylaxis of a chronic wound comprises sustained administration of a viral VEGF(s) and an anti-inflammatory mammalian or viral cytokine(s) (e.g., interleukin(s)), either alone or in combination with one or more other therapeutic agents, for example, one or more anti-connexin agents and/or anti-osteopontin agents. In one embodiment, the composition or compositions are administered in a sustained release formulation. In another embodiment, the composition or compositions are administered for a sustained period of time. Subjects that may be treated include diabetic subjects, and patients with other ulcers, including venous ulcers and others described herein and known in the art.

In one aspect the invention is directed to a method of preventing and/or treating fibrosis or fibrotic diseases, disorders or conditions in a subject, comprising administration a therapeutically effective amount of a composition according to the invention. In certain embodiments, the administration is effective to reduce fibrosis. In certain embodiments, the administration is effective to prevent or reduce contracture.

In one aspect the invention is directed to a method of preventing and/or treating fibrosis or fibrotic diseases, disorders, or conditions in a subject, comprising administration of a therapeutically effective amount of a viral VEGF(s) and an anti-inflammatory mammalian or viral cytokine(s) (e.g., interleukin(s)), either alone or together in combination, and optionally in combination with one or more other therapeutic agents, for example, one or more anti-connexin agents and/or anti-osteopontin agents, effective to reduce fibrosis. In one embodiment, administration of a viral VEGF(s) and an anti-inflammatory mammalian or viral cytokine(s) (e.g., interleukin(s)), either alone or together in combination, and optionally in combination with one or more other therapeutic agents, is effective to prevent or reduce contracture.

According to one embodiment of the method, the subject has a disorder selected from the group consisting of scleroderma, kidney fibrosis (including diabetic nephropathy), cardiac fibrosis (e.g. myocardial fibrosis), pulmonary fibrosis (e.g., glomerulosclerosis pulmonary fibrosis, idiopathic pulmonary fibrosis, silicosis, asbestosis, interstitial lung disease and fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fascilitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myleoid leukemia, acute myelogenous leukemia, myelodysplastic syndrome, myeloproferative syndrome, gynecological cancer, Kaposi's sarcoma, Hansen's disease, collagenous colitis and acute fibrosis. According to this embodiment, the scleroderma may be morphea, generalized morphea, or linear scleroderma. Also according to this embodiment, the kidney fibrosis may be glomerular sclerosis, renal tubulointerstitial fibrosis or progressive renal disease. Further to this embodiment, the pulmonary fibrosis may be diffuse interstitial pulmonary fibrosis.

According to another embodiment of the method, the fibrosis is acute fibrosis. The acute fibrosis may be in response to various forms of trauma including accidental injuries, infections, radiation or chemotherapy treatments.

According to another embodiment of the method, the fibrosis is chronic fibrosis. The invention also includes methods for treating and/or preventing, in whole or in part, various diseases, disorders and conditions, including, for example, capsular contracture, Dupytren's contracture, Volkmann's contracture, Ledderhose's contracture, Peyronie's contracture or recurrence thereof, comprising administering effective amounts of a viral VEGF(s) and an anti-inflammatory mammalian or viral cytokine(s) (e.g., interleukin(s)), either alone or together in combination, and optionally in combination with one or more other therapeutic agents. In certain embodiments, the composition is administered to the site of the injury before, at the time of and/or after a release procedure (e.g., forced manipulation, open release, arthroscopic release, or debulking of scar) to prevent the recurrence of scarred and abnormal tissue and/or further contracture.

In one aspect the invention is directed to a method of for preventing and/or treating abnormal or excessive scarring and/or excessive tissue proliferation and related disorders and conditions in a subject, comprising administration of therapeutically effective amounts of a viral VEGF(s) and an anti-inflammatory mammalian or viral cytokine(s) (e.g., interleukin(s)), either alone or together in combination, and optionally in combination with one or more other therapeutic agents. In certain embodiments, the administration is effective to reduce abnormal or excessive scarring and/or excessive tissue proliferation and related disorders and conditions.

In one aspect the invention is directed to a method of for preventing and/or treating abnormal or excessive scarring and/or excessive tissue proliferation and related disorders and conditions in a subject, comprising administration of therapeutically effective amounts of a viral VEGF(s) and an anti-inflammatory mammalian or viral cytokine(s) (e.g., interleukin(s)), either alone or together in combination, and optionally in combination with one or more other therapeutic agents. In one embodiment, the viral VEGF and the anti-inflammatory mammalian or viral cytokine (e.g., interleukin), either alone or together in combination, and optionally in combination with one or more other therapeutic agents, is effective to reduce abnormal or excessive scarring and/or excessive tissue proliferation and related disorders and conditions.

In one aspect the invention is directed to sustained co-administration of a viral VEGF and an anti-inflammatory mammalian or viral cytokine (e.g., interleukin), either alone or together in combination, and optionally in combination with one or more other therapeutic agents.

According to one embodiment, the subject has an abnormal scar selected from the group consisting of keloid scars, hypertrophic scars, widespread scars, and atrophic scars.

According to another embodiment, the subjects to be treated include those having experienced trauma, surgical intervention, burns, and other types of injuries that lead, or can lead, to abnormal or excessive scarring, as well as excessive scar formation and other types of abnormal proliferation of tissue, including keloid scars, hypertrophic scars, widespread scars, and atrophic scars.

In certain embodiments, a viral VEGF(s) and an anti-inflammatory mammalian or viral cytokine(s) (e.g., interleukin(s)), either alone or together in combination (and optionally in combination with one or more other therapeutic agents), is administered to epithelial, connective, muscle, and nerve tissue or other tissue exposed or wounded during surgery or as a result of trauma. In some embodiments, the viral VEGF and the anti-inflammatory viral interleukin are administered topically. In other embodiments, the viral VEGF and the anti-inflammatory mammalian or viral cytokine (e.g, interleukin) are is implanted or instilled or injected.

In certain embodiments, the invention comprises a method of use of the compositions described herein in treating a disease or condition correlated with aberrant or undesired connexin activity, wherein the disease or condition optionally is selected from the group consisting of an acute wound, a chronic wound, an inflammatory disease, a lung diseases (optionally asthma), a renal disease, a liver diseases (optionally NASH), arthritis (optionally juvenile arthritis, osteoarthritis, and rheumatoid arthritis), an inflammatory bowel disease (optionally Crohn's disease and ulcerative colitis), a dermatosis, an infection, ischemia (optionally a reperfusion injury), and a cardiac disease (optionally atherosclerosis).

The following examples which will be understood to be provided by way of illustration only and not to constitute a limitation on the scope of the invention.

EXAMPLES

Example 1

Preparation of Therapeutic Proteins and Experimental Procedures

Recombinant Proteins

Recombinant FLAG-tagged VEGF-A and VEGF-E (ORFV$_{NZ2}$VEGF), and murine (m) IL-10 and orf virus IL-10 (vIL-10) were expressed in 293-EBNA cells, purified and quantitated as previously described (Wise et. al., *J Biol Chem* 278, 38004-38014, 2003, Imlach et. al., *J Gen Virol* 83, 1049-1058, 2002).

Mice

Specific Pathogen Free female C57BL/6 mice (6-8 weeks of age) were obtained from the University of Otago Animal Facility and were used with institutional ethical approval.

Wound Healing Assay

On day 0, mice were anesthetized by subcutaneous (SC) injection of ketamine/domitor/atropine (75/1/0.05 mg/kg body weight, respectively), the dorsum shaved, depilated with Veet cream (Reckitt Benckiser) and cleaned with saline. Two full-thickness excisional wounds were made on each animal, one on each flank, using a sterile, disposable, 4-mm-diameter biopsy punch (Kruuse). Mice were given SC injections of Bupivacaine (2 mg/kg body weight) for pain relief and Strepsin to prevent wound infection. Mice were revived by SC injection of Antisedan (5 mg/kg body weight) then returned to their cages and kept warm by placing the cages on a heating pad until mobile. Each wound was digitally photographed at the indicated time intervals. Changes in the wound were measured (wound diameter across four points) using a digital caliper and expressed as a percentage of the original wound. Wounds were considered closed when completely covered by the epidermis. On day 2, the mice were divided into 8 groups. The seven treatment groups were administered VEGF-A or VEGF-E (1 µg in 50 µL phosphate-buffered saline (PBS)), mIL-10 or vIL-10 (100 ng in 50 µL PBS), VEGF-A and mIL-10 (1 µg and 100 ng, respectively, in 50 µL PBS), VEGF-A and mIL-10 (1 µg and 100 ng, respectively, in 50 µL PBS), or PBS alone by a single SC injection adjacent to the wound (about 3 mm away, and angled toward the wound) on each flank (2 wounds from 4 mice per group). Each group of mice received boost injections of identical treatments to each wound on days 4, 6 and 8. The final group was left untreated. Four mice from each group were euthanized on each of days 3, 6, 9 and 16.

Skin biopsies of 1 cm² around each wound were excised with sharp scissors then divided in half along the narrowest diameter. On day 16 the inside of each wound was cleaned then photographed following its excision. Half of each wound was fixed in 0.5% zinc salts solution and processed into paraffin wax. Six 4 µm serial sections were taken from the fixed blocks approximately 50 µm apart. The remaining wounds from each group were combined into two samples (4 left side and 4 right side) then stored in RNAlater RNA Stabilization Reagent (Qiagen) following the manufacturer's instructions.

Histological Analyses

Serial sections were stained with MSB trichrome and digital photographs were taken of the entire section and were converted into panoramas using Photoshop.

Image J was used to measure the area of the neo-epidermis and the granulation tissue (neo-dermis), and the length of epidermal projections (rete ridges) into the dermis, and the width and total area wound in each section. Collagen content was assessed using RGB Measure (intensity of blue staining at individual pixels) and was normalized to that of unwounded skin stained at the same time. Re-epithelialization was calculated as the percentage of total wound width covered by neo-epidermis. Dermal closure was calculated as the percentage of total wound area covered by granulation tissue. The average epidermal or granulation tissue area, percentage re-epithelialization, rete ridge number or length from 6 serial sections from 2 wounds from 4 different animals was used for analysis.

Vascularization within the granulation tissue was quantitated using a grid overlaying the neo-dermis, avoiding glands and hair follicles. The grid was divided by equidistant lines 0.024 mm apart. The points at which stained blood vessels crossed the intersecting points of the grids were counted (with each vessel counted only once) and the areal fraction of vascularized neo-dermis was expressed as the fraction of the intersecting points on which stained cells fell. The average areal fraction vascularization was determined from 6 serial sections from 2 wounds from 4 different animals.

Immuno-Fluorescent Analysis

Immuno-fluorescent staining followed standard methodology. Briefly, representative sections were incubated with one or more primary antibody (anti-mouse F4/80 antigen AlexaFluor®488 (PAB49, eBioscience, 1:100 dil, anti-α-smooth muscle actin (αSMA) Cy3 conjugate (PAB53, Sigma-Aldrich, dilution 1:400), anti-vimentin XP® 488 conjugate (D21H3, Cell Signalling technology, dilution 1:100) or polyclonal rabbit anti-human von Willebrand Factor (vWF, PAB52, DakoCytomation, dilution 1:200) in tris buffered saline (TBS) for 2 h at room temperature (RT). Following this and subsequent antibody incubations, slides were washed for 15 min in TBS. Slides incubated with the anti-vWF polycolonal were then incubated with goat anti-rabbit IgG AlexaFluor®488 (SAB10, Invitrogen, 1:500 dilution) in TBS for 2 h at RT. 4',6-diamidino-2-phenolindole (DAPI, D3571, Invitrogen, 75 nM) was also added to the slide for the final 30 min of the antibody incubation. Slides were mounted with SlowFade Gold anti-fade reagent (S36936, Invitrogen) then visualized using a fluorescent microscope. Digital photographs were taken of the entire section using the red and green filters, with the white balance adjusted so the background fluorescence appears yellow. Images were subsequently merged and converted into panoramas using Photoshop.

The number of F4/80$^{+ve}$ macrophages per wound was quantitated within the dermal and hypodermal areas 0.57 mm either side of the wound edges. The number of vWF$^{+ve}$ endothelial cells and those associated with αSMA$^{+ve}$ pericytes and the number of red blood cells within the granulation tissue area was quantitated in the neo-dermis, avoiding glands and hair follicles. Results are expressed as the average number of stained cells/1000 µm² and were determined using a representative section from 2 wounds from 4 different animals. The intensity of α-SMA staining was quantitated within the granulation tissue using Adobe Photoshop. Results are expressed as the mean total α-SMA intensity (mean red pixel intensity X number of pixels) and were determined using a representative section from two wounds from four different animals.

Quantitative RT-PCR

Mouse skin was placed in liquid nitrogen, ground thoroughly with a mortar and pestle then homogenized using a needle and syringe. Total RNA was then isolated by Trizol purification (Invitrogen) followed by Proteinase K digestion then further purified step using the RNeasy® Mini Kit (Qiagen), in each case following the manufacturer's instructions. Synthesis of cDNA was carried out with total RNA, oligo(dT)$_{15}$ and random hexamer primers using Superscript III (Invitrogen) following the manufacturer's instructions. Real-time quantitative PCR was carried out in an ABI PRISM 7700 Sequence Detection System using the SYBR® Green PCR Master Mix (Applied Biosystems) following the manufacturer's instructions. The PCR primer sets were from the literature, qPrimerDepot (primerdepot.nci.nih.gov/) or designed using the LUX™ Designer software from Invitrogen to give amplicons from 87 to 129 bp. Primer efficiencies were determined and quantitative RT-PCR data analyses were performed as described in PE Applied Biosystems User Bulletin #2, 1997.

Measurements of Scar Resolution

The scars on the wounded flank of each mouse were photographed at day 13 (eight per group) then scored blind by six independent observers. A scale of 1:5 was used where one represented a fully resolved wound while five denoted that an obvious scar remained. The external scar score represented the mean score from six observers for the eight wounds per treatment group.

The scars on the wounded flank of each mouse were also photographed at day 16, on the hair-free inside of the skin where they were most visible. The scar area was then measured blind using Image J software by two independent observers. Internal scar areas represent the mean area of two wounds from four animals per treatment group and were consistent between observers.

Statistical Analyses

Statistical analysis of the data obtained from each assay was performed using analysis of variance (single factor ANOVA) with significant points of difference (P≤0.05) determined using the Bonferroni Method.

Example 2

Treatment with Viral VEGF and Viral IL-10 Accelerates Wound Closure

Treatment with a combination of viral VEGF-E and viral IL-10 accelerates wound closure to a greater extent than the individual treatments or their mammalian equivalents.

The ability of the viral factors to regulate tissue repair in a mouse model of cutaneous wound healing was examined in this Example. Excisional wounds were treated on days 2, 4, 6 and 8 by subcutaneous (SC) injection of equal doses of the viral or mammalian VEGFs, or IL-10s, alone or in combination and were compared to untreated or mock-treated wounds.

Figure 2:
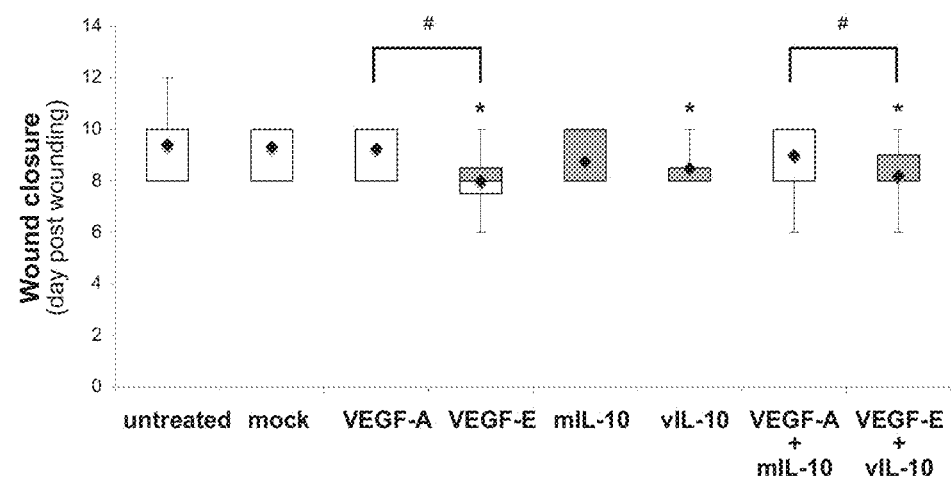
FIG. 2. Combination treatment of viral VEGF-E and viral IL-10, like the individual treatments, accelerates wound closure to a greater extent than their mammalian equivalents. The mean day of closure for each treatment group (n=8) is indicated with a diamond. Upper and lower quartiles are shown with an open and filled box respectively. Outliers are indicated above and below. Values significantly less than mock-treated wounds ($P \leq 0.05$) are indicated by an asterisk. Significant differences between certain treatments are indicated with a hash.

Photographs taken at the indicated time points during wound healing and measurement in wound size revealed differences in healing kinetics and the time to wound closure between the treatment groups (FIG. 1). Mock treatment of wounds with SC injection of PBS induced a significant reduction in wound size at day 8 compared to untreated wounds but this did not translate to a significant increase in the time till wound closure (FIG. 2; day 9.3 vs day 9.4).

Treatment with either mammalian or viral VEGF induced a significant reduction in wound size at day 6 compared to mock-treated wounds, while viral VEGF (here, VEGF-E) treatment continued to induce a significant reduction in wound area at day 8. VEGF-E-treated wounds also closed significantly faster than VEGF-A-treated wounds (FIG. 2; day 8.0 vs day 9.25).

Treatment with either mammalian or viral IL-10 also induced a significant reduction in wound size at day 6 compared to mock-treated wounds, while viral IL-10 treatment continued to induce a significant reduction in wound area at day 8. Viral IL-10-treated wounds also closed faster than mIL-10-treated wounds (FIG. 2; day 8.5 vs day 8.75).

Treatment of wounds with VEGF-A and mIL-10 did not further reduce wound size or accelerate wound closure compared to treatment with either factor alone.

Treatment of wounds with VEGF-E and vIL-10 did however enhance early wound closure over the individual treatments with a significant reduction in wound size at day 4. Treatment with VEGF-E and vIL-10 induced a significant reduction in wound size from day 4 compared with mock-treated wounds. Wounds treated with the viral combination were smaller than wounds treated with the mammalian equivalents from day 4 with a significant difference at day 8. In addition the wounds treated with VEGF-E and vIL-10 closed significantly faster than the wounds treated with their mammalian equivalents (FIG. 2; day 8.2 vs day 9.0).

These results demonstrate that treatment of wounds with VEGF or IL-10, from a mammalian or viral source, reduces wound size. In addition, treatment with the viral factors resulted in accelerated wound closure. Combining the viral VEGF and viral IL-10 enhanced early wound closure over that of the individual factors.

Example 3

Treatment with Viral VEGF and Viral IL-10 Enhances Epidermal Regeneration

Treatment with the combination of VEGF and IL-10 enhances epidermal regeneration over that of treatment with the factors alone.

This Example was carried out to determine if the accelerated wound closure observed in wounds treated with the viral factors was due to enhanced re-epithelialization. On various days post wounding, the skin surrounding each wound was excised and the neo-epidermis was analyzed histologically or by quantitative RT-PCR.

The direct effect of a single treatment of viral or mammalian VEGFs, or IL-10s, alone or in combination, on the wound neo-epidermis was investigated by MSB trichrome staining of sections from treated and untreated wounds after 3, 6 and 9 days. Representative sections shown in FIG. 3A illustrate that VEGF-E and VEGF-A treatment increased wound re-epithelialization compared with the control wounds. Re-epithelialization was then quantitated by determining the percentage of total wound width covered by neo-epidermis as illustrated in FIG. 3B. By day 3 the epidermis covered 53% of the wound bed in wounds treated with VEGF-E, which was significantly greater than the percentage re-epithelialization seen in mock-treated and untreated wounds (33% and 31%, respectively, P≤0.05, FIG. 3C). VEGF-A-treated wounds showed a similar level of re-epithelialization (45%, FIG. 3C) to that of VEGF-E-treated wounds at day 3. Treatment of wounds with VEGF-E continued to significantly increase wound re-epithelialization by day 6, with the epidermis covering 99% of the wound bed compared with the mock-treated and untreated wounds (81% and 82%, respectively, P≤0.05, FIG. 3C). At day 6, VEGF-A-treated wounds showed significantly less re-epithelialization (86%, P≤0.05, FIG. 3C) than that of VEGF-E-treated wounds. By day 9, all wounds showed 100% re-epithelialization (FIG. 3C). Overall at day 3, the neo-epidermis of wounds treated with VEGF-E had an area of 5026 $\mu m^2$, which was significantly greater than the areas of the mock-treated and untreated wounds (2798 µm² and 2663 µm², respectively, P≤0.05, FIG. 3D). The area of neo-epidermis seen in VEGF-E-treated wounds was also significantly greater than that of VEGF-A-treated wounds (4270 µm², P≤0.05, FIG. 3D). By day 6, the area of neo-epidermis of VEGF-E-treated wounds had increased to 7795 µm², which was significantly greater than the areas of the mock-treated and untreated wounds (5991 µm² and 6067 µm², respectively, P≤0.05, FIG. 3D). At day 6, the neo-epidermis of VEGF-A-treated wounds was of a similar area (8046 µm², P≤0.05, FIG. 3D) to that of VEGF-E-treated wounds. At day 9, the areas of the neo-epidermis in wounds treated with VEGF-E or VEGF-A had reduced in size (5231 µm² and 5619 µm², respectively, FIG. 3D), but were still significantly greater than the areas of mock-treated and untreated wounds (P≤0.05, 2815 µm² and 4252 µm², respectively, FIG. 3D).

Treatment of wounds with either IL-10 significantly increased wound re-epithelialization at day 3, compared with the control wounds, with the epidermis covering 46% and 50% of the wound bed in wounds treated with vIL-10 and mIL-10, respectively (P≤0.05, FIG. 3A, C). Treatment of wounds with either IL-10 continued to increase wound re-epithelialisation significantly by day 6, with the epidermis covering 97.0 and 98.1% of the wound bed, in wounds treated with vIL-10 and mIL-10, respectively (P≤0.05, FIG. 3C). At day 3 the neo-epidermal area of wounds treated with vIL-10 and mIL-10 had significantly increased to 4619 µm² and 4583 µm², respectively (P≤0.05, FIG. 3D). By day 6, the area of neo-epidermis had increased in vIL-10- and mIL-10-treated wounds to 5875 µm² and 5438 µm², respectively, but was now similar in area to those of mock-treated and untreated wounds (FIG. 3D). At day 9, the areas of the neo-epidermis in IL-10-treated wounds had decreased in size, but the neo-epidermal area in mIL-10-treated wounds was significantly smaller than that of mIL-10-treated wounds (2649 µm² and 5619 µm², respectively, FIG. 3D). The neo-epidermal area of mIL-10 treated wounds was similar to that of untreated skin (2815 µm², FIG. 3D), while the area of vIL-10 treated wounds was similar to mock-treated wounds (4252 µm², FIG. 3D).

Treatment of wounds with the combination of VEGF and IL-10 also significantly increased wound re-epithelialization at day 3, compared with the control wounds, with the epidermis covering 74% and 70% of the wound bed in wounds treated with VEGF-E and vIL-10 or VEGF-A and mIL-10, respectively (P≤0.05, FIG. 3A, C). Wounds treated with either VEGF and IL-10 combination also showed a significantly greater level of re-epithelialization at day 3 than that of wounds treated with either VEGF or IL-10 alone (P≤0.05, FIG. 3C). Treatment of wounds with either VEGF and IL-10 combination continued to increase wound re-epithelialisation significantly by day 6, with the epidermis covering 95.9 and 98.2% of the wound bed, in wounds treated with VEGF-E and vIL-10 or VEGF-A and mIL-10, respectively (P≤0.05, FIG. 3C). Wounds treated with either VEGF and IL-10 combination did not have a significantly greater level of re-epithelialization at day 6 than that of wounds treated with either VEGF or IL-10 alone (FIG. 3C). At day 3 the average area of the neo-epidermis of wounds treated with VEGF-E and vIL-10 or VEGF-A and mIL-10 had significantly increased to 7950 µm² and 7988 µm², respectively (P≤0.05, FIG. 3D). The area of neo-epidermis seen in wounds treated with either VEGF and IL-10 combination was significantly greater than that of wounds treated with the VEGF or IL-10 alone (P≤0.05, FIG. 3D). By day 6, the area of neo-epidermis had decreased in VEGF-E and vIL-10 or VEGF-A and mIL-10-treated wounds to 5515 µm² and 5663 µm², respectively, but was now similar in area to those of mock-treated and untreated wounds (FIG. 3D). At day 9, the areas of the neo-epidermis in combination-treated wounds had decreased in size, with neo-epidermal areas of 2780 µm² and 3247 µm² in VEGF-E and vIL-10 or VEGF-A and mIL-10-treated wounds, respectively (FIG. 3D). The neo-epidermal area of combination-treated wounds were significantly less than that of mock-treated skin (FIG. 3D).

These results demonstrate that treatment of wounds with VEGF or IL-10, from a mammalian or viral source, increases the area of the neo-epidermis and the rate of wound re-epithelialization. Continued treatment of wounds with VEGF, from a mammalian or viral source, resulted in epidermal hyperplasia. Combining either VEGF with its respective IL-10 however decreased this effect, and limited the epidermal hyperplasia induced by the individual VEGF treatments.

Example 4

Treatment with Viral VEGF and Viral IL-10 Enhances Epidermal Regeneration

Treatment with the combination of VEGF and IL-10 enhances epidermal regeneration to a greater extent than the VEGF treatments alone.

The effect of repeat treatments of viral or mammalian VEGFs, or IL-10s, alone or in combination, on the wound neo-epidermis was investigated by MSB trichrome staining of sections from treated and untreated wounds after 9 days. Representative sections, shown in FIG. 4A, illustrate the increased epidermal hyperplasia and rete ridge formation observed in the VEGF-treated wounds. VEGF-treated wounds showed a significant increase in rete ridge length (VEGF-E; 37.1 µm and VEGF-A, 32.5 µm, FIG. 4C) compared with the rete ridges in mock-treated and untreated wounds (25.9 µm and 21.36 µm, respectively, P≤0.05, FIG. 4B).

Wounds treated with vIL-10 or mIL-10 did not show an increase in rete ridge length (23.1 µm and 23.2 µm, respectively FIG. 4B).

Wounds treated with VEGF-E and vIL-10 or VEGF-A and mIL-10 also did not differ from control wounds in rete ridge length (23.1 µm and 24.4 µm, respectively, FIG. 4B).

These results demonstrate that repeat treatment of wounds with VEGF, from a mammalian or viral source, increases the projection of rete ridges into the dermis. Combining either VEGF with its respective IL-10 however decreased this effect, thereby limiting the epidermal hyperplasia induced by the individual VEGF treatments.

Example 5

Treatment with Viral VEGF and Viral IL-10 Alters the Timing of Key Regulators of Epidermal Repair In this Example, the effect of treatments with VEGF and IL-10 combinations on key regulators of wound re-epithelialization and resolution was examined. The effect of the treatments on expression of growth factors and gap junction proteins known to regulate epidermal proliferation, differentiation or communication was examined in the treated and untreated wounds using quantitative real-time (RT)-PCR.

Connexin43 is expressed in the wounded epidermis and has implicated in the control of keratinocyte proliferation and wound closure (Goliger and Paul, *Mol Biol Cell,* 6, 1491-501, 1995; Mori et al., *J Cell Sci,* 119, 5193-203, 2006; Qiu et al. *Curr Biol,* 13, 1697-703, 2003). Connexin43 expression was increased in wounded skin by day 3 and from days 9-16 (FIG.

5A-B). Treatment of wound with VEGF-A or VEGF-E had little effect on connexin43 expression at day 3 compared with mock-treated wounds, while connexin43 expression was reduced in wounds treated with mIL-10 or vIL-10 (FIG. 5A). Treatment of wounds with VEGF-E and vIL-10 also decreased the expression of connexin43 at day 3 but then increased its expression from day 9 (FIGS. 5A-B). In contrast, treatment with VEGF-A and mIL-10 increased the expression of connexin43 over that of mock-treated wounds at all time points (FIG. 5A-B).

BMP-6 promotes the differentiation of keratinocytes while inhibiting their proliferation (Gosselet et al., *Cell Signal* 19, 731-9, 2007; Kaiser et al., *J Invest Dermatol* 111, 1145-52, 1998). BMP-6 expression was down-regulated in wounded skin at day 3 but increased from days 6-9 (FIG. 5C-D). Treatment of wounds with mammalian or viral VEGF or IL-10 decreased the expression of BMP-6 at day 3 compared with mock-treated wounds (FIG. 5C). Treatment of wounds with both VEGF and IL-10 combination decreased the expression of BMP-6 at day 3, then increased its expression over mock-treated wounds from day 6 (FIG. 5C-D).

EGF promotes keratinocyte proliferation and migration thereby contributing to early wound re-epithelialization (Ando et al., *J Invest Dermatol*, 100, 633-9, 1993; Barrientos et al., *Wound Repair Regen* 16, 585-601, 2008; Rheinwald et al., *Nature* 265, 421-424, 1977). EGF expression decreased in wounded skin at day 3 then started to increase by day 9 (FIG. 5E-F). Treatment of wound with VEGF-A or VEGF-E had slightly increased EGF expression at day 3 compared with mock-treated wounds, while EGF expression was slightly reduced in wounds treated with mIL-10 or vIL-10 (FIG. 5E). Treatment of wounds with VEGF-E and vIL-10 enhanced the expression of EGF over that of the mock-treated wounds from day 3, compared with the mammalian combination which up-regulated EGF expression from day 6 (FIG. 5E-F).

KGF promotes keratinocyte migration and differentiation during late healing thereby contributing to regeneration of the wounded epidermis (Barrientos et al., *Wound Repair Regen* 16, 585-601, 2008; Niu et al., J Biol Chem 282, 6001-6011, 2007). KGF expression decreased in wounded skin till day 6 then had increased by day 9 (FIG. 5G-H). Treatment of wound with VEGF-A, VEGF-E or vIL-10 had little effect on KGF expression at day 3 compared with mock-treated wounds, but KGF expression was reduced in wounds treated with mIL-10 (FIG. 5G). Treatment of wounds with VEGF-E and vIL-10 initially decreased the expression of KGF at day 3 compared with mock-treated wounds then increased its expression from day 6 (FIG. 5G-H). Treatment with VEGF-A and mIL-10 also decreased the expression of KGF at day 3 but did not substantially increase its expression over that of mock-treated wounds at the later time points (FIG. 5G-H).

These results show that the combination of viral VEGF-E and viral IL-10 enhances and accelerates the expression of key regulators of re-epithelization and keratinocyte differentiation, and support the idea that the viral combination will promote epidermal regeneration and resolution in wounded skin to a greater extent than treatment with the mammalian combination or the individual factors.

Example 6

Treatment with Viral VEGF and Viral IL-10 Reduces Inflammatory Cell Recruitment

Treatment of the combination of VEGF and IL-10 reduces inflammatory cell recruitment into the wound to a similar extent as IL-10 treatment alone.

The effect of repeat treatments of viral or mammalian VEGFs, or IL-10s, alone or in combination, on wound inflammation was investigated by immuno-fluorescent staining of F4/80$^{+ve}$ of sections from treated and untreated wounds after 6 days. Representative sections, shown in FIG. 6A, illustrate the increased number of inflammatory cells observed in mock and VEGF-A-treated wounds compared with wounds treated with VEGF-E, IL-10s or the combinations of VEGF and IL-10.

The number of inflammatory cells adjacent to the wound edge was quantified. Wounds treated with VEGF-A had a similar number of macrophages (1.05 F4/80$^{+ve}$ cells/1000 µm$^2$, FIG. 6B) to that of mock-treated and untreated wounds (1.32 and 1.21 F4/80$^{+ve}$ cells/1000 µm$^2$, respectively, FIG. 6B). Wounds treated with VEGF-E, however, showed a significant decrease in the number of macrophages adjacent to the wound (0.79 F4/80$^{+ve}$ cells/1000 µm$^2$, P≤0.05, FIG. 6B), when compared with control wounds. Wounds treated with vIL-10 and mIL-10 also showed a significant decrease in the number of wound macrophages (0.42 and 0.49 F4/80$^{+ve}$ cells/1000 µm$^2$, respectively, P≤0.05, FIG. 6B). Wounds treated with VEGF-E and vIL-10 or VEGF-A and mIL-10 also showed significant decreases in macrophage number (0.60 and 0.34 F4/80$^{+ve}$ cells/1000 µm$^2$, respectively, P≤0.05, FIG. 6B) compared with the mock-treated and untreated wounds, which were similar to that of the decreases seen with the individual IL-10 treatments.

These results demonstrate that repeat treatment of wounds with IL-10, from a mammalian or viral source, decreases inflammatory cell influx into the wound. Treatment with VEGF-A did not influence macrophage recruitment while VEGF-E reduced macrophage recruitment to the wound. Importantly, the addition of VEGF to its respective IL-10 did not reduce the ability of the viral or mammalian IL-10 to reduce wound inflammation.

Example 7

Treatment with Viral VEGF and Viral IL-10 Reduces Wound Inflammation

Treatment with the combination of viral VEGF and viral IL-10 reduces wound inflammation by altering the timing and level of key regulators of inflammatory cell migration and activation.

In this Example, the effect of treatment with VEGF and IL-10 combinations on key regulators of inflammatory cell migration and activation was examined. The effect of the treatments on expression of cytokines and chemokines that regulate the inflammatory phase of tissue repair was examined in the treated and untreated wounds using quantitative real-time (RT)-PCR.

The pro-inflammatory cytokines interleukin (IL)-1β and IL-6 are expressed by infiltrating neutrophils and macrophages and have been implicated in the control of wound re-epithelialization and re-vascularization (reviewed in Barrientos et al., *Wound Repair Regen* 16, 585-601, 2008). IL-10 and IL-6 expression was upregulated in wounded skin at day 3 (FIG. 7A, B). Treatment of wounds with VEGF-A or VEGF-E more than doubled the expression levels of both pro-inflammatory cytokines compared with mock-treated wounds, while expression of the cytokines was substantially reduced in wounds treated with mIL-10 or vIL-10 (FIG. 7A, B). Treatment of wounds with VEGF-E and vIL-10 decreased the expression of IL-10 and IL-6 while treatment with VEGF-A and mIL-10 increased their expression over that of mock-treated wounds (FIG. 7A, B).

The pro-inflammatory chemokines CCL2 (macrophage chemo-attractant protein (MCP)-1) and CXCL2 (macrophage inflammatory protein (MIP)-2a) are expressed by the wounded endothelium and infiltrating macrophages and chemo-attractants for macrophages and neutrophil recruitment, respectively (DiPietro et al., *Am J Pathol*, 146, 868-75, 1995; Seo et al., *Am J Physiol Cell Physiol*, 281, C1568-78, 2001). CCL2 also recruits fibroblasts during inflammation and stimulates them to produce collagen fibers and structural tissues within the wound (Gharee-Kermani et al., *J Biol Chem* 271, 17779-84, 1996. The chemokine CXCL2 contributes to epidermal regeneration and is pro-angiogenic (Devalaraja, *J Invest Dermatol* 115, 234-44, 2000). CCL2 and CXCL2 expression was upregulated in wounded skin at day 3 (FIG. 7C, D). Treatment of wounds with VEGF-A or VEGF-E more than doubled the expression levels of both pro-inflammatory chemokines compared with mock-treated wounds, while expression of the chemokines was substantially reduced in wounds treated with mIL-10 or vIL-10 (FIG. 7C, D). Treatment of wounds with either combination of VEGF and IL-10 decreased the expression of CCL2 and CXCL2 to a level intermediate to that of wounds treated individually with either VEGF or IL-10 (FIG. 7C, D).

The anti-inflammatory cytokine IL-10 is expressed by the wounded epidermis and infiltrating neutrophils and macrophages and has been implicated in the control of scar formation (Peranteau et al., *J Invest Dermatol*, 128, 1852-60, 2008). IL-10 expression was upregulated in wounded skin at day 3 (FIG. 7E). Treatment of wounds with VEGF-A or VEGF-E increased the expression of IL-10 compared with mock-treated wounds, while little difference was seen in wounds treated with mIL-10 or vIL-10 (FIG. 7A, B). Treatment of wounds with VEGF-E and vIL-10 substantially increased the expression of IL-10 over that of mock-treated wounds while treatment with VEGF-A and mIL-10 had very little effect (FIG. 7E).

Osteopontin (secreted phosphoprotein (SPP)-1), a glycoprotein that is involved with adhesion to the extracellular matrix, regulates inflammatory cell and fibroblast trafficking and survival and is thought to contribute to scar formation (Mori et al., *J Exp, Med*, 205, 43-51, 2008). Osteopontin expression was upregulated in wounded skin at day 3 (FIG. 7F). Treatment of wounds with VEGF-A or VEGF-E had no effect on the expression of osteopontin compared with mock-treated wounds, while osteopontin expression was substantially reduced in wounds treated with mIL-10 or vIL-10 (FIG. 7F). Treatment of wounds with either combination of VEGF and IL-10 decreased the expression of osteopontin to a similar level to that of wounds treated individually with IL-10 (FIG. 7F).

These results demonstrate that repeat treatment of wounds with IL-10, from a mammalian or viral source, decreases pro-inflammatory cytokine, chemokine and glycoprotein expression levels. In contrast treatment with either VEGF increased pro-inflammatory gene expression levels. The addition of VEGF to its respective IL-10 did not, however, reduce the ability of the viral or mammalian IL-10 to limit pro-inflammatory gene expression. The altered inflammatory expression levels in IL-10 and combination treated wounds contribute to the reduced inflammatory cell influx. The combination treatment of viral VEGF-E and viral IL-10 reduced the expression of IL-6 and increased the expression of IL-10 within the wound to a greater extent than treatment with the mammalian combination or the individual treatments. Given the roles of these key mediators in scarring these results support the idea that the viral combination limits scarring to a greater extent than the other treatments.

Example 8

Treatment with Viral VEGF and Viral IL-10 Reduces Myofibroblast Differentiation

Treatment of the combination of VEGF and IL-10 reduces myofibroblast differentiation. The addition of VEGF to its respective IL-10 did not diminish the ability of the viral or mammalian IL-10 to reduce myofibroblast differentiation.

The effect of repeat treatments of viral or mammalian VEGFs, or IL-10s, alone or in combination, on myofibroblast differentiation was investigated by immuno-fluorescent staining of sections from treated and untreated wounds for vimentin and SMA within the granulation tissue after 6 days. Representative sections, shown in FIG. 8A, illustrate the extent of αSMA produced by vimentin$^{+ve}$ fibroblasts observed in mock and VEGF-A-treated wounds compared with wounds treated with VEGF-E, IL-10s or the combinations of VEGF and IL-10.

The intensity of αSMA staining within the granulation tissue was quantified. Wounds treated with VEGF-A had a similar αSMA staining ($99 \times 10^7$ total red intensity, FIG. 8B) to that of mock-treated and untreated wounds ($110 \times 10^7$ and $109 \times 10^7$ total red intensity, respectively, FIG. 8B). Wounds treated with VEGF-E, however, showed a significant decrease in αSMA staining ($54 \times 10^7$ total red intensity, $P<0.05$, FIG. 8B), when compared with control wounds. Wounds treated with vIL-10 and mIL-10 also showed a significant decrease in the number of wound macrophages ($76 \times 10^7$ and $64 \times 10^7$ total red intensity, respectively, $P \leq 0.05$, FIG. 8B). Wounds treated with VEGF-E and vIL-10 or VEGF-A and mIL-10 also showed significant decreases in macrophage number ($58 \times 10^7$ and $55 \times 10^7$ total red intensity, respectively, $P \leq 0.05$, FIG. 8B) compared with the mock-treated and untreated wounds, which were similar to that of the decreases seen with the individual IL-10 treatments.

These results demonstrate that repeat treatment of wounds with IL-10, from a mammalian or viral source, decreases myofibroblast differentiation in the wound. Treatment with VEGF-A did not influence αSMA production while VEGF-E did reduce its production within the wound. The addition of VEGF to its respective IL-10 did not, however, reduce the ability of the viral or mammalian IL-10 reduce myofibroblast differentiation.

Example 9

Treatment with Viral VEGF and Viral IL-10 Enhances Wound Re-Vascularization

Treatment of a combination of VEGF and IL-10 enhances wound re-vascularization to a similar extent as VEGF treatment alone.

The effect of repeat treatments of viral or mammalian VEGFs, or IL-10s, alone or in combination, on wound vascularization was investigated by MSB trichrome staining of sections from treated and untreated wounds after 9 days. Representative sections, shown in FIG. 9A, illustrate the increase in dermal blood vessels observed in the wounds treated with the VEGFs, alone or in combination with IL-10.

The extent of dermal vascularization was quantified by determining the areal fraction of blood vessels in the neo-dermis that intersected a grid overlaying the neo-dermis of each section. Wounds treated with VEGF-E or VEGF-A (areal fractions of 0.111 and 0.098, respectively, FIG. 9B) had a significant increase in vascularization over that of mock-treated and untreated wounds (areal fractions of 0.067 and 0.044, respectively, P≤0.05, FIG. 9B). Wounds treated with vIL-10 and mIL-10 (areal fractions of 0.038 and 0.054, respectively, FIG. 9B), however, showed no significant change in vascularization when compared with control wounds. Wounds treated with VEGF-E and vIL-10 or VEGF-A and mIL-10 (areal fractions of 0.091 and 0.098, respectively, P≤0.05, FIG. 9B) also showed significant increases in dermal vascularization compared with the mock-treated and untreated wounds, which were similar to that of the increases seen with the individual VEGF treatments.

These results demonstrate that repeat treatment of wounds with VEGF, from a mammalian or viral source, increases dermal vascularization. Treatment with either IL-10 did not regulate blood vessel formation. Importantly, the addition of IL-10 to its respective VEGF did not impair the ability of the viral or mammalian VEGF to enhance wound re-vascularization.

Example 10

Treatment with Viral VEGF and Viral IL-10 Accelerates Wound Re-Vacularization

Treatment of a combination of VEGF and IL-10 accelerates wound re-vascularization to a greater extent than VEGF treatment alone.

The effect of repeat treatments of viral or mammalian VEGFs, or IL-10s, alone or in combination, on wound vascularization after 9 days was investigated by immune-fluorescent staining of sections for vWF and αSMA to examine the maturation status of blood vessels within the granulation tissue. Mature vessel walls are lined with vWF$^{+ve}$ endothelial cells that are surrounded by αSMA$^{+ve}$ pericytes, which provide structural support and regulate vessel function. Impaired vessel maturation is associated with many human disorders including tumour formation and diabetic wounds (Jain et al., Nat Med, 9, 685-93, 2003). Representative sections, shown in FIG. 10A, illustrate the increase in dermal endothelial cells observed in wounds treated with VEGFs but shows that vessel maturation is increased in treatments containing IL-10.

The number of endothelial cells was quantified within the granulation tissue area. Wounds treated with VEGF-E or VEGF-A (0.68 and 0.72 vWF$^{+ve}$ cells/1000 μm$^2$, respectively, FIG. 10B) had a significant increase in endothelial cells over that of mock-treated and untreated wounds (0.42 and 0.50 vWF$^{+ve}$ cells/1000 μm$^2$, respectively, P≤0.05, FIG. 10B). Wounds treated with vIL-10 and mIL-10 (0.51 and 0.58 vWF$^{+ve}$ cells/1000 μm$^2$, respectively, FIG. 10B), however, showed no significant change in endothelial cell number when compared with control wounds. Wounds treated with VEGF-E and vIL-10 or VEGF-A and mIL-10 (0.70 and 0.75 vWF$^{+ve}$ cells/1000 μm$^2$, respectively, FIG. 10B) also showed significant increases in endothelial cell number compared with the mock-treated and untreated wounds, which were similar to that of the increases seen with the individual VEGF treatments.

The proportion of endothelial cells associated with periocytes was also examined. Wounds treated with VEGF-E or VEGF-A (0.34 and 0.24 vWF$^{+ve}$/αSMA$^{+ve}$ cells/1000 μm$^2$, respectively, FIG. 10B) had minor increases in endothelial cell association with periocytes compared with that of mock-treated and untreated wounds (0.28 and 0.25 vWF$^{+ve}$/αSMA$^{+ve}$ cells/1000 μm$^2$, respectively, FIG. 10B). Wounds treated with vIL-10 and mIL-10 (0.38 and 0.37 vWF$^{+ve}$/αSMA$^{+ve}$ cells/1000 μm$^2$, respectively, FIG. 10B) also showed greater increases in endothelial cell association with periocytes. The increased endothelial cell association with periocytes was also observed in wounds treated with VEGF-E and vIL-10 or VEGF-A and mIL-10 (0.37 and 0.34 vWF$^{+ve}$/αSMA$^{+ve}$ cells/1000 μm$^2$, respectively, FIG. 10B).

The number of red blood cells was quantified within the granulation tissue area. Wounds treated with vIL-10 or VEGF-A (0.94 and 0.72 red blood cells/1000 μm$^2$, respectively, FIG. 10C) showed no significant difference in red blood cell number compared with of mock-treated and untreated wounds (1.05 and 1.31 red blood cells/1000 μm$^2$, respectively, FIG. 10C). Wounds treated with VEGF-E and mIL-10 (0.46 and 0.45 red blood cells/1000 μm$^2$, respectively, FIG. 10C), showed a significant decrease in red blood cell number when compared with control wounds. Wounds treated with VEGF-E and vIL-10 or VEGF-A and mIL-10 (0.46 and 0.36 red blood cells/1000 μm$^2$, respectively, FIG. 10C) also showed significant decreases in red blood cell number compared with the mock-treated and untreated wounds.

These results further demonstrate that repeat treatment of wounds with VEGF, from a mammalian or viral source, increases endothelial cell numbers, while treatment with IL-10 increased endothelial cell association with periocytes. The addition of IL-10 to its respective VEGF increased both the number of endothelial cells and their association with periocytes suggesting that treatment with the combination of VEGF and IL-10 is promoting blood vessel maturation thereby accelerating wound re-vascularization. The results also show that treatment of wounds with a VEGF and IL-10 reduces red blood cell leakage into the granulation tissue suggesting the combination treatments may limit wound edema.

Example 11

Treatment with Viral VEGF and Viral IL-10 Alters the Timing of Key Regulators of Wound Re-Vacularization Treatment of wounded skin with VEGF and IL-10 combinations alters the timing of key regulators of wound re-vascularization. In this Example, the effect of treatments with VEGFs and their IL-10 combinations on the effect of these treatments on key regulators of wound re-vascularization and maturation was examined. The effect of the treatments on expression of growth factors and chemokines and serine proteases known to regulate blood vessel formation within the wound was examined in the treated and untreated wounds.

Figure 11:
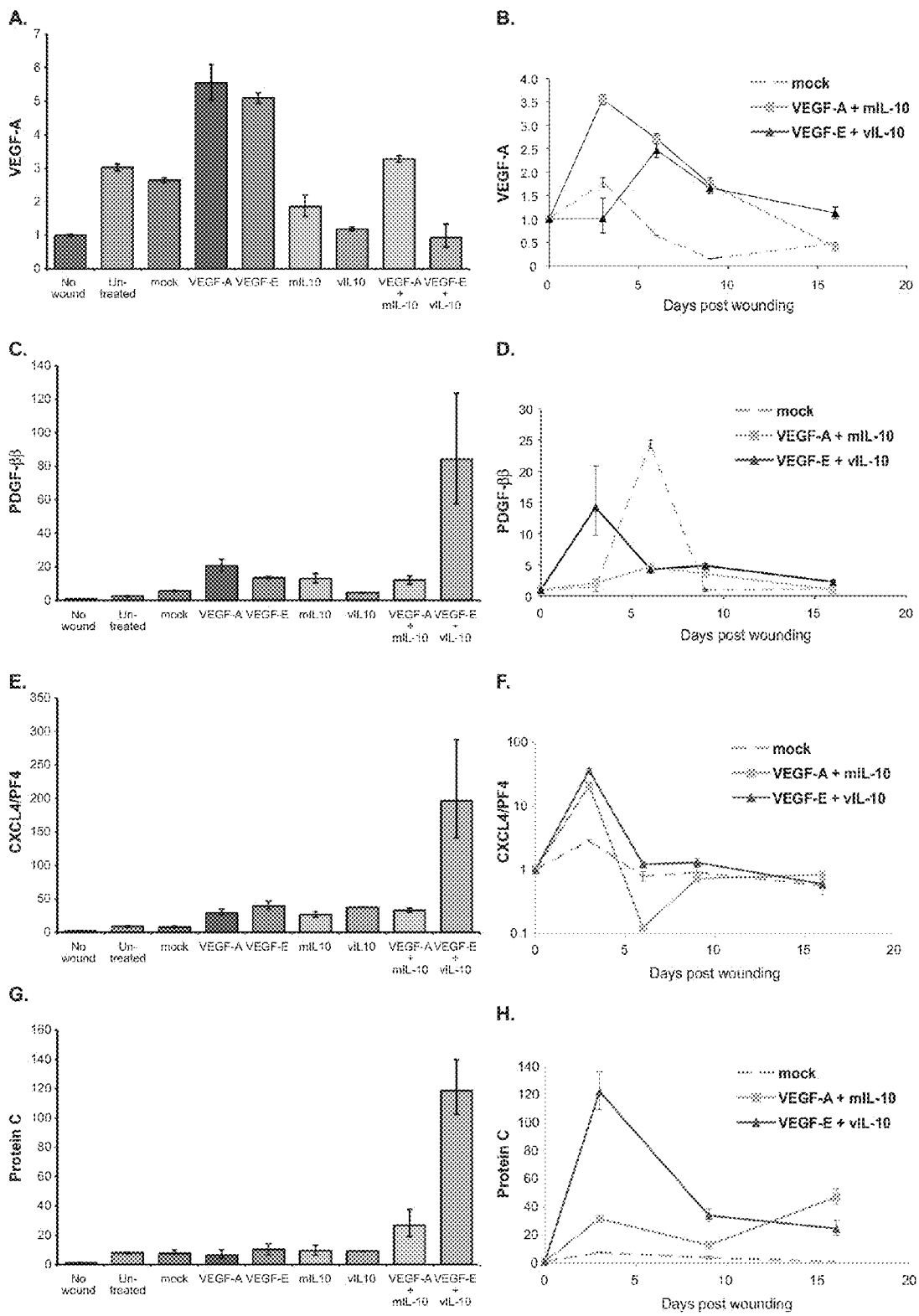
FIG. 11. Combination treatment of viral VEGF and IL-10 promotes vascular regeneration by altering the timing and level of key regulators of blood vessel formation. The expression of key vascular regulators in wounded skin treated with different viral and mammalian factors was examined over time using quantitative RT-PCR. cDNA was prepared by reverse transcription of total RNA (4 left flank wounds combined/treatment group). The level of (A) VEGF-A, (B) PDGF-ββ, (C) CXCL4/PF4 and (D) Protein C mRNA, for all treatments, three days post wounding, are shown in the left panel. The levels of (E) VEGF-A, (F) PDGF-ββ, (G) CXCL4/PF4 and (H) Protein C mRNA, for combination treatments, over the course of healing, are shown in the right panel. All mRNA levels are relative to the levels of GAPDH and unwounded skin. Values represent the mean±SE (n=3) and were consistent with values determined when the procedure was repeated with the 4 right flank wounds from each treatment group.

VEGF-A is expressed by the wounded epidermis and infiltrating macrophages. In wounded skin the expression of VEGF-A peaked at day 6 returning to the level of unwounded skin by day 16 (FIG. 11-B). Treatment of wounds with VEGF-A or VEGF-E further increased its expression while mIL-10 and vIL-10 decreased its expression (FIG. 11A). VEGF-A expression was substantially increased at day 3 when wounds were treated with the combination of VEGF-A and mIL-10. In contrast VEGF-A expression levels in wounds treated with VEGF-E and vIL-10 were below that of mock-treated wounds at day 3 but then increased to above that of mock-treated wounds from day 6 (FIG. 11A-B).

PDGF-ββ is regulates pericyte recruitment thereby promoting blood vessel maturation (Barrientos et al., Wound Repair Regen 16, 585-601, 2008). In wounded skin PDGF-ββ expression peaked at day 6 (FIG. 11C-D). Treatment of wounds with VEGF-A or VEGF-E further increased PDGF-ββ expression while mIL-10 and vIL-10 had little to no effect on its expression (FIG. 11C). PDGF-ββ expression did not increase at any time point tested when wounds were treated with the combination of VEGF-A and mIL-10, but substantially increased in wounds treated with VEGF-E and vIL-10, peaking at day 3 (FIG. 11C-D).

CXCL4, an anti-angiogenic chemokine, interfers with the action of growth factors through its interaction with heparin sulphate on vascular cells (Aidoudi and Bikfalvi, *Thromb Haemost,* 104, 941-8, 2010). In wounded skin CXCL4 expression increased at day 3 then stabilized (FIG. 11E-F). Treatment of wounds with either VEGF or IL-10 caused modest increases in CXCL4 expression (FIG. 11E). Treatment of wounds with VEGF-E and vIL-10 substantially increased the expression of CXCL4 expression over that of mock-treated and VEGF-A and mIL-10-treated wounds from days 3-9 (FIG. 11E-F).

Activated Protein C promotes blood vessel formation and maturation through the regulation of matrix metalloproteinases, angiopoetin and VEGF expression (Jackson et al., *Wound Repair Regen,* 13, 284-94, 2005; Minhas et al., *FASEB J,* 24, 873-81, 2010). In wounded skin Protein C expression increased at day 3 then gradually declined (FIG. 11G-H). Treatment of wounds with either VEGF or IL-10 resulted in little to no change in Protein C expression (FIG. 11G). Treatment of wounds with VEGF-E and vIL-10 however substantially increased the expression of Protein C expression at all time points peaking at day 3 (FIG. 11G-H). VEGF-A and mIL-10 treatment also increased the expression of Protein C expression at all time points although expression peaked at day 16 (FIG. 11G-H).

These results show that the combination of viral VEGF-E and viral IL-10 regulates the expression of key regulators of blood vessel formation, such that the time line of pro- and anti-angiogenic factor expression is accelerated and that treatment with the viral combination enhances vascular regeneration and maturation in wounded skin to a greater extent than with the mammalian combination or individual treatments.

Example 12

Treatment with Viral VEGF and Viral IL-10 Accelerates Dermal Wound Closure with Less Granulation Tissue Formation Treatment with the combination of viral VEGF and viral IL-10 accelerates dermal wound closure but results in less granulation tissue formation than the mammalian treatments, which is indicative of reduced scarring.

This Example was carried out to demonstrate whether the accelerated wound closure observed in wounds treated with the viral factors was due to accelerated dermal regeneration. The direct effect of a single treatment of viral or mammalian VEGFs, or IL-10s, alone or in combination, on the wound neo-dermis was investigated by MSB trichrome staining of sections from treated and untreated wounds after 3, 6 and 9 days. Representative sections shown in FIG. 12A illustrate that wounds treated with the viral factors had greater dermal coverage than the control wounds, while wounds treated with the mammalian factors had increased granulation tissue deposition.

We quantitated dermal closure by determining the percentage of total wound bed covered by granulation tissue as illustrated in FIG. 12B. By day 3 the granulation tissue covered 32% of the wound bed in wounds treated with VEGF-E, which was significantly greater than the percentage dermal closure seen in mock-treated and untreated wounds (14% and 9%, respectively, P≤0.05, FIG. 12C). VEGF-E-treated wounds also showed a significantly greater level of dermal closure (16%, FIG. 12C) than that of VEGF-A-treated wounds by day 3. Treatment of wounds with VEGF-E continued to significantly increase dermal closure by day 6, with the granulation tissue covering 74% of the wound bed compared with the mock-treated and untreated wounds (52% and 43%, respectively, P≤0.05, FIG. 12C). At day 6, VEGF-E-treated wounds also showed significantly greater dermal closure than that of VEGF-A-treated wounds (65%, P≤0.05, FIG. 12C). By day 9, all wounds showed 100% dermal closure (FIG. 2E).

By day 3 the granulation tissue covered 25% and 23% of the wound bed in wounds treated with vIL-10 and mIL-10, respectively, both of which were significantly greater than the percentage dermal closure seen in mock-treated and untreated wounds (P≤0.05, FIG. 12C). Treatment of wounds with vIL-10 continued to significantly increase dermal closure by day 6, with the granulation tissue covering 70% of the wound bed compared with the mock-treated and untreated wounds (52% and 43%, respectively, P≤0.05, FIG. 12C). At day 6, vIL-10-treated wounds showed equivalent levels of dermal closure to that of mIL-10-treated wounds (66%, P≤0.05, FIG. 12C). Treatment of wounds with both vIL-10 and mIL-10 also significantly increased dermal coverage, compared with the control wounds, with the granulation tissue covering 69% and 66% of the wound bed, respectively (P<0.05, FIG. 12C).

Treatment of wounds with the combination of VEGF-E and vIL-10 significantly increased dermal coverage at day 3 (46%), compared with the VEGF-A and mIL-10 combination-treated and mock-treated wounds (28% and 14%, respectively (P≤0.05, FIG. 12C). By day 6, treatment of wounds with the combination of VEGF and IL-10 showed similarly significantly increases in dermal coverage, compared with the mock-treated wounds, with the granulation tissue covering 72% and 61% of the wound bed in wounds treated with VEGF-E and vIL-10 or VEGF-A and mIL-10, respectively (P≤0.05, FIG. 12C). Wounds treated with the viral combination showed significantly greater dermal coverage at day 6 than wounds treated with the mammalian combination (P≤0.05, FIG. 12C). Overall at day 3, the granulation tissue within the wounds treated with VEGF-E had an area of 13368 $\mu m^2$, which was significantly greater than the areas of the mock-treated and untreated wounds (7852 $\mu m^2$ and 5016 $\mu m^2$, respectively, P≤0.05, FIG. 12D). The area of granulation tissue seen in VEGF-E-treated wounds was not however significantly greater than that of VEGF-A-treated wounds (13047 $\mu m^2$, FIG. 12D). By day 6, the area of granulation tissue of VEGF-E-treated wounds had increased to 21067 $\mu m^2$, which was similar to the areas of the mock-treated and untreated wounds (20116 $\mu m^2$ and 18255 $\mu m^2$, respectively, FIG. 12D). At day 6, the area of granulation tissue in VEGF-A-treated wounds was significantly greater (26663 $\mu m^2$, P≤0.05, FIG. 12D) than that of VEGF-E-treated wounds. At day 9, the areas of granulation tissue in wounds treated with VEGF-A had continued to increase in size (57712 $\mu m^2$, FIG. 12D), as had the areas of mock-treated and untreated wounds (52100 $\mu m^2$ and 42372 $\mu m^2$, respectively, FIG. 12D). In contrast, the area of the granulation tissue in VEGF-E-treated wounds at day 9 was now significantly less than the control and VEGF-A-treated wounds (33927 $\mu m^2$, P≤0.05, FIG. 12D).

At day 3, the granulation tissue within the wounds treated with vIL-10 had an area of 15419 $\mu m^2$, which was significantly greater than the areas of the mock-treated and untreated wounds (P≤0.05, FIG. 12D). The area of granulation tissue seen in vIL-10-treated wounds was also significantly greater than that of mIL-10-treated wounds (12408

μm², FIG. 12D). By day 6, the area of granulation tissue of vIL-10-treated wounds had increased to 23986 μm², which was similar to the areas of the mock-treated and untreated wounds (FIG. 12D), but was significantly less than the area in mIL-10-treated wounds (28012 μm², P≤0.05, FIG. 12D). At day 9, the areas of granulation tissue in wounds treated with vIL-10 and mIL-10 had stopped increasing in size (30362 μm² and 31482 μm², respectively, FIG. 12D) and were significantly less than the areas of mock-treated and untreated wounds (FIG. 12D).

In wounds treated with the combination of VEGF-E and vIL-10, the area of the granulation tissue at day 3 (27962 μm², P≤0.05, FIG. 12D) was significantly greater than in wounds treated with the individual viral factors or mock-treated wounds. In contrast the wounds treated with the combination of VEGF-A and mIL-10 the area of the granulation tissue at day 3 (12004 μm², P≤0.05, FIG. 12D) was significantly greater than in mock-treated wounds but not in the wounds treated with the individual mammalian factors. The granulation tissue area in wounds treated with the viral combination was also significantly greater than wounds treated with the mammalian combination (P≤0.05, FIG. 12D). By day 6, the area of the granulation tissue in wounds treated with VEGF-E and vIL-10 had decreased in size (23121 μm², FIG. 12D) and was similar in area to the mock-treated wounds. The granulation tissue area of wounds treated with VEGF-A and VEGF-E had continued to increase in size (24898 μm², FIG. 12D) and was also similar to the mock-treated wounds. At day 9, wounds treated with VEGF-E and vIL-10 had substantially less granulation tissue area than wounds treated with VEGF-A and mIL-10 (25070 μm² and 32078 μm², respectively, P≤0.05, FIG. 12D) but both combinations had significantly less granulation tissue than the mock-treated wounds.

These results demonstrate that treatment of wounds with mammalian VEGF-A or IL-10, alone or in combination, increases granulation tissue deposition and dermal closure. Treatment of wounds with viral VEGF-E and viral IL-10 initially increased granulation tissue deposition to a greater extent than the mammalian combination or the individual treatments which then resulted in a substantially reduced granulation tissue area, which indicates that acceleration of dermal healing will ultimately limit scar area.

Example 13

Treatment with Viral VEGF and Viral IL-10 Accelerates Granulation Tissue Remodeling Treatment with the combination of viral VEGF and viral IL-10 accelerates granulation tissue remodeling from a fibrin to collagen matrix to a greater extent than the individual or mammalian treatments.

This Example was carried out to demonstrate whether the reduced granulation tissue deposition and enhanced dermal closure observed in wounds treated with the viral factors influenced dermal remodeling. Collagen content was quantitated using MSB trichrome staining of sections from wounds after 9 days. The staining data show that wounds treated with the viral VEGF-E or IL-10, had increased intensities of blue pixel staining within granulation tissue wounds (162 and 160, respectively, FIG. 13), which were significantly greater than the collagen staining in mock-treated and untreated wounds (156 and 157, respectively, P≤0.05, FIG. 13). Treatment with the combination of VEGF-E and vIL-10 also significantly increased the collagen content of the granulation tissue, compared with the control wounds (72, P≤0.05, FIG. 13). Treatment of wounds with either VEGF-A or mIL-10, however, resulted in little difference in collagen content (64 and 66, respectively, FIG. 13), while the combined treatment had significantly less collagen staining than the control wounds (150, P≤0.05, FIG. 13). Wounds treated with each viral factor or combination showed a significant increase in collagen content over wounds treated with the equivalent mammalian factor or combination (P≤0.05, FIG. 13). The collagen content in wounds treated with the viral combination was also significantly greater than wounds treated with the viral IL-10 (P≤0.05, FIG. 13) and was also substantially greater than the wounds treated with just VEGF-E (P=0.068, FIG. 13).

These results demonstrate that treatment of wounds with viral VEGF-E and viral IL-10 in combination increased collagen deposition within the granulation tissue, to a greater extent than the other treatments, which supports the idea that the viral combination treatment will accelerate dermal remodelling.

Example 14

Treatment with Viral VEGF and Viral IL-10 Enhances Granulation Tissue Remodeling by Altering the Timing of Key Regulators of Dermal Maturation This Example was carried out to evaluate the effect of treatments VEGFs and their IL-10 combinations on key regulators of granulation dermal closure and granulation tissue remodeling. The effect of the treatments on expression of factors known to regulate wound contraction and granulation tissue turnover was examined in the treated and untreated wounds.

Dermal wound closure is enhanced by myo-fibroblasts that express αSMA filaments, which grip the wound edges and contract themselves making wounds smaller (Werner et al., *J Invest Dermatol*, 127, 998-1008, 2007). In wounded skin the expression of αSMA peaked at day 6 and remained above the level of unwounded skin at all time points tested (FIG. 14A). The expression of αSMA was substantially reduced, at days 6 and 9, when wounds were treated with the combination of VEGF-A and mIL-10 or VEGF-E and vIL-10, compared with mock-treated wounds (FIG. 14A).

Production of TGF-β1 by wound macrophages promotes fibroblast differentiation into myo-fibroblasts aiding wound contraction and closure (Chalmers, *Int Wound J*, 8, 218-23, 2011; Shih et al., *Wound Repair Regen*, 18, 139-53, 2010). TGF-β1 also stimulates type I collagen synthesis by fibroblasts and prevents its degradation. Increased TGF-β1 expression appears to correlate with increased fibrosis and scarring. In wounded skin the expression of TGF-β1 increased from day 3-9 and returned to the level of unwounded skin by day 16 (FIG. 14B). In wounds treated with the mammalian combination of VEGF-A and mIL-10, TGF-β1 expression was initially increased above that of mock-treated wounds (FIG. 14B). In contrast, wounds treated with the viral combination of VEGF-E and vIL-10, initially showed reduced expression of TGF-β1 compared with mock-treated wounds (FIG. 14B).

Another TGF-β isoform, TGF-β3, has been associated with reduced scarring and possibly acting as a receptor antagonist thereby reducing collagen deposition (Shih et al., *Wound Repair Regen*, 18, 139-53, 2010). In wounded skin the expression of TGF-β3 peaked at day 6 and returned to the level of unwounded skin by day 16 (FIG. 14C). In wounds treated with the mammalian combination of VEGF-A and mIL-10, TGF-β3 expression was initially less than that of mock-treated wounds but was substantially higher by day 9

(FIG. 14C). In contrast, wounds treated with the viral combination of VEGF-E and vIL-10, showed increased expression of TGF-β3 compared with mock-treated wounds at all of the time points tested (FIG. 14C).

Apoptosis is an important aspect to wound healing the means by which each cell population, such as macrophages and fibroblasts, once their tasks are complete are removed from the wound site (Shih et al., *Wound Repair Regen,* 18, 139-53, 2010). Reduced apoptosis leading to an imbalance in matrix turnover is thought to contribute to scar formation. The p53 tumour suppressor gene is a key inducer of apoptosis during tissue repair. In wounded skin the expression of p53 was decreased at day 3, returned to the level of unwounded skin at day 6, then was decreasing again by day 9 (FIG. 14D). In wounds treated with the mammalian combination of VEGF-A and mIL-10, p53 expression initially decreased like that of mock-treated wounds but then increased at days 6 and 9 (FIG. 14D). Wounds treated with the viral combination of VEGF-E and vIL-10, also initially decreased but then showed a more substantial increase in expression of p53 compared with mock-treated wounds at the later time points (FIG. 14D).

As the wound matures, the matrix of the granulation tissue is turned over from fibrin to the immature type III collagen, which becomes converted to the mature type I collagen that strengthens the scar (Olivveira et al., *Int Wound J,* 6, 445-52, 2009). In wounded skin, the expression of type III and type I collagen both peaked at day 6 then returned to the level of unwounded skin by day 16 (FIG. 14E, F). Treated of wounds with either combination of VEGF and IL-10, increased the expression of both type III and I collagen to levels above that of the mock-treated wounds at days 6 (FIG. 14E, F). In wounds treated with the viral combination of VEGF-E and vIL-10, the increased expression of the mature type I collagen was maintained till day 9, while in wounds treated with the mammalian combination of VEGF-A and mIL-10 the increased expression of the immature type III collagen was maintained till day 9 (FIG. 14E, F).

These results show that treatment of wounds with the viral combination of VEGF-E and vIL-10 is influencing matrix turnover, with increased collagen and TGF-β3 expression. Treatment of the wounds with the viral VEGF-E/vIL-10 combination also appeared to enhance cellular apoptosis suggesting accelerated wound maturation. The mammalian combination also increased collagen, TGF-β3 and p53 expression within the wound but not the extent shown with the viral combination. Viral combination-treated wounds appear to have accelerated wound closure but this is not consistent with the reduced expression of αSMA and TGF-β1, key molecules involved in myo-fibroblast activation and wound contraction, that peak during the early phase of healing. It is however possible that αSMA expression in combination-treated wounds may peak at an earlier time point than was examined in this study, in which would be consistent with accelerated wound contraction.

Example 15

Treatment with Viral VEGF and Viral IL-10 Enhances Scar Resolution

Treatment with the combination of viral VEGF-E and viral IL-10 enhances scar resolution to a greater extent than the individual or mammalian treatments.

In this Example, the scars from wounds treated with the viral or mammalian VEGFs, or IL-10s, alone or in combination and were compared to those of untreated or mock-treated wounds.

Photographs taken of the healed wounds revealed differences in scar resolution between the treatment groups that were quantified by visual scoring of scar severity and by measurement of internal scar area (FIG. 15A). Treatment of wounds with VEGF-E, alone or in combination with vIL-10 resulted in a significant reduction in external scar score at day 13 compared to mock-treated wounds (FIG. 15B). Treatment of wounds with vIL-10, alone or in combination with VEGF-E resulted in a significant reduction in internal scar area at day 16 compared to mock-treated wounds (FIG. 15C). Treatment with the mammalian VEGF-A or IL-10, alone or in combination had little to no positive effect on scar score or size.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any examiner or other official or employee of government patent office unless such statement is specifically and without qualification or reservation expressly adopted in a responsive writing by or on behalf of the inventor(s).

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method of treating a subject having a wound not healing at an expected rate, which comprises administration of an effective amount of a viral VEGF selected from the group consisting of a parapoxvirus VEGF E and an orf virus VEGF-E, and (ii) an anti-inflammatory cytokine, optionally a viral anti-inflammatory cytokine, optionally a viral anti-inflammatory interleukin, optionally viral IL-10, to a subject in need of treatment therewith, wherein said viral VEGF-E and said viral anti-inflammatory cytokine are administered in combination or administered separately.

2. A method according to claim 1, wherein said viral VEGF is a parapoxvirus virus VEGF-E.

3. A method according to claim 1, wherein said viral anti-inflammatory cytokine is selected from the group consisting of parapoxvirus IL-10 and orf virus IL-10.

4. A method according to claim 1, wherein the subject suffers from a wound selected from the group consisting of an acute wound, a delayed-healing wound, an incompletely healing wound, a chronic wound (optionally a diabetic ulcer, a venous ulcer, a pressure ulcer, a vasculitic ulcer, or an arterial ulcer), and a dehiscent wound, and wherein the composition optionally is applied prior to repair or closure of a wound.

5. A composition comprising a viral VEGF selected from the group consisting of a parapoxvirus VEGF-E and an orf virus VEGF-E and a viral anti-inflammatory cytokine effective to promote wound healing and a pharmaceutically acceptable carrier, wherein the composition optionally is formulated for administration via a route selected from the group consisting of topical administration and injection.

6. A composition according to claim 5 which is in the form of a cream, ointment, gel, emulsion, lotion, foam, or paint, wherein when the composition is a gel, the gel optionally comprises a nonionic polyoxyethylene-polyoxypropylene copolymer gel.

7. A composition according to claim 5, wherein said viral VEGF is a parapoxvirus virus VEGF-E.

8. A composition according to claim 5, wherein said viral anti-inflammatory cytokine is selected from the group consisting of a parapoxvirus IL-10 and an orf virus IL-10.

9. A method of manufacture of a medicament comprising bringing together amounts of a viral VEGF selected from the group consisting of a parapoxvirus VEGF-E and an orf virus VEGF-E and a viral anti-inflammatory cytokine effective to promote wound healing and a pharmaceutically acceptable carrier.

10. A method according to claim 9, wherein said viral VEGF is VEGF-E, wherein the VEGF-E optionally is a parapoxvirus virus VEGF-E.

11. A method according to claim 9, wherein said viral anti-inflammatory cytokine is a viral anti-inflammatory interleukin, optionally viral IL-10, optionally parapoxvirus IL-10, optionally orf virus IL-10.

12. An article of manufacture comprising package material containing therapeutically effective amounts of a viral VEGF selected from the group consisting of a parapoxvirus VEGF-E and an orf virus VEGF-E and a viral anti-inflammatory cytokine together with instructions for use in the treatment of a wound in or on a subject.

13. An article of manufacture according to claim 12, wherein the viral VEGF and the viral anti-inflammatory cytokine are contained in a single vessel.

14. An article of manufacture according to claim 12, wherein the viral VEGF and the viral anti-inflammatory cytokine are contained in separate vessels.

15. An article of manufacture according to claim 12, wherein said viral VEGF is a parapoxvirus virus VEGF-E.

16. An article of manufacture according to claim 12, wherein said viral anti-inflammatory cytokine is a viral anti-inflammatory interleukin, optionally viral IL-10, optionally parapoxvirus IL-10, optionally orf virus IL-10.

17. An article of manufacture according to claim 12, wherein the subject suffers from a wound selected from the group consisting of an acute wound, a delayed-healing wound, an incompletely healing wound, a chronic wound (optionally a diabetic ulcer, a venous ulcer, a pressure ulcer, a vasculitic ulcer, or an arterial ulcer), and a dehiscent wound, and wherein the composition optionally is applied prior to repair or closure of a wound.

18. An article of manufacture according to claim 12, wherein the viral VEGF and the viral anti-inflammatory cytokine are (a) formulated for administration by injection or (b) formulated for topical administration.

19. An article comprising package material containing therapeutically effective amounts of each of (i) a viral VEGF selected from the group consisting of a parapoxvirus VEGF-E and an orf virus VEGF-E, and (ii) an anti-inflammatory cytokine, optionally a viral anti-inflammatory cytokine, optionally a viral anti-inflammatory interleukin, optionally viral IL-10, together with instructions for use in the treatment of a wound in or on a subject.

20. A composition comprising a viral VEGF selected from the group consisting of a parapoxvirus VEGF-E and an orf virus VEGF-E and a mammalian anti-inflammatory cytokine effective to promote wound healing and a pharmaceutically acceptable carrier, wherein the composition optionally is formulated for administration via a route selected from the group consisting of topical administration and injection.

21. A composition according to claim 20, wherein the mammalian anti-inflammatory cytokine is a mammalian anti-inflammatory interleukin.

22. A composition according to claim 21, wherein the mammalian anti-inflammatory interleukin is IL-10.

23. An article of manufacture comprising package material containing therapeutically effective amounts of a viral VEGF selected from the group consisting of a parapoxvirus VEGF-E and an orf virus VEGF-E and a mammalian anti-inflammatory cytokine together with instructions for use in the treatment of a wound in or on a subject.

24. An article of manufacture according to claim 23, wherein the mammalian anti-inflammatory cytokine is a mammalian anti-inflammatory interleukin.

25. An article of manufacture according to claim 24, wherein the mammalian anti-inflammatory interleukin is IL-10.

26. A method according to claim 1, wherein the anti-inflammatory cytokine is a mammalian anti-inflammatory cytokine.

27. A method according to claim 26, wherein the mammalian anti-inflammatory cytokine is a mammalian anti-inflammatory interleukin.

28. A method according to claim 27, wherein the mammalian anti-inflammatory interleukin is IL-10.

29. An article according to claim 19, wherein the anti-inflammatory cytokine is a mammalian anti-inflammatory cytokine.

30. An article according to claim 29, wherein the mammalian anti-inflammatory cytokine is a mammalian anti-inflammatory interleukin.

31. An article according to claim 30, wherein the mammalian anti-inflammatory interleukin is IL-10.

* * * * *